(12) United States Patent
Liu et al.

(10) Patent No.: US 11,591,328 B2
(45) Date of Patent: Feb. 28, 2023

(54) HIGHLY ACTIVE CSF1R INHIBITOR COMPOUND

(71) Applicant: XIAMEN BIOTIME BIOTECHNOLOGY CO., LTD., Fujian (CN)

(72) Inventors: Shifeng Liu, Zhejiang (CN); Zhiyong Yu, Zhejiang (CN); Wei Pang, Zhejiang (CN); Ji Wang, Zhejiang (CN); Peng Chen, Zhejiang (CN)

(73) Assignee: XIAMEN BIOTIME BIOTECHNOLOGY CO., LTD., Fujian (CN)

( * ) Notice: Subject to any disclaimer, the term of this patent is extended or adjusted under 35 U.S.C. 154(b) by 6 days.

(21) Appl. No.: 16/977,093

(22) PCT Filed: May 24, 2019

(86) PCT No.: PCT/CN2019/088221
§ 371 (c)(1),
(2) Date: Aug. 31, 2020

(87) PCT Pub. No.: WO2019/228252
PCT Pub. Date: Dec. 5, 2019

(65) Prior Publication Data
US 2020/0399265 A1    Dec. 24, 2020

(30) Foreign Application Priority Data
Jun. 1, 2018  (CN) .......................... 201810559228.2

(51) Int. Cl.
*C07D 417/14* (2006.01)
*C07D 401/14* (2006.01)
*C07D 491/107* (2006.01)
*C07D 487/10* (2006.01)

(52) U.S. Cl.
CPC ......... *C07D 417/14* (2013.01); *C07D 401/14* (2013.01); *C07D 487/10* (2013.01); *C07D 491/107* (2013.01)

(58) Field of Classification Search
CPC .. C07D 417/14; C07D 401/14; C07D 487/10; C07D 491/107
USPC ..................................................... 514/333
See application file for complete search history.

(56) References Cited

U.S. PATENT DOCUMENTS

| | | |
|---|---|---|
| 2014/0315917 A1 | 10/2014 | Flynn et al. |
| 2015/0037280 A1 | 2/2015 | Xi et al. |
| 2020/0071302 A1 | 3/2020 | Zhao et al. |

FOREIGN PATENT DOCUMENTS

| | | |
|---|---|---|
| CN | 103539780 A | 1/2014 |
| CN | 104974162 A | 10/2015 |
| CN | 110573500 B | 12/2020 |
| EP | 3632907 A1 | 4/2020 |
| JP | 2020520978 A | 7/2020 |
| WO | 2006116713 A1 | 11/2006 |
| WO | 2014022117 A1 | 2/2014 |
| WO | 2014145015 A2 | 9/2014 |
| WO | 2015164161 A1 | 10/2015 |
| WO | 2017176792 A1 | 10/2017 |
| WO | 2018081254 A1 | 5/2018 |
| WO | 2018214867 A1 | 11/2018 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
First Office Action dated Oct. 4, 2021 for Japanese patent application No. 2021-510517, English translation provided by Global Dossier.
Search Report dated Oct. 20, 2021 for European patent application No. 19810043.0.
International Search Report for PCT/CN2019/088221 dated Aug. 30, 2019, ISA/CN.
D. L. Scott et al. The links between joint damage and disability in rheumatoid arthritis, Rheumatology 2000, 39:122-132.
Christopher T. Ritchlin, et al. Mechanisms of TNF-α-and RANKL-mediated osteoclastogenesis and bone resption in psoriatic arthritis, J. Clin. Invest. 2003, 111:821-831.
James G. Conway, et al. Effects of the cFMS Kinase Inhibitor 5-(3-Methoxy-4-((4-methoxybenzyl)oxy)benzyl) pyrimidine-2,4-diamine (GW2580) in Normal and Arthritic Rats, JPET 2008, 326: 41-50.
Hiroaki Ohno, et al. The orally-active and selective c-Fms tyrosine kinase inhibitor Ki20227 inhibits disease propression in a collagen-induced arthritis mouse model, Eur. J. Immunol. 2008, 38: 283-291.

* cited by examiner

*Primary Examiner* — Kristin A Vajda
(74) *Attorney, Agent, or Firm* — Yue (Robert) Xu; Apex Attorneys at Law, LLP

(57) ABSTRACT

The present invention relates to a CSF1R inhibitor, and in particular to a highly active CSF1R inhibitor compound having the structure of formula (I). Said compound of the present invention has high inhibitory activity on CSF1R.

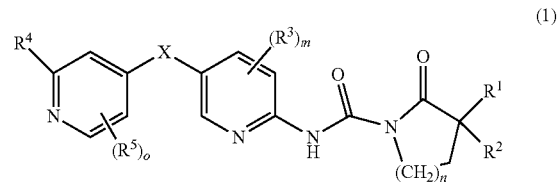

(1)

20 Claims, 1 Drawing Sheet

HIGHLY ACTIVE CSF1R INHIBITOR COMPOUND

The present application is the national phase of International Application No. PCT/CN2019088221, titled "highly active CSF1R inhibitor compound", which claims benefits priority of Chinese Patent Application Serial NO. 201810559228.2 filed on Jun. 1, 2018 with the Chinese Patent Office, titled "highly active CSF1R inhibitor compound", which is hereby incorporated by reference in its entirety.

FIELD

The present invention relates to heterocyclic compounds, in particular to a highly active CSF1R inhibitor and its use.

BACKGROUND

CSF1R (colony stimulating factor 1 receptor) is an important cytokine during the differentiation and recruitment of macrophages, secreted by tumor cells. Reported research results showed that CSF1R inhibitors (antibodies or small molecules) can reduce TAM (tumor-associated macrophages) infiltration of tumor tissues, effectively inhibit tumor progression and metastasis, and become a new focus in tumor immunotherapy.

Due to its role in osteoclast biology, CSF1R is considered an important therapeutic target for osteoporosis and inflammatory arthritis. For example, increased M-CSF signaling leads to increased osteoclast activity, which leads to bone loss associated with arthritis and other inflammatory bone erosions (see Scott et al. Rheumatology 2000, 39:122-132, Ritchlin et al. J. Clin. Invest. 2003, 111:821-831). Therefore, the inhibition of CSF1R represents a promising treatment option for arthritis and other inflammatory bone erosions. The efficacy data of known CSF1R inhibitors such as Ki-20227 and GW2580 in arthritis animal models further support this (See Conwat et al. JPET 2008, 326: 41-50 and Ohno et al. Eur. J. Immunol. 2008, 38: 283-291). The abnormal regulation of osteoclast development that leads to osteoporosis and the disruption of the balance between bone erosion and osteogenesis may also be treated by the regulation of CSF1R.

Novartis scientists reported in the Nature magazine that pre-clinical studies have shown that in mouse glioma models, inhibition of CSF1R (BLZ945) can lead to a rapid decrease in tumor volume and a significantly prolonged survival. This inhibitory effect of CSF1R did not kill the tumor related macrophages, but re-transform them to anti-tumor state; similar results were also reported in cervical cancer and breast cancer models. Small molecule inhibitors of CSF1R can also effectively enhance the body's sensitivity to chemotherapy. Five Prime (cooperating with BMS to develop CSF1R inhibitors) studied in mouse models of pancreatic cancer and found that the use of CSF1R inhibitors in combination with an immune checkpoint inhibitor has a synergistic effect and significantly inhibits the growth of pancreatic tumors in mice.

CSF1R antibody drugs currently entering the clinic include BMS/FPRX's FPA008, Roche's emactuzumab, Eli Lilly's LY3022855, Amgen's AMG820, etc. The clinical CSF1R small molecule drugs include BLZ945, Plexxikon's PLX3397, Deciphera's DC-3014, etc. The combination of CSF1R inhibitors and immune checkpoint inhibitors is still in the early clinical stage, and no compound has entered the clinical application in China. There is a continuing need for the identification of small molecules that inhibit CSF1R, especially compounds that can be used to treat CSF1R-related diseases.

SUMMARY

The present invention provides a compound of formula (I) or a pharmaceutically acceptable salt, solvate, hydrate, stereoisomer, mixture of stereoisomers or racemic mixture of stereoisomers. In certain embodiments, the compound has activity as a CSF1R inhibitor. It should be pointed out that when the present disclosure generally refers to the compound of formula I, it is not necessary to list some or all of the following at the same time: its pharmaceutically acceptable salts, solvates, hydrates, stereoisomers, and stereoisomers. Conformer mixtures or racemic mixtures of stereoisomers. In this case, the compound of formula I also encompasses its pharmaceutically acceptable salts, solvates, hydrates, stereoisomers, mixtures of stereoisomers, and racemic mixtures of stereoisomers.

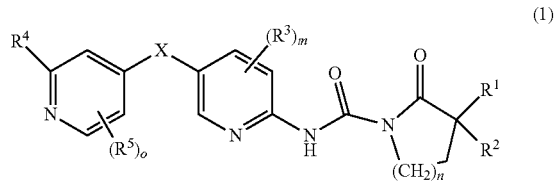

(1)

wherein, X represents $CR^aR^{a'}$,

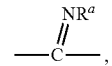

$NR^a$, —C(O)—, O, S, S(O), $S(O)_2$;

$R_1$ and $R_2$, together with the carbon atom directly attached thereto form a saturated or unsaturated 3 to 12 membered cycloalkyl or cycloheteroalkyl ring, the heterocycloalkyl group contains at least one heteroatom selected from O, N and S, the cycloalkyl group or heterocycloalkyl group can be optionally substituted by 0, 1, 2, 3 or 4 substituents each independently selected from the following $R^6$: halogen, hydroxy, $C_1$-$C_8$ alkyl, $C_3$-$C_8$ cycloalkyl, $C_3$-$C_8$ heterocycloalkyl, $C_2$-$C_8$ alkenyl, $C_2$-$C_8$ alkynyl, $C_1$-$C_8$ haloalkyl, $C_1$-$C_8$ alkoxy, $C_1$-$C_8$ haloalkoxy, $C_3$-$C_8$ cycloalkoxy, $C_3$-$C_8$ heterocyclic alkoxy, —S—($C_1$-$C_8$) alkyl, —S—($C_3$-$C_8$) cycloalkyl, —S—($C_3$-$C_8$) heterocycloalkyl, cyano, nitro, —($C_0$-$C_8$) alkyl-$NR_9R^{a'}$, —C=$NR^a$, —O-Cy1, —O—($C_0$-$C_8$)alkyl-Cy$^1$, —($C_2$-$C_8$)alkenyl-Cy$^1$, —($C_2$-$C_8$)alkynyl-Cy$^1$, —C(O)OR$^a$, —C(O)R$^a$, —OC(O)R$^a$, —C(O)—NR$^a$R$^{a'}$, —NR$^a$—C(O)—R$^a$, —NR$^a$—C(O)—OR$^a$, —($C_1$-$C_8$) alkyl-NR$^a$—C(O)R$^a$, —SO$_2$—NR$^a$R$^{a'}$ and —SO$_2$R$^a$;

$R^3$ and $R^5$ each independently represent hydrogen, halogen, $C_1$-$C_8$ alkyl, $C_1$-$C_8$ alkoxy, $C_3$-$C_8$ cycloalkyl, $C_3$-$C_8$ heterocycloalkyl, halogenated $C_1$-$C_8$ alkyl, hydroxyl, amino, nitro, cyano, —C(O)OR$^a$, —OC(O)R$^a$, —C(O)—NR$^a$R$^{a'}$, —NR$^a$—C(O)—R$^a$, —NR$^a$—C(O)—OR$^a$, —($C_1$-$C_8$)alkyl-NR$^a$—C(O)R$^a$, —SO$_2$—NR$^a$R$^{a'}$ or —SO$_2$R$^a$;

$R^4$ represents Cy$^2$, —NHC(O)R$^a$, —NHC(O)NR$^a$R$^{a'}$, —C(O)R$^a$, —C(O)NR$^a$R$^{a'}$, —S(O)$_2$R$^a$, S(O)$_2$NR$^a$R$^{a'}$, NHS(O)$_2$R$^a$ or —NHS(O)$_2$NR$^a$R$^{a'}$;

wherein, Cy$^1$ and Cy$^2$ each independently represent a 5-12 membered ring which was independently substituted by 0, 1, 2, 3 or 4 substituents, preferably a 5-12 membered aryl group or a 5-12 membered heteroaryl group; more preferably a 5-6 membered aryl group or a 5-6 membered heteroaryl group, wherein the substituents are halogen, $C_1$-$C_8$ alkyl, $C_1$-$C_8$ alkoxy, $C_3$-$C_9$ cycloalkyl, $C_3$-$C_9$ heterocycle alkyl, halogenated $C_1$-$C_8$ alkyl, hydroxy, nitro, cyano, —C(O)OR$^a$, —OC(O)R$^a$, —C(O)—NR$^a$R$^{a'}$, —NR$^a$—C(O)—R$^a$, —NR$^a$—C(O)—OR$^a$, —($C_1$-$C_8$)alkyl-NR$^a$—C(O)R$^a$, —SO$_2$—NR$^a$R$^{a'}$ and —SO$_2$R$^a$;

wherein, R$^a$ and R$^{a'}$ independently represent hydrogen, $C_1$-$C_8$ alkyl, $C_3$-$C_9$ cycloalkyl, hydroxyl, halogen, amino, $C_1$-$C_8$ haloalkyl, $C_1$-$C_8$ alkylamino, di-$C_1$-$C_8$ alkylamino group or R$^a$, R$^{a'}$ together with the atom directly attached thereto form a 3-9 membered cycloalkyl or heterocycloalkyl ring, preferably hydrogen, $C_1$-$C_8$ alkyl or $C_3$-$C_8$ cycloalkyl; n is 1, 2 or 3, preferably 1; m and o independently represent 0, 1, 2 or 3, for the above-defined alkyl, cycloalkyl, heterocycloalkyl, aryl, and heteroaryl groups, can further be substituted with the substituents selected from the following: $C_1$-$C_8$ alkyl, $C_2$-$C_8$ alkenyl, $C_2$-$C_8$ alkynyl, $C_3$-$C_8$ cycloalkyl, 5-12 membered aryl, 5-12 membered heteroaryl, $C_1$-$C_8$ haloalkyl, $C_1$-$C_8$ alkoxy, $C_1$-$C_8$ alkylthio, halogen, hydroxyl, cyano, sulfonic and nitro;

for the above-defined substituents, each of the different substituents R$^a$ or R$^{a'}$ has its own independent definition.

In the present disclosure, the expression $C_{x1}$-$C_{x2}$ is used when referring to some substituent groups, which means that the number of carbon atoms in the substituent groups can be x1 to x2. For example, C0-C8 means that the group contains 0, 1, 2, 3, 4, 5, 6, 7 or 8 carbon atoms, and C1-C8 means that the group contains 1, 2, 3, 4, 5, 6, 7, or 8 carbon atoms, C2-C8 means that the group contains 2, 3, 4, 5, 6, 7 or 8 carbon atoms, and C3-C8 means that the group contains 3, 4, 5, 6, 7, or 8 carbon atoms, C4-C8 means that the group contains 4, 5, 6, 7 or 8 carbon atoms, C1-C6 means that the group contains 1, 2, 3, 4, 5 Or 6 carbon atoms.

In the present disclosure, the expression "x1-x2-membered ring" is used when referring to a cyclic group, which means that the number of ring atoms of the group can be x1 to x2. For example, the 3-12 membered cycloalkyl or heterocycloalkyl group can be a 3, 4, 5, 6, 7, 8, 9, 10, 11 or 12 membered ring, and the number of ring atoms can be 3, 4, 5, 6, 7, 8, 9, 10, 11 or 12; a 3-6 membered ring means that the cyclic group can be a 3, 4, 5 or 6 membered ring, and the number of ring atoms can be 3, 4, 5 or 6; 3-9 membered ring means that the cyclic group can be 3, 4, 5, 6, 7, 8 or 9 membered ring, and the number of ring atoms can be 3, 4, 5, 6, 7, 8 or 9; 5-12 membered ring means that the cyclic group can be a 5, 6, 7, 8, 9, 10, 11 or 12 membered ring, and the number of ring atoms can be 5, 6, 7, 8, 9, 10, 11 or 12. The ring atom may be a carbon atom or a heteroatom, such as a heteroatom selected from N, O, and S. When the ring is a heterocyclic ring, the heterocyclic ring may contain 1, 2, 3, 4, 5, 6, 7, 8, 9, 10 or more ring heteroatoms, for example selected from N, O and S heteroatoms.

In the present disclosure, one or more halogens may each be independently selected from fluorine, chlorine, bromine, and iodine.

In a preferred embodiment of the present invention, $R_1$ and $R_2$, together with the carbon atom directly attached thereto form a saturated or unsaturated 3-6 membered cycloalkyl or heterocycloalkyl group. The said heterocycloalkyl contains at least one heteroatom selected from O, N or S atoms. The said cycloalkyl or heterocycloalkyl group may be optionally substituted by 0, 1, 2, 3 or 4 substituents each independently selected from the following $R^6$ Substitution, where $R^6$ is as defined above.

In a preferred embodiment of the present invention, the ring formed by $R^1$ and $R^2$ and the carbon atom to which they are connected is selected from the following structures:

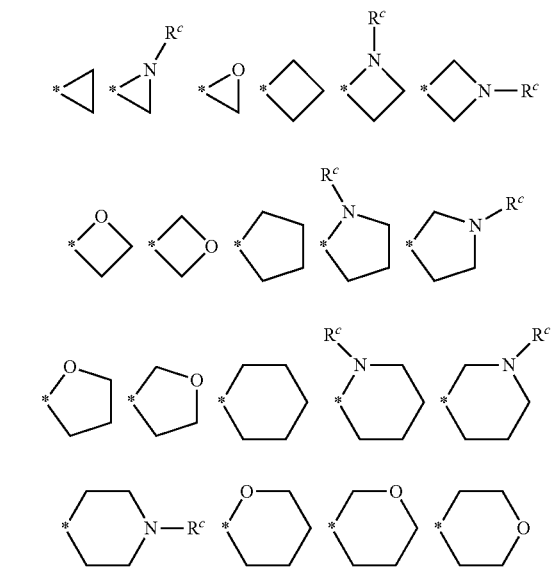

wherein, $R^c$ is selected from hydrogen, $C_1$-$C_6$ alkyl, $C_3$-$C_8$ cycloalkyl, —C(O)R$^a$, —C(O)OR$^a$, —C(O)—NR$^a$R$^{a'}$, —SO$_2$—NR$^a$R$^{a'}$, and —SO$_2$R$^a$;

* represents the binding site of $R^1$ and $R^2$ and the carbon atom connected to them; and the above-mentioned groups may be optionally substituted by 0, 1, 2, 3, 4 substituents independently selected from the following R6 Substitution, wherein R$^a$, R$^{a'}$ and R$^6$ are as defined as above.

In a preferred embodiment of the present invention, X is selected from CR$^a$R$^{a'}$, NR$^a$, O and S, preferably O; wherein, R$^a$ and R$^{a'}$ are selected from hydrogen, $C_1$-$C_8$ alkyl, $C_3$-$C_8$ cycloalkyl, hydroxyl, halogen, $C_1$-$C_8$ haloalkyl, $C_1$-$C_8$ alkylamino, di-($C_1$-$C_8$) alkylamino, or R$^a$, R$^{a'}$ together with the atom directly attached thereto form a 3-9 membered cycloalkyl or heterocycloalkyl ring, preferably hydrogen, halogen or $C_1$-$C_8$ alkyl.

In a preferred embodiment of the present invention, $R^4$ is preferably Cy$^2$, —NHC(O)R$^a$, —C(O)NR$^a$R$^{a'}$ or —NHC(O)NR$^a$R$^{a'}$, wherein Cy$^2$, R$^a$, R$^{a'}$ are defined as above.

In a preferred embodiment of the present invention, Cy$^2$ is selected from phenyl, pyridyl, pyrazinyl, cyclopropyl, cyclopentyl, cyclohexyl, furyl, thiazolyl, piperidinyl, piperazinyl, oxazolyl, imidazolyl and thienyl; more preferably, Cy$^2$ is selected from pyrazolyl, imidazolyl, oxazolyl, thiazolyl, phenyl and pyridyl; and the Cy$^2$ can be optionally substituted by $C_1$-$C_8$ alkyl, $C_1$-$C_8$ alkoxy, $C_3$-$C_9$ cycloalkane Group, $C_3$-$C_9$ heterocyclic group, $C_1$-$C_8$ haloalkyl, halogen, cyano, sulfonic acid, nitro or hydroxy.

In a preferred embodiment of the present invention, R$^a$ and R$^{a'}$ are preferably hydrogen, halogen or $C_1$-$C_8$ alkyl.

In one embodiment of the present invention, wherein the compound of formula I is preferably selected from compounds having the following structure:

| NO. | Structure |
|---|---|
| 1 | 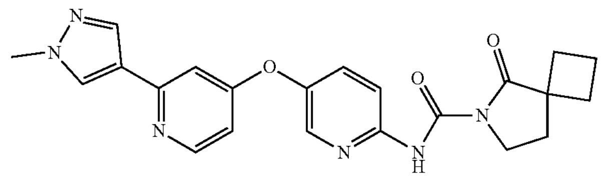 [SMILES: Cn1cc(-c2cc(Oc3ccc(NC(=O)N4CCC5(CCC5)C4=O)nc3)ccn2)cn1] |
| 2 | 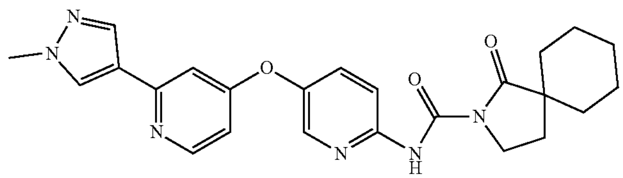 [SMILES: Cn1cc(-c2cc(Oc3ccc(NC(=O)N4CCC5(CCCCC5)C4=O)nc3)ccn2)cn1] |
| 3 | 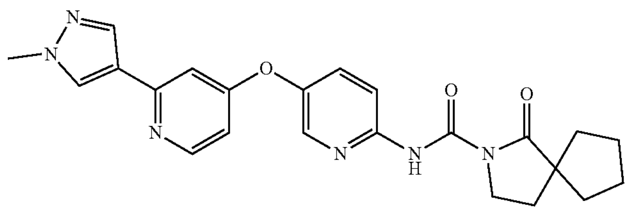 [SMILES: Cn1cc(-c2cc(Oc3ccc(NC(=O)N4CCC5(CCCC5)C4=O)nc3)ccn2)cn1] |
| 4 | 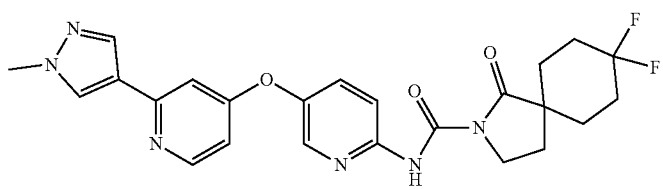 [SMILES: Cn1cc(-c2cc(Oc3ccc(NC(=O)N4CCC5(CCC(F)(F)CC5)C4=O)nc3)ccn2)cn1] |
| 5 | 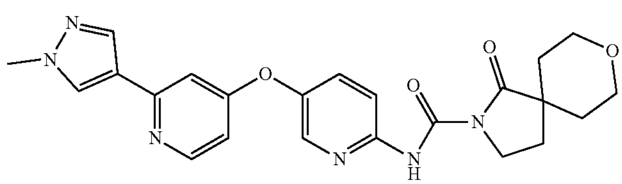 [SMILES: Cn1cc(-c2cc(Oc3ccc(NC(=O)N4CCC5(CCOCC5)C4=O)nc3)ccn2)cn1] |
| 6 | 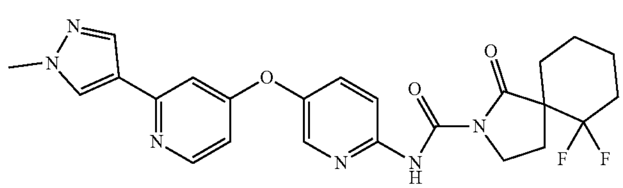 [SMILES: Cn1cc(-c2cc(Oc3ccc(NC(=O)N4CCC5(CCCCC5(F)F)C4=O)nc3)ccn2)cn1] |
| 7 | 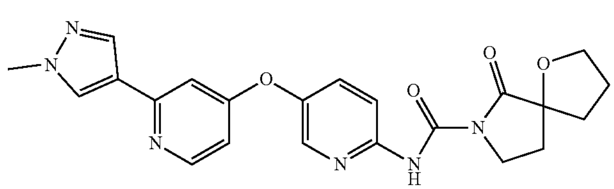 [SMILES: Cn1cc(-c2cc(Oc3ccc(NC(=O)N4CCC5(CCCO5)C4=O)nc3)ccn2)cn1] |
| 8 | 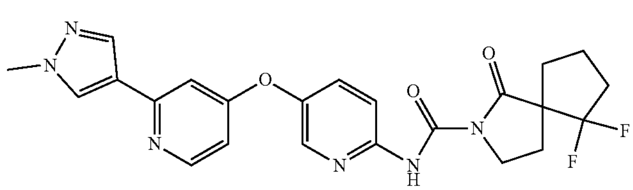 [SMILES: Cn1cc(-c2cc(Oc3ccc(NC(=O)N4CCC5(CCCC5(F)F)C4=O)nc3)ccn2)cn1] |

-continued

| NO. | Structure |
|---|---|
| 9 | 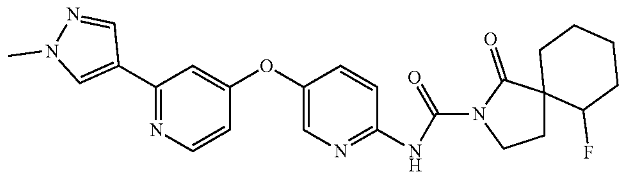 [SMILES: Cn1cc(-c2cc(Oc3ccc(NC(=O)N4CCC5(CCCCC5F)C4=O)nc3)ccn2)cn1] |
| 10 | 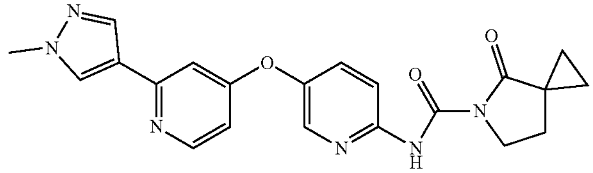 [SMILES: Cn1cc(-c2cc(Oc3ccc(NC(=O)N4CCC5(CC5)C4=O)nc3)ccn2)cn1] |
| 11 | 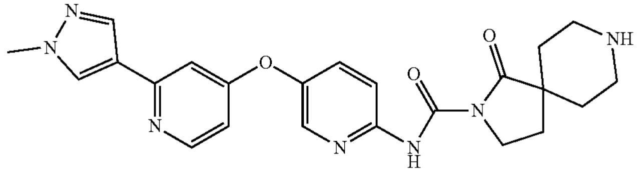 [SMILES: Cn1cc(-c2cc(Oc3ccc(NC(=O)N4CCC5(CCNCC5)C4=O)nc3)ccn2)cn1] |
| 12 | 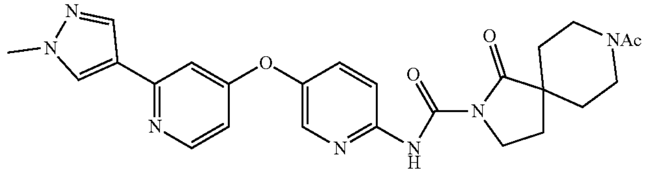 |
| 13 | 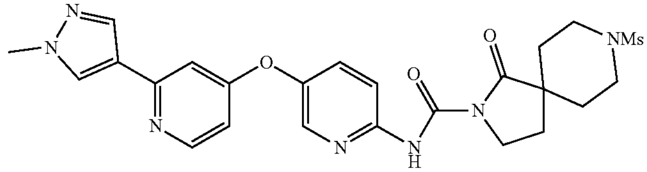 |
| 14 | 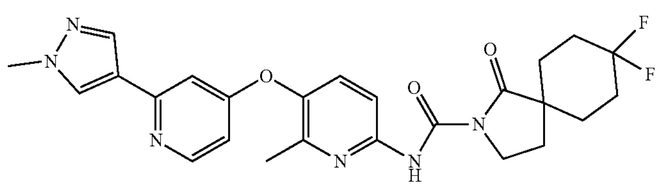 [SMILES: Cc1nc(NC(=O)N2CCC3(CCC(F)(F)CC3)C2=O)ccc1Oc1ccnc(-c2cnn(C)c2)c1] |
| 15 | 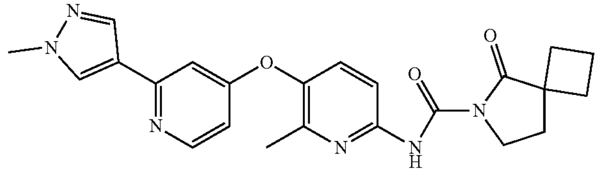 [SMILES: Cc1nc(NC(=O)N2CCC3(CCC3)C2=O)ccc1Oc1ccnc(-c2cnn(C)c2)c1] |
| 16 | 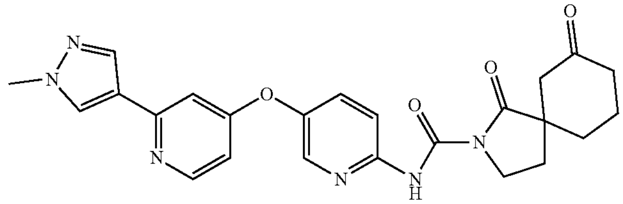 [SMILES: Cn1cc(-c2cc(Oc3ccc(NC(=O)N4CCC5(CCCC(=O)C5)C4=O)nc3)ccn2)cn1] |

-continued
| NO. | Structure |
|---|---|
| 17 | 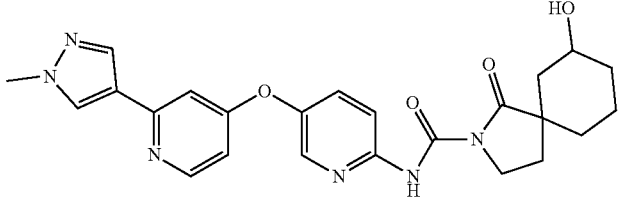 [SMILES: Cn1cc(-c2cc(Oc3ccc(NC(=O)N4CCC5(CCCC(O)C5)C4=O)nc3)ccn2)cn1] |
| 18 | 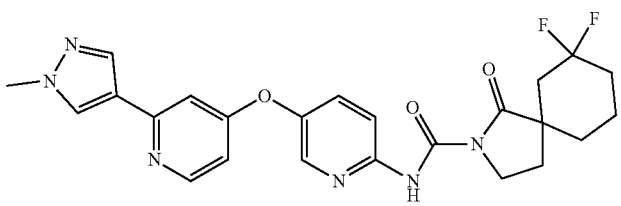 [SMILES: Cn1cc(-c2cc(Oc3ccc(NC(=O)N4CCC5(CCCC(F)(F)C5)C4=O)nc3)ccn2)cn1] |
| 19 | 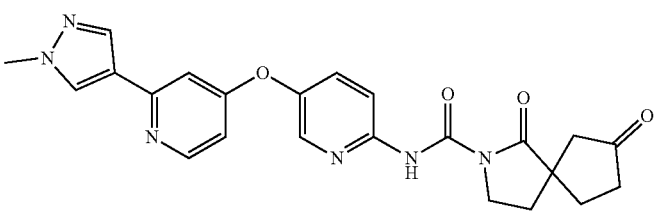 [SMILES: Cn1cc(-c2cc(Oc3ccc(NC(=O)N4CCC5(CCC(=O)C5)C4=O)nc3)ccn2)cn1] |
| 20 | 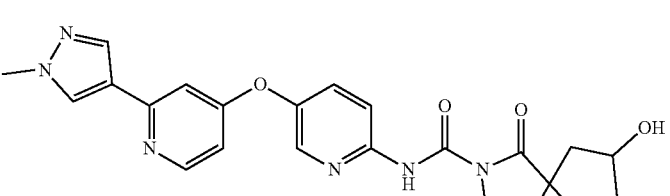 |
| 21 | 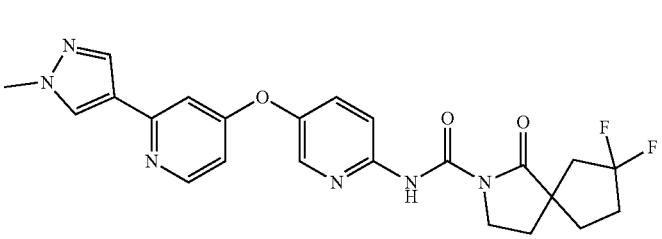 [SMILES: Cn1cc(-c2cc(Oc3ccc(NC(=O)N4CCC5(CCC(F)(F)C5)C4=O)nc3)ccn2)cn1] |
| 22 | 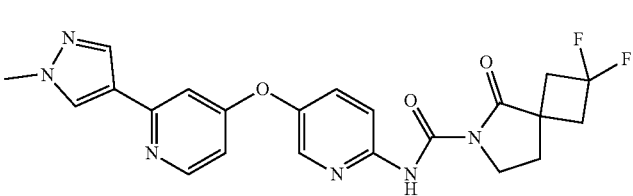 [SMILES: Cn1cc(-c2cc(Oc3ccc(NC(=O)N4CCC5(CC(F)(F)C5)C4=O)nc3)ccn2)cn1] |
| 23 | 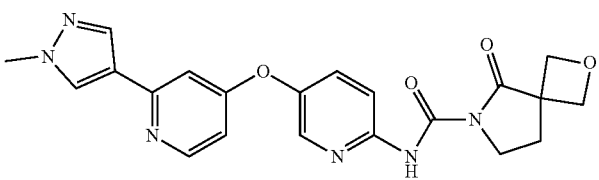 [SMILES: Cn1cc(-c2cc(Oc3ccc(NC(=O)N4CCC5(COC5)C4=O)nc3)ccn2)cn1] |

-continued

| NO. | Structure |
|---|---|
| 24 | 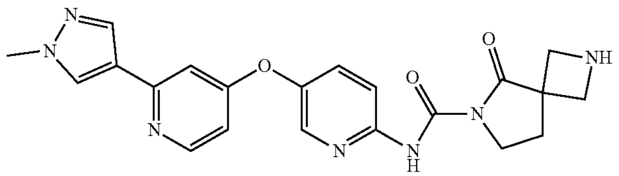 [SMILES: Cn1cc(-c2cc(Oc3ccc(NC(=O)N4CCC5(CNC5)C4=O)nc3)ccn2)cn1] |
| 25 | 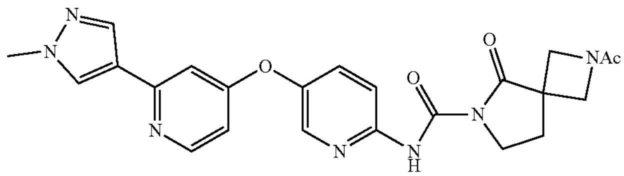 |
| 26 | 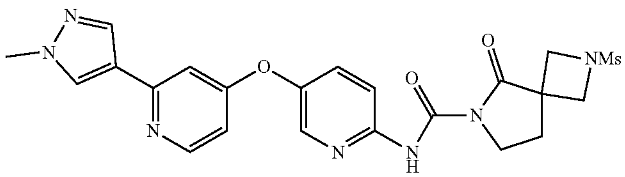 |
| 27 | 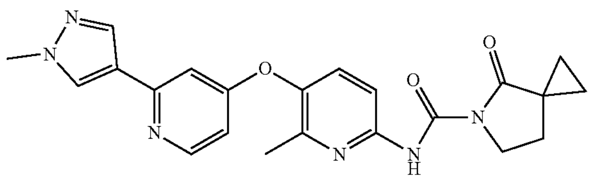 [SMILES: Cc1nc(NC(=O)N2CCC3(CC3)C2=O)ccc1Oc1ccnc(-c2cnn(C)c2)c1] |
| 28 | 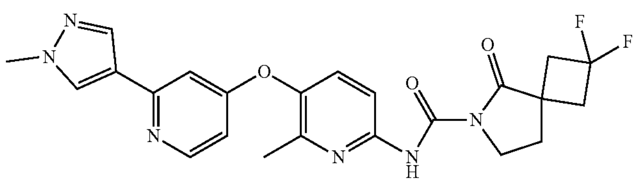 [SMILES: Cc1nc(NC(=O)N2CCC3(CC(F)(F)C3)C2=O)ccc1Oc1ccnc(-c2cnn(C)c2)c1] |
| 29 | 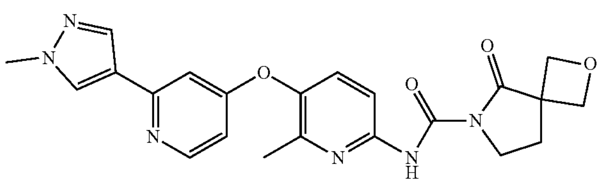 [SMILES: Cc1nc(NC(=O)N2CCC3(COC3)C2=O)ccc1Oc1ccnc(-c2cnn(C)c2)c1] |
| 30 | 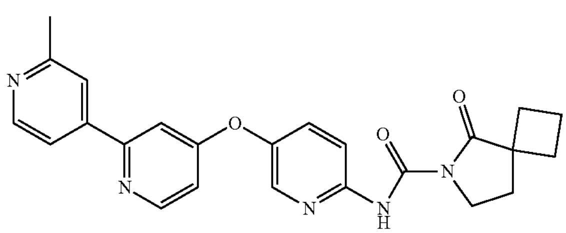 [SMILES: Cc1cc(-c2cc(Oc3ccc(NC(=O)N4CCC5(CCC5)C4=O)nc3)ccn2)ccn1] |
| 31 | 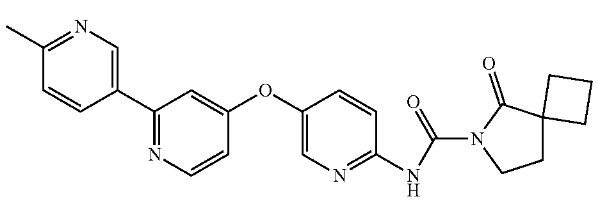 [SMILES: Cc1ccc(-c2cc(Oc3ccc(NC(=O)N4CCC5(CCC5)C4=O)nc3)ccn2)cn1] |

-continued

| NO. | Structure |
|---|---|
| 32 | 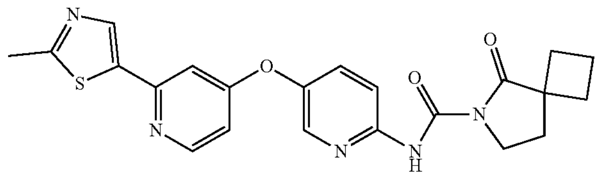 [SMILES: Cc1ncc(-c2cc(Oc3ccc(NC(=O)N4CCC5(CCC5)C4=O)nc3)ccn2)s1] |
| 33 | 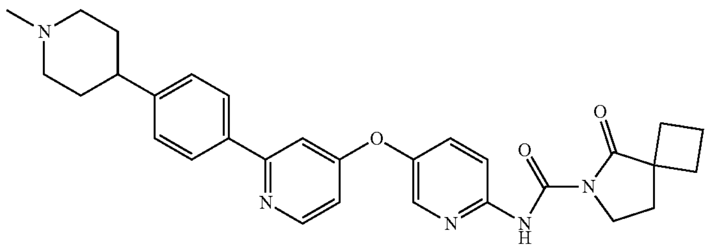 [SMILES: CN1CCC(c2ccc(-c3cc(Oc4ccc(NC(=O)N5CCC6(CCC6)C5=O)nc4)ccn3)cc2)CC1] |
| 34 | 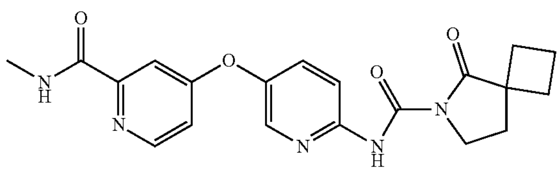 [SMILES: CNC(=O)c1cc(Oc2ccc(NC(=O)N3CCC4(CCC4)C3=O)nc2)ccn1] |
| 35 | 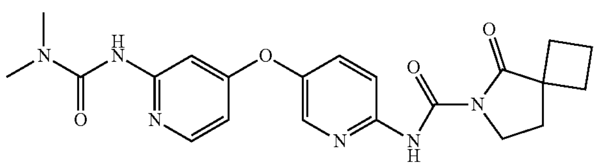 [SMILES: CN(C)C(=O)Nc1cc(Oc2ccc(NC(=O)N3CCC4(CCC4)C3=O)nc2)ccn1] |
| 36 | 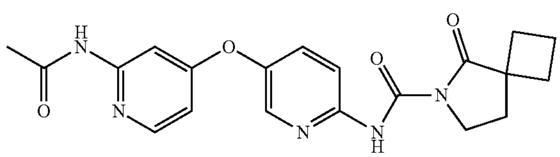 [SMILES: CC(=O)Nc1cc(Oc2ccc(NC(=O)N3CCC4(CCC4)C3=O)nc2)ccn1] |
| 37 | 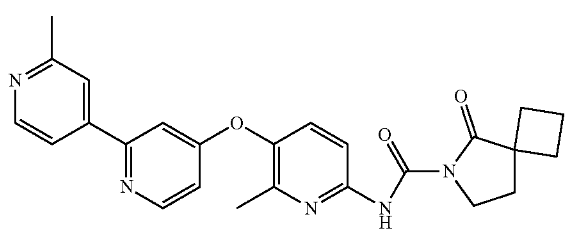 [SMILES: Cc1cc(-c2cc(Oc3ccc(NC(=O)N4CCC5(CCC5)C4=O)nc3C)ccn2)ccn1] |
| 38 | 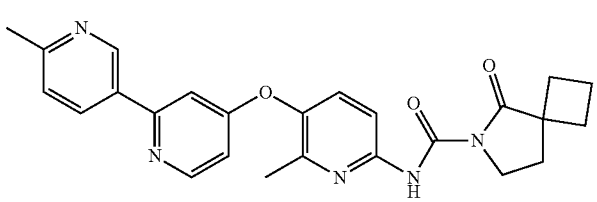 [SMILES: Cc1ccc(-c2cc(Oc3ccc(NC(=O)N4CCC5(CCC5)C4=O)nc3C)ccn2)cn1] |
| 39 | 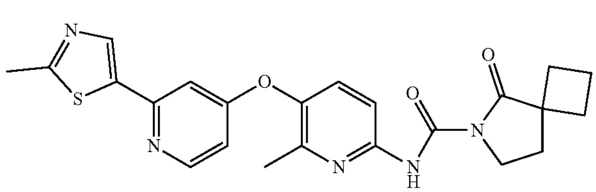 [SMILES: Cc1ncc(-c2cc(Oc3ccc(NC(=O)N4CCC5(CCC5)C4=O)nc3C)ccn2)s1] |

-continued

| NO. | Structure |
|---|---|
| 40 | 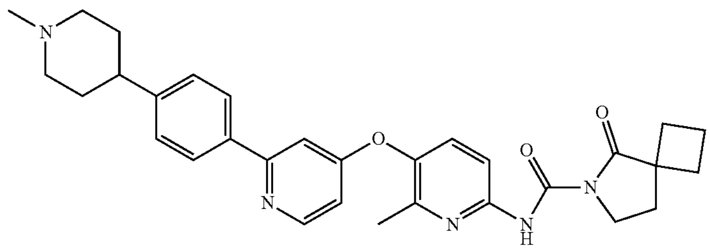 [SMILES: Cc1nc(NC(=O)N2CCC3(CCC3)C2=O)ccc1Oc1ccnc(-c2ccc(C3CCN(C)CC3)cc2)c1] |
| 41 | 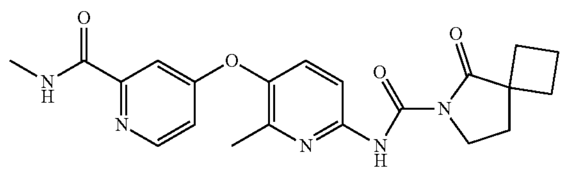 [SMILES: CNC(=O)c1cc(Oc2ccc(NC(=O)N3CCC4(CCC4)C3=O)nc2C)ccn1] |
| 42 | 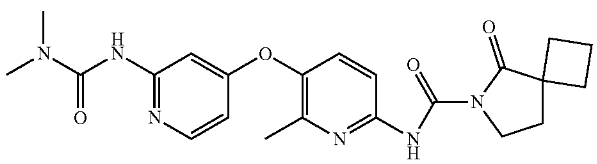 [SMILES: Cc1nc(NC(=O)N2CCC3(CCC3)C2=O)ccc1Oc1ccnc(NC(=O)N(C)C)c1] |
| 43 | 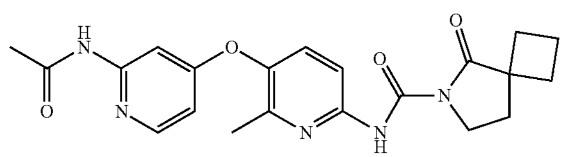 [SMILES: CC(=O)Nc1cc(Oc2ccc(NC(=O)N3CCC4(CCC4)C3=O)nc2C)ccn1] |
| 44 | 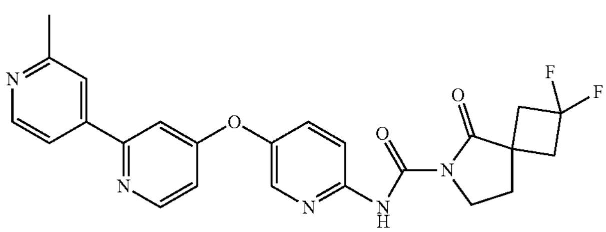 [SMILES: Cc1cc(-c2cc(Oc3ccc(NC(=O)N4CCC5(CC(F)(F)C5)C4=O)nc3)ccn2)ccn1] |
| 45 | 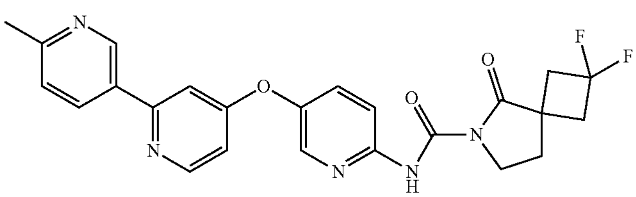 [SMILES: Cc1ccc(-c2cc(Oc3ccc(NC(=O)N4CCC5(CC(F)(F)C5)C4=O)nc3)ccn2)cn1] |
| 46 | 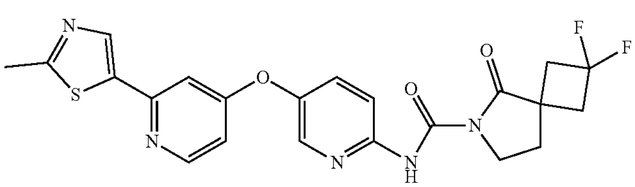 [SMILES: Cc1ncc(-c2cc(Oc3ccc(NC(=O)N4CCC5(CC(F)(F)C5)C4=O)nc3)ccn2)s1] |

-continued

| NO. | Structure |
|---|---|
| 47 | 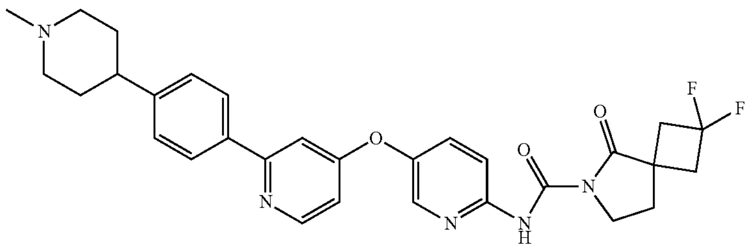 [SMILES: CN1CCC(c2ccc(-c3cc(Oc4ccc(NC(=O)N5CCC6(CC(F)(F)C6)C5=O)nc4)ccn3)cc2)CC1] |
| 48 | 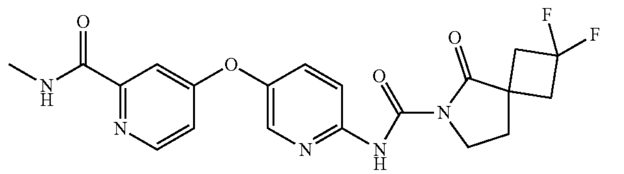 [SMILES: CNC(=O)c1cc(Oc2ccc(NC(=O)N3CCC4(CC(F)(F)C4)C3=O)nc2)ccn1] |
| 49 | 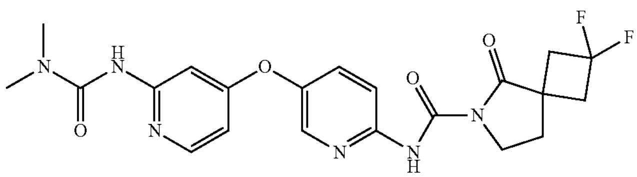 [SMILES: CN(C)C(=O)Nc1cc(Oc2ccc(NC(=O)N3CCC4(CC(F)(F)C4)C3=O)nc2)ccn1] |
| 50 | 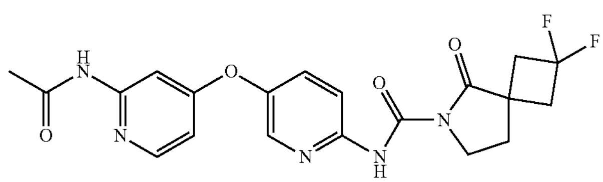 [SMILES: CC(=O)Nc1cc(Oc2ccc(NC(=O)N3CCC4(CC(F)(F)C4)C3=O)nc2)ccn1] |
| 51 | 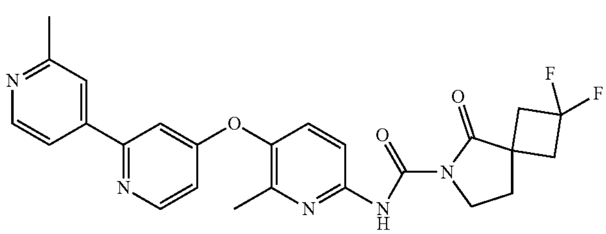 [SMILES: Cc1cc(-c2cc(Oc3ccc(NC(=O)N4CCC5(CC(F)(F)C5)C4=O)nc3C)ccn2)ccn1] |
| 52 | 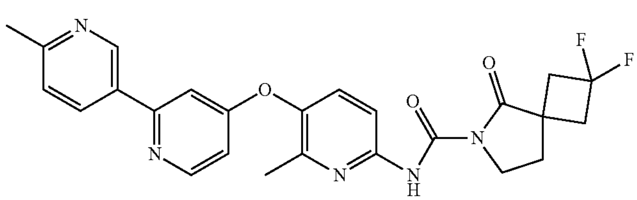 [SMILES: Cc1ccc(-c2cc(Oc3ccc(NC(=O)N4CCC5(CC(F)(F)C5)C4=O)nc3C)ccn2)cn1] |
| 53 | 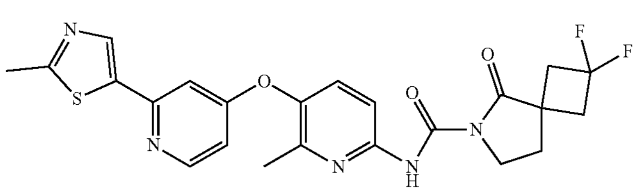 [SMILES: Cc1ncc(-c2cc(Oc3ccc(NC(=O)N4CCC5(CC(F)(F)C5)C4=O)nc3C)ccn2)s1] |

-continued
| NO. | Structure |
|---|---|
| 54 | 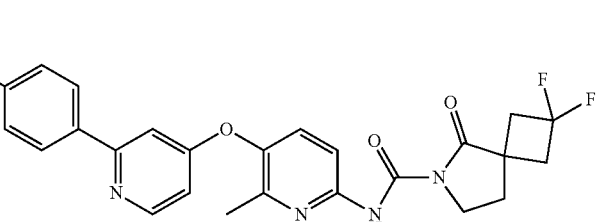 |
| 55 | 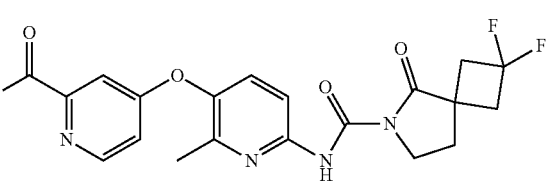 |
| 56 | 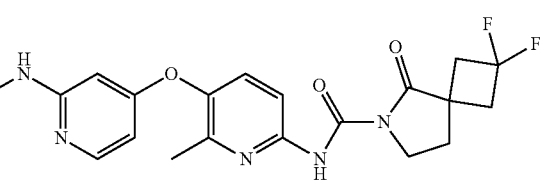 |
| 57 | 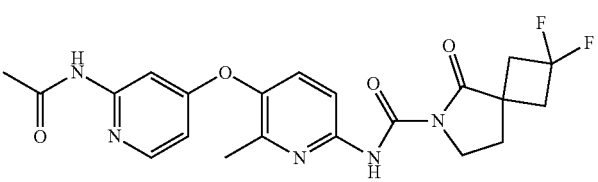 [SMILES: CC(=O)Nc1cc(Oc2ccc(NC(=O)N3CCC4(CC(F)(F)C4)C3=O)nc2C)ccn1] |
| 58 | 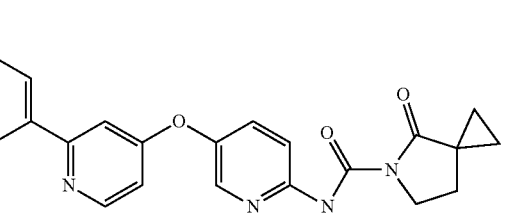 |
| 59 | 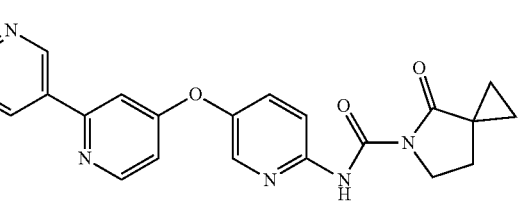 |
| 60 | 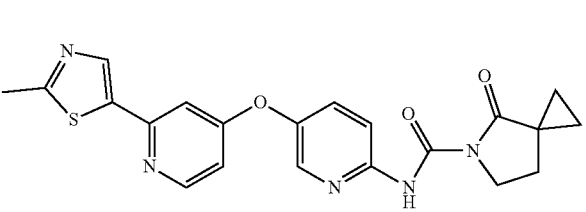 [SMILES: Cc1ncc(-c2cc(Oc3ccc(NC(=O)N4CCC5(CC5)C4=O)nc3)ccn2)s1] |

-continued

| NO. | Structure |
|---|---|
| 61 | 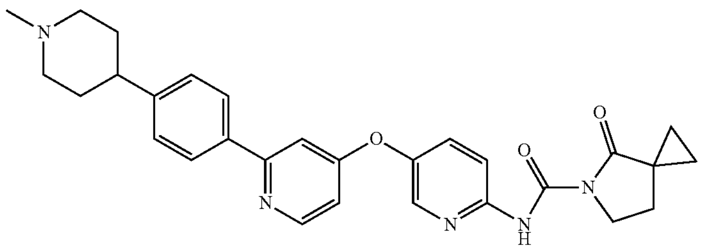 [SMILES: CN1CCC(c2ccc(-c3cc(Oc4ccc(NC(=O)N5CCC6(CC6)C5=O)nc4)ccn3)cc2)CC1] |
| 62 | 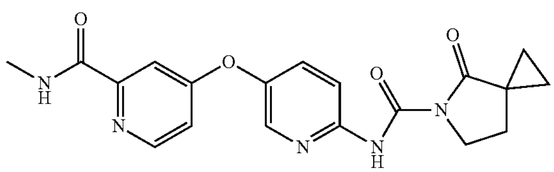 [SMILES: CNC(=O)c1cc(Oc2ccc(NC(=O)N3CCC4(CC4)C3=O)nc2)ccn1] |
| 63 | 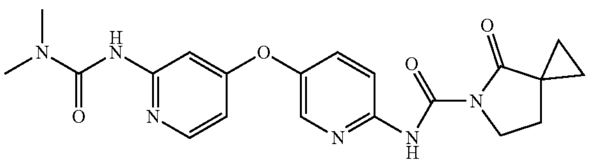 [SMILES: CN(C)C(=O)Nc1cc(Oc2ccc(NC(=O)N3CCC4(CC4)C3=O)nc2)ccn1] |
| 64 | 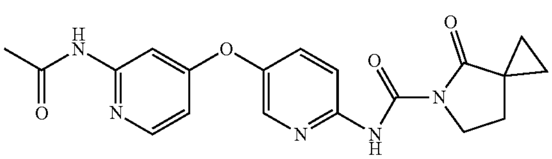 [SMILES: CC(=O)Nc1cc(Oc2ccc(NC(=O)N3CCC4(CC4)C3=O)nc2)ccn1] |
| 65 | 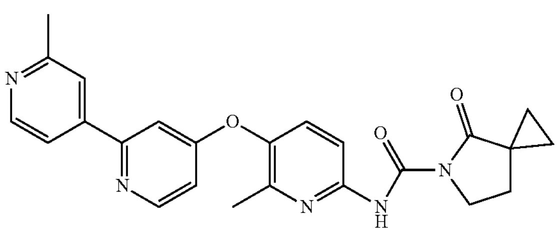 [SMILES: Cc1cc(-c2cc(Oc3ccc(NC(=O)N4CCC5(CC5)C4=O)nc3C)ccn2)ccn1] |
| 66 | 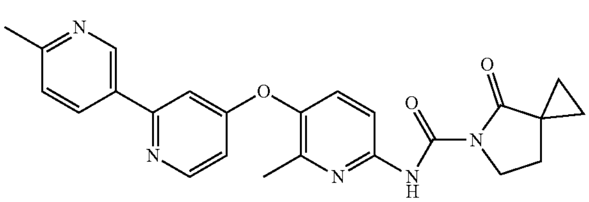 [SMILES: Cc1ccc(-c2cc(Oc3ccc(NC(=O)N4CCC5(CC5)C4=O)nc3C)ccn2)cn1] |
| 67 | 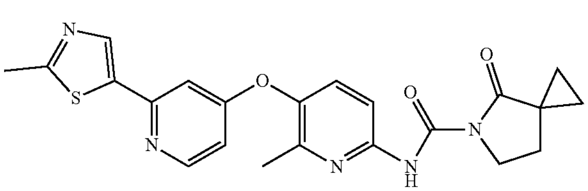 [SMILES: Cc1ncc(-c2cc(Oc3ccc(NC(=O)N4CCC5(CC5)C4=O)nc3C)ccn2)s1] |

-continued

| NO. | Structure |
|---|---|
| 68 | 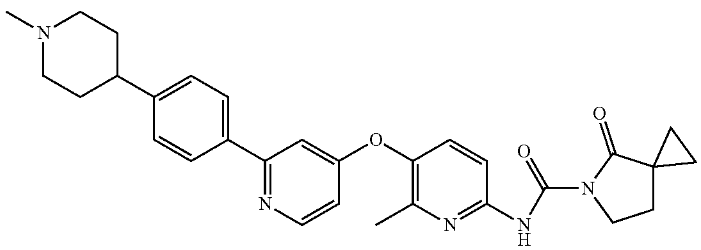 [SMILES: Cc1nc(NC(=O)N2CCC3(CC3)C2=O)ccc1Oc1ccnc(-c2ccc(C3CCN(C)CC3)cc2)c1] |
| 69 | 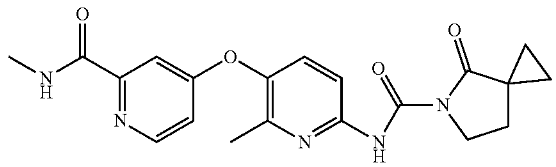 [SMILES: CNC(=O)c1cc(Oc2ccc(NC(=O)N3CCC4(CC4)C3=O)nc2C)ccn1] |
| 70 | 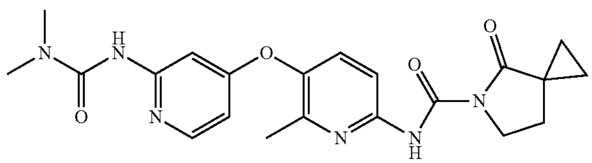 [SMILES: Cc1nc(NC(=O)N2CCC3(CC3)C2=O)ccc1Oc1ccnc(NC(=O)N(C)C)c1] |
| 71 | 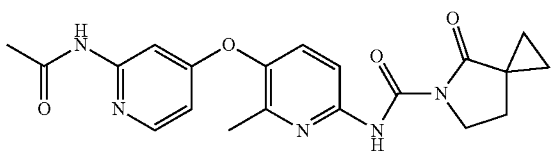 [SMILES: CC(=O)Nc1cc(Oc2ccc(NC(=O)N3CCC4(CC4)C3=O)nc2C)ccn1] |
| 72 | 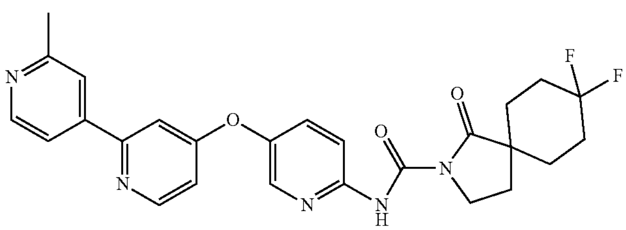 [SMILES: Cc1cc(-c2cc(Oc3ccc(NC(=O)N4CCC5(CCC(F)(F)CC5)C4=O)nc3)ccn2)ccn1] |
| 73 | 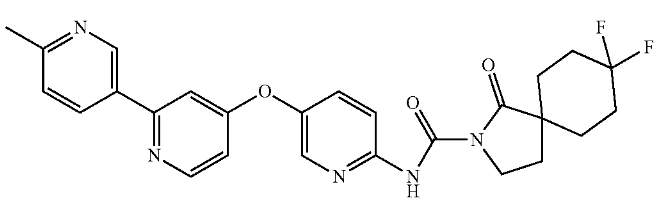 [SMILES: Cc1ccc(-c2cc(Oc3ccc(NC(=O)N4CCC5(CCC(F)(F)CC5)C4=O)nc3)ccn2)cn1] |
| 74 | 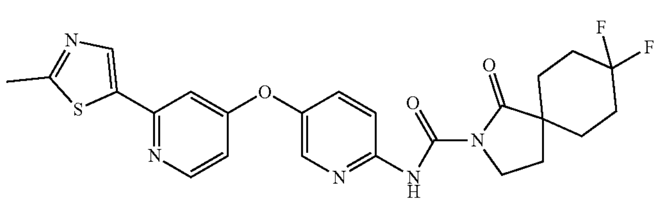 [SMILES: Cc1ncc(-c2cc(Oc3ccc(NC(=O)N4CCC5(CCC(F)(F)CC5)C4=O)nc3)ccn2)s1] |

-continued

| NO. | Structure |
| --- | --- |
| 75 | 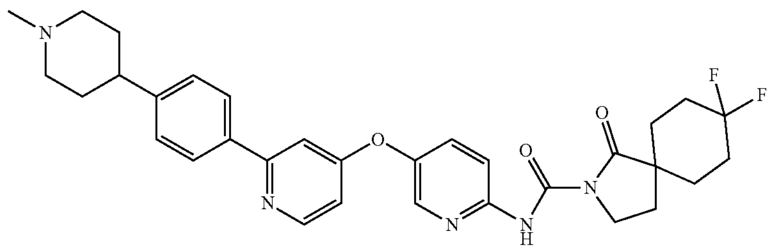 [SMILES: CN1CCC(c2ccc(-c3cc(Oc4ccc(NC(=O)N5CCC6(CCC(F)(F)CC6)C5=O)nc4)ccn3)cc2)CC1] |
| 76 | 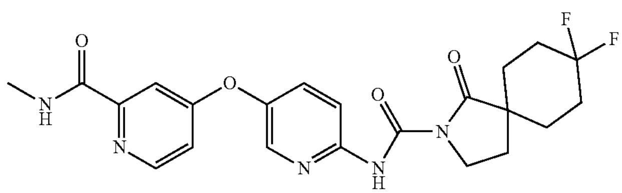 [SMILES: CNC(=O)c1cc(Oc2ccc(NC(=O)N3CCC4(CCC(F)(F)CC4)C3=O)nc2)ccn1] |
| 77 | 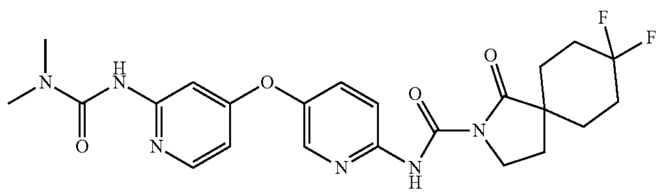 [SMILES: CN(C)C(=O)Nc1cc(Oc2ccc(NC(=O)N3CCC4(CCC(F)(F)CC4)C3=O)nc2)ccn1] |
| 78 | 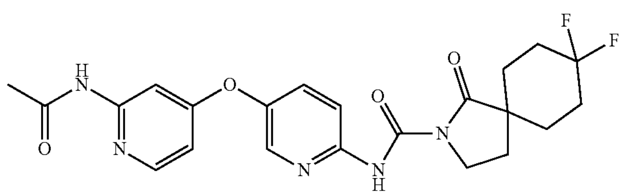 [SMILES: CC(=O)Nc1cc(Oc2ccc(NC(=O)N3CCC4(CCC(F)(F)CC4)C3=O)nc2)ccn1] |
| 79 | 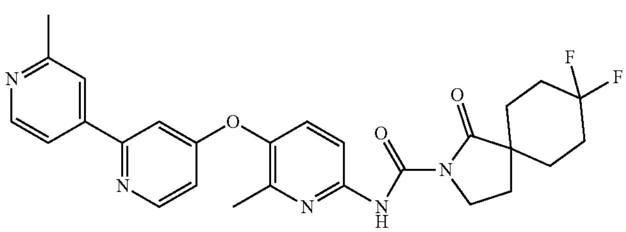 [SMILES: Cc1cc(-c2cc(Oc3ccc(NC(=O)N4CCC5(CCC(F)(F)CC5)C4=O)nc3C)ccn2)ccn1] |
| 80 | 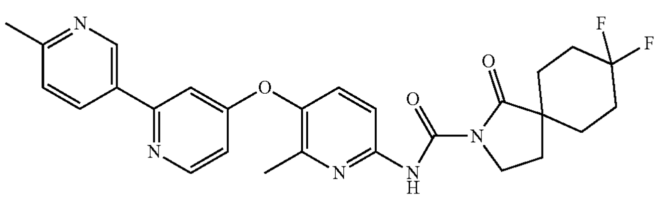 [SMILES: Cc1ccc(-c2cc(Oc3ccc(NC(=O)N4CCC5(CCC(F)(F)CC5)C4=O)nc3C)ccn2)cn1] |
| 81 | 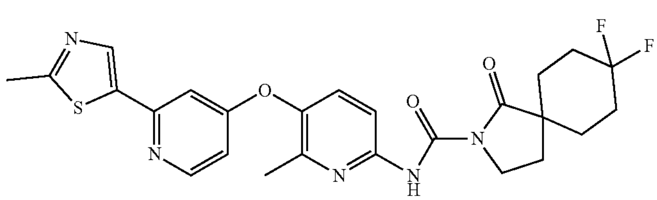 [SMILES: Cc1ncc(-c2cc(Oc3ccc(NC(=O)N4CCC5(CCC(F)(F)CC5)C4=O)nc3C)ccn2)s1] |

-continued

| NO. | Structure |
|---|---|
| 82 | 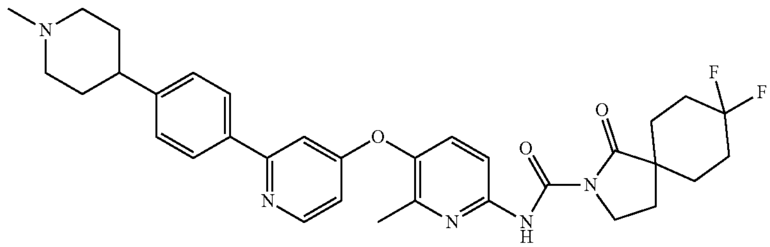 [SMILES: Cc1nc(NC(=O)N2CCC3(CCC(F)(F)CC3)C2=O)ccc1Oc1ccnc(-c2ccc(C3CCN(C)CC3)cc2)c1] |
| 83 | 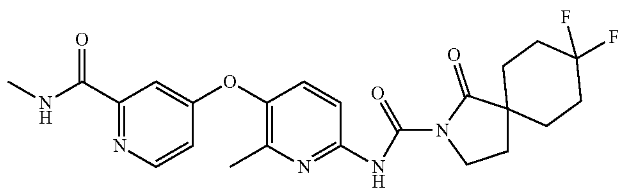 [SMILES: CNC(=O)c1cc(Oc2ccc(NC(=O)N3CCC4(CCC(F)(F)CC4)C3=O)nc2C)ccn1] |
| 84 | 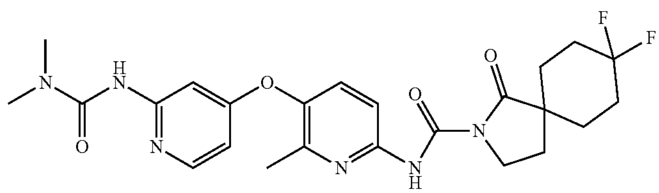 [SMILES: Cc1nc(NC(=O)N2CCC3(CCC(F)(F)CC3)C2=O)ccc1Oc1ccnc(NC(=O)N(C)C)c1] |
| 85 | 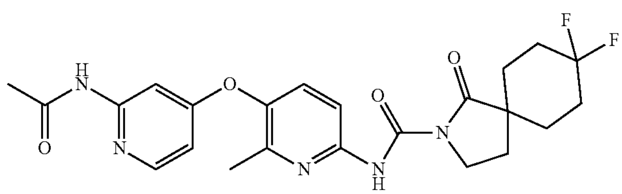 [SMILES: CC(=O)Nc1cc(Oc2ccc(NC(=O)N3CCC4(CCC(F)(F)CC4)C3=O)nc2C)ccn1] |
| 86 | 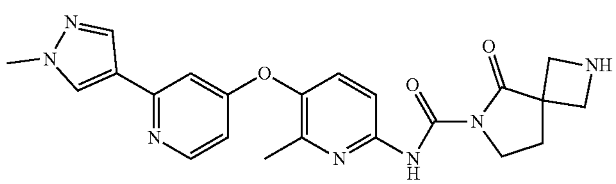 [SMILES: Cc1nc(NC(=O)N2CCC3(CNC3)C2=O)ccc1Oc1ccnc(-c2cnn(C)c2)c1] |
| 87 | 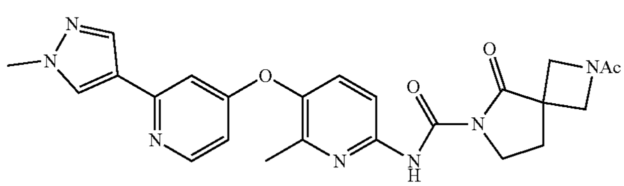 |
| 88 | 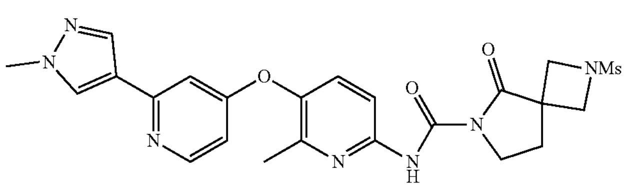 |
| 89 | 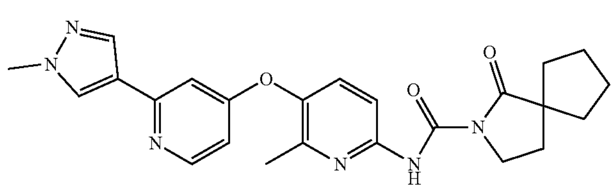 [SMILES: Cc1nc(NC(=O)N2CCC3(CCCC3)C2=O)ccc1Oc1ccnc(-c2cnn(C)c2)c1] |

| NO. | Structure |
|---|---|
| 90 | (structure shown) |

The compounds of the present invention can also be prepared in the form of pharmaceutically acceptable salts, which can be formed by using, for example, the following inorganic or organic acids: hydrochloric acid, hydrobromic acid, sulfuric acid, phosphoric acid, nitric acid, acetic acid, glycolic acid, Lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxyl Benzoic acid, phenylacetic acid, cinnamic acid, salicylic acid, methanesulfonic acid, benzenesulfonic acid or toluenesulfonic acid.

The pharmaceutically acceptable salt of the present invention can be prepared by conventional methods, for example, by dissolving the compound of the present invention in a water-miscible organic solvent (such as acetone, methanol, ethanol, and acetonitrile), and adding excess organic acid or inorganic acid to it. An aqueous acid solution is used to precipitate the salt from the resulting mixture, the solvent and remaining free acid are removed therefrom, and then the precipitated salt is separated.

The compound of the present invention or a pharmaceutically acceptable salt thereof may include hydrates and solvates thereof.

The present invention also provides the use of the compounds of the present invention in the preparation of drugs for the prevention and/or treatment of cancer, tumors, inflammatory diseases, autoimmune diseases or immune-mediated diseases.

In addition, the present invention provides a pharmaceutical composition for preventing and/or treating cancer, tumor, inflammatory disease, autoimmune disease, neurodegenerative disease, attention-related disease or immune-mediated disease, which The compound of the present invention is included as an active ingredient.

The present invention also provides a method for inhibiting CSF1R, which comprises exposing the compound of the present invention or a pharmaceutically acceptable salt thereof or a pharmaceutical composition comprising the compound of the present invention or a pharmaceutically acceptable salt thereof to the CSF1R.

The present invention also provides a method for preventing and/or treating diseases that can be prevented and/or treated by inhibiting CSF1R, which comprises administering the compound of the present invention or a pharmaceutically acceptable salt thereof to a subject in need thereof, or a pharmaceutical composition of the compound of the present invention or a pharmaceutically acceptable salt thereof.

In addition, the present invention provides a method for preventing and/or treating cancer, tumors, inflammatory diseases, autoimmune diseases, neurodegenerative diseases, attention-related diseases or immune-mediated diseases, which includes administering the compound of the invention to a mammal in need thereof.

Representative examples of the inflammatory diseases, autoimmune diseases and immunologically mediated diseases include, but are not limited to, arthritis, rheumatoid arthritis, spondyloarthropathy, gouty arthritis, osteoarthritis, juvenile arthritis, other arthritic condition, lupus, systemic lupus erythematosus (SLE), skin-related disease, psoriasis, eczema, dermatitis, atopic dermatitis, pain, pulmonary disorder, lung inflammation, adult respiratoty distress syndrome (ARDS), pulmonary sarcoidosis, chronic pulmonary inflammatory disease, chronic obstructive pulmonary disease (COPD), cardiovascular disease, artherosclerosis, myocardial infarction, congestive heart failure, cardiac reperfusion injury, inflammatory bowl disease, Crohn's disease, ulcerative colitis, irritable bowl syndrome, asthma, sjogren syndrome, autoimmunity thyroid disease, urticaria (enidosis), multiple sclerosis, scleroderma, organ transplantation rejection, heteroplastic graft, idiopathic thrombocytopenic purpura (ITP), Parkinson's disease, Alzheimer's disease, diabetic associated disease, inflammation, pelvic inflammatory disease, allergic rhinitis, allergic bronchitis, allergic sinusitis, leukemia, lymphoma, B-cell lymphoma, T-cell lymphoma, myeloma, acute lymphoid leukemia (ALL), chronic lymphoid leukemia (CLL), acute myeloid leukemia (AML), chronic myeloid leukemia (CML), hairy cell leukemia, Hodgkin's disease, non-Hodgkin's lymphoma, multiple myeloma, myelodysplastic syndrome (MDS), myeloproliferative neoplasms (MPN), diffuse large B-cell lymphoma, and follicular lymphoma.

Representative examples of the tumor or cancers include, but are not limited to, skin cancer, bladder cancer, Ovarian cancer, breast cancer; gastric carcinoma, pancreatic cancer; prostatic cancer, colorectal carcinoma, Lung Cancer, bone cancer, brain cancer, Neurocytoma, rectal cancer, colon cancer, familial adenomatous polyposis, hereditary nonpolyposis colorectal cancer, esophageal carcinoma, lip cancer, laryngocar, hypopharyngeal carcinoma, tongue cancer, salivary gland carcinoma, gastric carcinoma, adenocarcinoma, medullary thyroid carcinoma, papillary thyroid cancer, kidney cancer, carcinoma of renal pelvis, Ovarian Carcinoma, cervical carcinoma, carcinoma of the corpus uteri, endometrial carcinoma, choriocarcinoma, prostatic cancer, pancreatic cancer, testicular cancer, Urinary cancer, melanoma, Brain tumors such as glioblastoma and astrocytoma, meningeoma, Neuroblastoma and peripheral neuroectodermal tumor, Hodgkin's lymphoma, Non Hodgkin's lymphoma, Burkitt's lymphoma, acute lymphoid leukemia, Acute lymphoblastic leukemia (ALL), Chronic Lymphocytic Leukemia (CLL), Acute myeloid leukemia (AML), Chronic myelogenous leukemia (CML), Adult T-cell leukemia lymphoma, Diffuse large B cell lymphoma (DLBCL), hepatic cellular cancer, gallbladder cancer, bronchogenic carcinoma, small-cell lung carcinoma, non-small-cell lung cancer, multiple myeloma, Basaloma, Teratoma, retinoblastoma, choroidal melanoma, seminoma, rhabdomyosarcoma, craniopharyngioma, osteosarcoma, chondrosarcoma, myosarcoma, liposarcoma, fibrosarcoma, Ewing's sarcoma, plasmacytoma.

When the compound of the present invention or a pharmaceutically acceptable salt thereof is administered in combination with another anticancer agent or immune checkpoint inhibitor for the treatment of cancer or tumor, the compound of the present invention or a pharmaceutically acceptable salt thereof can provide enhanced anti-cancer effect.

Representative examples of anticancer agents for the treatment of cancer or tumors include, but are not limited to, cell signal transduction inhibitors chlorambucil, melphalan, cyclophosphamide, ifosfamide, busulfan, carmustine, lomustine, streptozotocin, cisplatin, carboplatin, oxaliplatin, Dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, Topotecan, irinotecan, etoposide, trabectedin, probiotic, doxorubicin, epirubicin, daunorubicin, mitoxantrone, bleomycin, mitomycin C, ixabepilone, tamoxifen, flutamide, gonadorelin analogs, megestrol, prednisone, dexamethasone, methylprednisolone, thalidomide, interferona, alcium Folinate, sirolimus, sirolimus lipid, everolimus, afatinib, alisertib, amuvatinib, apatinib, axitinib, bortezomib, bosutinib, Brivanib, Carbotinib, Cediranib, crenolanib, crizotinib, Dabrafenib, Dacomitinib, danusertib, dasatinib, dovitinib, Erlotinib, foretinib, ganetespib, gefitinib, ibrutinib, icotinib, imatinib, iniparib, lapatinib, lenvatinib, linifanib, linsitinib, masitinib, momelotinib, Motesanib, lenatinib, nilotinib, niraparib, oprozomib, olaparib, pazopanib, pictilisib, ponatinib, quizartinib, Regorafenib, rigosertib, rucaparib, ruxolitinib, saracatinib, saridegib, sorafenib, sunitinib, tilatinib, tivantinib, Tivozanib, tofacitinib, trametinib, vandetanib, Veliparib, Vemurafenib, Vismodegib, Volasertib, Alemtuzumab, Bevacizumab, brentuximab vedotin, Victorin, Catumaxomab, Cetuximab, Denosumab, Getuzumab, ipilimumab, nimotuzumab, ofatumumab, panitumumab, rituximab, Tositumomab, trastuzumab, IDO inhibitor, anti-PD-1 antibody, anti-PD-L1 antibody, LAG3 antibody, TIM-3 antibody and anti-CTLA-4 antibody or any combination of them.

The inventive compound of formula (I) or a pharmaceutically acceptable salt thereof can provide enhanced therapeutic effects when it is administered in combination with another therapeutic agent for treating inflammatory diseases, autoimmune diseases, or immunologically mediated diseases.

Representative examples of the therapeutic agent for treating the inflammatory diseases, autoimmune diseases, or immunologically mediated diseases include, but are not limited to, steroid drugs (e.g., prednisone, prednisolone, methyl prednisolone, cortisone, hydroxycortisone, betametasone, dexametasone and the like), methotrexates, leflunomides, anti-TNFα agents (e.g., etanercept, infliximab, adalimunab and the like), calcineurin inhibitors (e.g., tacrolimus, pimecrolimus and the like) and antihistaminic drugs (e.g., diphenhydramine, hydroxyzine, loratadine, ebastine, ketotifen, cetirizine, levocetirizine, fexofenadine and the like), and at least one therapeutic agent selected therefrom may be included in the inventive pharmaceutical composition.

The inventive compound or a pharmaceutically acceptable salt thereof may be administered orally or parenterally as an active ingredient in an effective amount ranging from about 0.1 to 2,000 mg/kg, preferably 1 to 1,000 mg/kg body weight per a day in case of mammals including human (of approximately 70 kg body weight) in a single to 4 divided doses per a day, or on/off schedules. The dosage of the active ingredient may be adjusted in light of various relevant factors such as the condition of the subject to be treated, type and seriousness of illness, administration rate, and opinion of doctor. In certain cases, an amount less than the above dosage may be suitable. An amount greater than the above dosage may be used unless it causes deleterious side effects and such amount can be administered in divided doses per day.

The inventive pharmaceutical composition may be formulated in accordance with any of the conventional methods in the form of tablet, granule, powder, capsule, syrup, emulsion or microemulsion for oral administration, or for parenteral administration including intramuscular, intravenous and subcutaneous routes.

The inventive pharmaceutical composition for oral administration may be prepared by mixing the active ingredient with a carrier such as cellulose, calcium silicate, corn starch, lactose, sucrose, dextrose, calcium phosphate, stearic acid, magnesium stearate, calcium stearate, gelatin, talc, surfactant, suspension agent, emulsifier and diluent. Examples of the carrier employed in the injectable composition of the present invention are water, a saline solution, a glucose solution, a glucose-like solution, alcohol, glycol, ether (e.g., polyethylene glycol 400), oil, fatty acid, fatty acid ester, glyceride, a surfactant, a suspension agent and an emulsifier.

In the process of describing exemplary embodiments of the present invention, other features of the present invention will become apparent. The embodiments are given to illustrate the present invention and are not intended to be limitations. The following examples are prepared using the method disclosed in the present invention, separation and characterization.

The compounds of the present invention can be prepared in a variety of ways known to those skilled in the art of organic synthesis. The following methods and synthetic methods known in the field of organic synthetic chemistry can be used to prepare the compounds of the present invention. Synthesis of compounds of the invention. Preferred methods include but are not limited to those described below. The reaction is carried out in a solvent or solvent mixture suitable for the kit materials used and suitable for the transformation achieved. Those skilled in the art of organic synthesis will understand that the functionality present on the molecule is consistent with the proposed transformation. This sometimes requires judgment to change the sequence of synthesis steps or raw materials to obtain the desired compound of the present invention.

DETAILED DESCRIPTION

Terms

Figure 1:
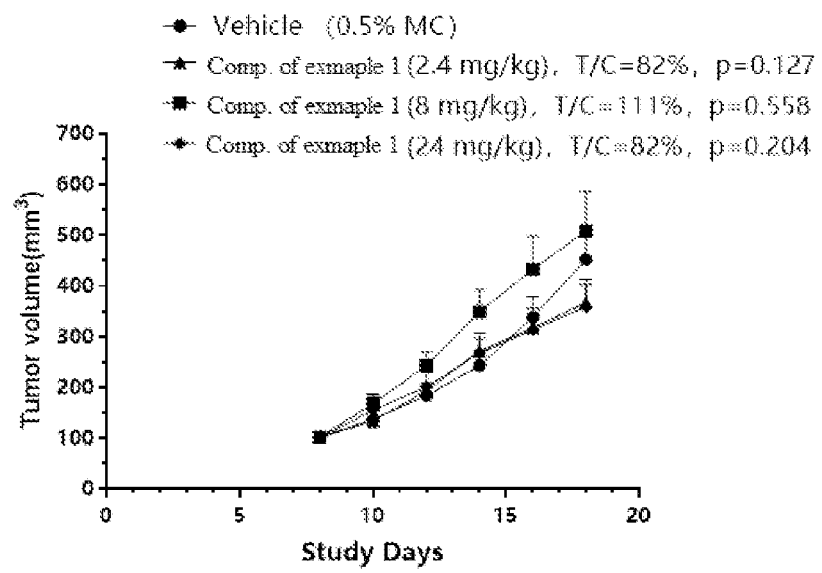
FIG. 1 shows the efficacy results of the compound of Example 1.

Unless otherwise stated, the terms used in the present application, including the specification and claims, are defined as follows. It must be noted that in the specification and appended claims, if does not clearly indicate otherwise, the singular form "a" includes the plural meaning. If not otherwise specified, conventional methods of mass spectrometry, nuclear magnetism, HPLC, protein chemistry, biochemistry, recombinant DNA technology and pharmacology are used. In this application, the use of "or" or "and" means "and/or" unless otherwise stated.

In the specification and claims, the given chemical formula or name shall cover all stereo and optical isomers and racemates in which the above isomers exist. Unless otherwise indicated, all chiral (enantiomers and diastereomers) and racemic forms are within the scope of the present invention. Many geometric isomers such as C=C double bonds, C=N double bonds, ring systems, etc. may also exist in the compound, and all the above stable isomers are encompassed in the present invention. The present invention describes the cis- and trans- (or E- and Z-) geometric isomers of the compounds of the present invention, and they can be separated into a mixture of isomers or separate isomer forms. The compounds of the present invention can be isolated in optically active or racemic form. All methods used to prepare the compounds of the invention and the intermediates prepared therein are considered part of the invention. In the preparation of enantiomeric or diastereomeric products, they can be separated by conventional methods (for example, by chromatography or fractional crystallization). Depending on the process conditions, the final product of the invention is obtained in free (neutral) or salt form. The free forms and salts of these end products are within the scope of the present invention. If desired, one form of the compound can be converted into another form. The free base or acid can be converted into a salt; the salt can be converted into a free compound or another salt; the mixture of isomer compounds of the present invention can be separated into individual isomers. The compounds of the present invention, their free forms and salts can exist in a variety of tautomeric forms, in which hydrogen atoms are transposed to other parts of the molecule and the chemical bonds between the atoms of the molecule are thus rearranged. It should be understood that all tautomeric forms that may exist are included in the present invention.

Unless otherwise defined, the definitions of the substituents of the present invention are independent and not related to each other. For example, for the substituents $R^a$ (or $R^{a'}$), they are independent in the definition of different substituents. Specifically, when a definition of $R^a$ (or $R^{a'}$) is selected in a substituent group, it does not mean that $R^a$ (or $R^{a'}$) has the same definition in other substituents. More specifically, for example (only a non-exhaustive list) for $NR^aR^{a'}$, when the definition of $R^a$ (or $R^{a'}$) is selected from hydrogen, it does not mean that in —C(O)—$NR^aR^{a'}$, $R^a$(or $R^{a'}$) must be hydrogen.

Unless otherwise defined, when a substituent is marked as "optionally substituted", the substituent is selected from, for example, the following substituents such as alkyl, cycloalkyl, aryl, heterocyclyl, halogen, hydroxy, alkoxy, oxo, alkanoyl, aryloxy, alkanoyloxy, amino, alkylamino, arylamino, arylalkylamino, disubstituted amine groups (two of the amino substituents are selected from alkyl, aryl or arylalkyl), alkanoylamino, aroylamino, aralkanoylamino, substituted alkanoylamino, substituted arylamino, substituted aralkanoylamino, thio, alkyl Thio, arylthio, arylalkylthio, arylthiocarbonyl, arylalkylthiocarbonyl, alkylsulfonyl, arylsulfonyl, arylalkylsulfonyl, sulfonylamino such as —SO$_2$NH$_2$, Substituted sulfonylamino, nitro, cyano, carboxy, carbamoyl such as —CONH$_2$, substituted carbamoyl such as —CONH alkyl, —CONH aryl, —CONH arylalkyl or having two groups on the nitrogen In the case of a substituent selected from alkyl, aryl or arylalkyl, alkoxycarbonyl, aryl, substituted aryl, guanidyl, heterocyclic group, such as indolyl, imidazolyl, furyl, thienyl, thiazolyl, pyrrolidinyl, pyridinyl, pyrimidinyl, pyrrolidinyl, piperidinyl, morpholinyl, piperazinyl, homopiperazinyl, etc. and substituted heterocyclic groups.

The term "alkyl" or "alkylene" as used herein is intended to include branched and straight chain saturated aliphatic hydrocarbon groups having the specified number of carbon atoms. For example, "$C_1$-$C_6$ alkyl" means an alkyl group having 1 to 6 carbon atoms. Examples of alkyl groups include, but are not limited to, methyl (Me), ethyl (Et), propyl (e.g., n-propyl and isopropyl), butyl (e.g., n-butyl, isobutyl, tert-butyl) and Pentyl (e.g., n-pentyl, isopentyl, neopentyl).

The term "alkenyl" refers to a straight or branched hydrocarbon group containing one or more double bonds and usually having a length of 2 to 20 carbon atoms. For example, "$C_2$-$C_8$ alkenyl" contains two to eight carbon atoms. Alkenyl includes, but is not limited to, for example, vinyl, propenyl, butenyl, 1-methyl-2-buten-1-yl, heptenyl, octenyl, and the like.

The term "alkynyl" means a straight or branched hydrocarbon group containing one or more triple bonds and usually having a length of 2 to 20 carbon atoms. For example, "$C_2$-$C_8$ alkynyl" contains two to eight carbon atoms. Representative alkynyl groups include, but are not limited to, for example, ethynyl, 1-propynyl, 1-butynyl, heptynyl, octynyl, and the like.

The term "alkoxy" or "alkyloxy" refers to —O-alkyl. "C1-C8 alkoxy" (or alkyloxy) is meant to include C1, C2, C3, C4, C5. C6, C7, and C8 alkoxy. Examples of alkoxy groups include, but are not limited to, methoxy, ethoxy, propoxy (such as n-propoxy and isopropoxy), and tert-butoxy.

Similarly, "alkylthio" or "thioalkoxy" means an alkyl group, as defined above, with the specified number of carbon atoms connected via a sulfur bridge; for example, methyl-S— and ethyl-S—.

The term "carbonyl" refers to an organic functional group (C=O) formed by two atoms of carbon and oxygen connected by a double bond.

The term "aryl", alone or as part of a larger part such as "aralkyl", "aralkoxy" or "aryloxyalkyl", refers to a single ring having a total of 5 to 12 ring members, Bicyclic or tricyclic ring systems, wherein at least one ring in the system is aromatic and wherein each ring in the system contains 3 to 7 ring members. In certain embodiments of the present invention, "aryl" refers to an aromatic ring system, which includes, but is not limited to, phenyl, biphenyl, indanyl, 1-naphthyl, 2-naphthyl, and tetrahydronaphthalene base. The term "aralkyl" or "arylalkyl" refers to an alkyl residue attached to an aryl ring. Non-limiting examples include benzyl, phenethyl, and the like. The fused aryl group may be connected to another group at a suitable position on the cycloalkyl ring or aromatic ring. Example of the arrow line drawn from the ring system indicates that the bond can be connected to any suitable ring atom.

The term "cycloalkyl" refers to a monocyclic or bicyclic cyclic alkyl group. The monocyclic cyclic alkyl group refers to a $C_3$-$C_8$ cyclic alkyl group, including but not limited to cyclopropyl, cyclobutyl, cyclopentyl, cyclohexyl, and norbornanyl. Branched cycloalkyl groups such as 1-methylcyclopropyl and 2-methylcyclopropyl are included in the definition of "cycloalkyl". The bicyclic cyclic alkyl group includes a bridged ring, a spiro ring or a fused ring cycloalkyl group.

The term "cycloalkenyl" refers to a monocyclic or bicyclic cyclic alkenyl group. Monocyclic cyclic alkenyl refers to $C_3$-$C_8$ cyclic alkenyl, including but not limited to cyclopropenyl, cyclobutenyl, cyclopentenyl, cyclohexenyl and norbornenyl. Branched cycloalkenyl groups such as 1-methylcyclopropenyl and 2-methylcyclopropenyl are included in the definition of "cycloalkenyl". The bicyclic cyclic alkenyl group includes a bridged ring, a spiro ring or a fused ring cyclic alkenyl group.

"Halo" or "halogen" includes fluorine, chlorine, bromine and iodine. "Haloalkyl" is intended to include branched and straight chain saturated aliphatic hydrocarbon groups having the specified number of carbon atoms and substituted with one or more halogens. Examples of haloalkyl groups include, but are not limited to, fluoromethyl, difluoromethyl, trifluoromethyl, trichloromethyl, pentafluoroethyl, pentachloroethyl, 2,2,2-trifluoroethyl, heptafluoromethyl Propyl and heptachloropropyl. Examples of haloalkyl groups also include "fluoroalkyl groups" intended to include branched and straight chain saturated aliphatic hydrocarbon groups having a specified number of carbon atoms and substituted with one or more fluorine atoms.

"Haloalkoxy" or "haloalkyloxy" means a haloalkyl group as defined above with the specified number of carbon atoms connected via an oxygen bridge. For example, "C1-C8 haloalkoxy" is meant to include C1, C2, C3, C4, C5, C6, C7, and C8 haloalkoxy. Examples of haloalkoxy include, but are not limited to, trifluoromethoxy, 2,2,2-trifluoroethoxy, and pentafluoroethoxy. Similarly, "haloalkylthio" or "thiohaloalkoxy" means a haloalkyl group as defined above that has the specified number of carbon atoms connected by a sulfur bridge; for example, trifluoromethyl-S— and pentafluoroethyl —S—.

The term "aryl" refers to a monocyclic or bicyclic (and more than bicyclic) aromatic group of all carbon atoms. A monocyclic aromatic group refers to a phenyl group, and a bicyclic or more aromatic group refers to naphthyl, anthracenyl, etc. At the same time, the aryl bicyclic ring can also be a benzene ring fused with a cycloalkyl group or a ring Alkenyl, or fused with a cycloalkynyl group.

The term "aromatic heterocyclic group", "aromatic heterocyclic ring", "aromatic heterocyclic group" or "aromatic heterocyclic group" means a stable 3-, 4-, 5-, 6-, or 7-membered aromatic monocyclic or Aromatic bicyclic or 7-membered, 8-membered, 9-membered, 10-membered, 11-membered, 12-membered, 13-membered or 14-membered aromatic polycyclic heterocyclic ring, which is fully unsaturated, partially unsaturated, and contains carbon atoms and 1, 2, 3, or 4 heteroatoms independently selected from N, O, and S; and include any of the following polycyclic groups in which any heterocyclic ring as defined above is fused with a benzene ring. Nitrogen and sulfur heteroatoms can optionally be oxidized. The nitrogen atom is substituted or unsubstituted (ie, N or NR, where R is H or another substituent if defined). The heterocyclic ring can be attached to its pendant group at any heteroatom or carbon atom that results in a stable structure. If the resulting compound is stable, the heterocyclic group described herein may be substituted on a carbon or nitrogen atom. The nitrogen in the heterocycle can optionally be quaternized. Preferably, when the total number of S and O atoms in the heterocycle exceeds 1, then these heteroatoms are not adjacent to each other. Preferably, the total number of S and O atoms in the heterocycle is not more than 1. When the term "heterocycle" is used, it is intended to include heteroaryl groups. Examples of aromatic heterocycles include, but are not limited to, acridinyl, azetidinyl, azocinyl, benzimidazolyl, benzofuranyl, benzothiofuranyl, benzothienyl, benzoxanyl Azolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carboline, chromanyl, chromenyl, cinnolinyl, decahydroquinolinyl, 2H,6H-1,5,2-dithiazinyl, dihydrofuro[2, 3-b] Tetrahydrofuranyl, furanyl, furazanyl, imidazolidinyl, imidazolinyl, imidazolyl, 1H-indazolyl, imidazopyridyl, indolenyl, indolenyl, Indazinyl, indolyl, 3H-indolyl, isatinoyl, isobenzofuranyl, isochromanyl, isoindazolyl, isoindolyl, isoindolyl, iso-ouinolinyl, isothiazolyl, isothiazolopyridyl, isoxazolyl, isoxazolopyridyl, methylenedioxyphenyl, morpholinyl, naphtholinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, Oxazolidinyl, oxazolyl, oxazopyridinyl, oxazolidinyl, perimidine phenyl, oxindole, pyrimidinyl, phenanthridinyl, phenanthrolinyl, phenazinyl, phenothiazinyl, phenoxathiyl, phenoxazinyl, phthalazinyl, piperazinyl, piperidinyl, piperidinone, 4-piperidinone, piperonyl, pteridinyl, purinyl, Pyranyl, pyrazinyl, pyrazolidinyl, pyrazolinyl, pyrazolopyridyl, pyrazolyl, pyridazinyl, pyridooxazolyl, pyridoimidazolyl, pyridothiazolyl, pyridyl, Pyrimidinyl, pyrrolidinyl, pyrrolinyl, 2-pyrrolidinone, 2H-pyrrolyl, pyrrolyl, quinazolinyl, quinolinyl, 4H-quinazinyl, quinoxalinyl, quinuclidinyl, Tetrazolyl, tetrahydrofuranyl, tetrahydroisoquinolinyl, tetrahydroquinolinyl, 6H-1,2, 5-thiadiazinyl, 1,2,3-thiadiazolyl, 1,2,4-Thiadiazolyl, 1,2,5-thiadiazolyl, 1,3,4-thiadiazolyl, thiaanthryl, thiazolyl, thienyl, thiazolopyridyl, thienothiazolyl, thienooxa Azolyl, thienoimidazolyl, thienyl, triazinyl, 1,2,3-triazolyl, 1,2,4-triazolyl, 1,2,5-triazolyl, 1,3,4-Triazolyl and xanthene, quinolinyl, isoquinolinyl, phthalazinyl, quinazolinyl, indolyl, isoindolyl, indolinyl, 1H-indazolyl, benzo Imidazolyl, 1,2, 3,4-tetrahydroquinolinyl, 1,2,3,4-tetrahydroisoquinolinyl, 5,6,7,8-tetrahydro-quinolinyl, 2,3-Dihydro-benzofuranyl, chromanyl, 1,2,3,4-tetrahydro-quinoxalinyl and 1,2,3,4-tetrahydro-quinazolinyl. The present invention also includes condensed ring and spiro ring compounds containing, for example, the aforementioned heterocyclic ring.

As used herein, the term "heterocycloalkyl" refers to a monocyclic heterocycloalkyl system, or a bicyclic heterocycloalkyl system, and also includes spiro heterocycles or bridged heterocycloalkyls. The monocyclic heterocycloalkyl refers to a 3-8 membered, and at least one saturated or unsaturated but not aromatic cyclic alkyl system selected from O, N, S, and P. The bicyclic heterocycloalkyl system refers to a heterocycloalkyl group fused to a phenyl group, or a cycloalkyl group, or a cycloalkenyl group, or a heterocycloalkyl group, or a heteroaryl group.

The term "bridged cycloalkyl" as used herein refers to polycyclic compounds that share two or more carbon atoms. It can be divided into two-ring bridged cyclic hydrocarbon and polycyclic bridged cyclic hydrocarbon. The former is composed of two alicyclic rings sharing more than two carbon atoms; the latter is a bridged cyclic hydrocarbon composed of more than three rings.

The term "spirocycloalkyl" as used herein refers to a polycyclic hydrocarbon that shares one carbon atom (called a spiro atom) between single rings.

As used herein, the term "bridged heterocyclic group" refers to a polycyclic compound sharing two or more carbon atoms, and the ring contains at least one atom selected from O, N, and S. It can be divided into two-ring bridged heterocyclic ring and polycyclic bridged heterocyclic ring.

As used herein, the term "heterospirocyclyl" refers to a polycyclic hydrocarbon sharing one carbon atom (called a spiro atom) between single rings, and the ring contains at least one atom selected from O, N, and S.

The term "substitution" as used herein means that at least one hydrogen atom is replaced by a non-hydrogen group, provided that the normal valence is maintained and the substitution results in a stable compound. The ring double bond used herein is a double bond formed between two adjacent ring atoms (for example, C=C, C=N, or N=N).

In the case where nitrogen atoms (such as amines) are present on the compounds of the present invention, these nitrogen atoms can be converted into N-oxides by treatment with an oxidizing agent (such as mCPBA and/or hydrogen peroxide) to obtain other compounds of the present invention. Therefore, the shown and claimed nitrogen atoms are considered to encompass both the shown nitrogen and its N-oxides to obtain the derivatives of the invention.

When any variable occurs more than once in any composition or formula of a compound, its definition at each occurrence is independent of its definition at every other occurrence. Thus, for example, if a group is shown substituted with 0-3 R, the group may be optionally substituted with up to three R groups, and R is independently selected from the definition of R at each occurrence. In addition, combinations of substituents and/or variables are permitted only when the above combinations can produce stable compounds.

The term "solvate" means the physical association of a compound of the invention with one or more solvent molecules (whether organic or inorganic). This physical association includes hydrogen bonding. In some cases, such as when one or more solvent molecules are incorporated into the crystal lattice of the crystalline solid, the solvate will be able to be separated. The solvent molecules in the solvate can be arranged in regular and/or disordered arrangements. Solvates may contain stoichiometric or non-stoichiometric solvent molecules. "Solvate" encompasses both solution-phase and isolatable solvates. Exemplary solvates include, but are not limited to, hydrate, ethanolate, methanolate, and isopropanolate. Solvation methods are well known in the art.

The term "patient" as used herein refers to an organism that is treated by the method of the present invention. Such organisms preferably include, but are not limited to, mammals (e.g., murine, ape/monkey, horse, cow, pig, dog, cat, etc.) and most preferably refer to humans.

The term "effective amount" as used herein means the amount of a drug or agent (ie, the compound of the present invention) that will elicit a biological or medical response of a tissue, system, animal, or human sought by, for example, a researcher or clinician. In addition, the term "therapeutically effective amount" means an amount that results in an improved treatment, cure, prevention, or alleviation of a disease, disorder, or side effect, or reduction in disease, compared to a corresponding subject not receiving the above amount, or the rate of progression of the disease. The effective amount can be given in one or more administrations, administrations or doses and is not intended to be limited by a particular formulation or route of administration. The term also includes within its scope an effective amount for enhancing normal physiological functions.

The term "treatment" as used herein includes any effect that leads to amelioration of a condition, disease, disorder, etc., such as alleviating, reducing, regulating, improving or eliminating, or improving its symptoms.

The term "pharmaceutical composition" as used herein refers to a combination of an active agent and an inert or active carrier, so that the composition is particularly suitable for in vivo or ex vivo diagnosis or treatment. Examples of bases include, but are not limited to, alkali metal (e.g., sodium) hydroxide, alkaline earth metal (e.g., magnesium) hydroxide, ammonia, and the like. For therapeutic use, the salt of the compound of the present invention is expected to be pharmaceutically acceptable for therapeutic use. However, salts of non-pharmaceutically acceptable acids and bases can also be used, for example, in the preparation or purification of pharmaceutical compounds.

The term "medicinal" is used herein to refer to the following compounds, substances, compositions and/or dosage forms: within the scope of reasonable medical judgment, they are suitable for use in contact with human and animal tissues without excessive toxicity or irritation Sex, allergic reactions and/or other problems or complications, and are commensurate with a reasonable benefit/risk ratio.

The phrase "pharmaceutically acceptable carrier" as used herein means a pharmaceutical substance, composition or vehicle, such as liquid or solid fillers, diluents, excipients, manufacturing aids (e.g. lubricants, talc, magnesium stearate, Calcium stearate or zinc stearate or stearic acid) or solvent encapsulated substances, which involve carrying or transporting the subject compound from one organ or part of the body to another organ or part of the body. Each carrier must be "acceptable" in the sense of being compatible with the other ingredients of the formulation and harmless to the patient.

The term "pharmaceutical composition" means a composition comprising a compound of the present invention and at least one other pharmaceutical carrier. "Pharmaceutical carrier" refers to a medium generally accepted in the art for delivering biologically active agents to animals (specifically mammals), including (ie) adjuvants, excipients or vehicles, such as diluents, preservatives, Fillers, flow regulators, disintegrants, wetting agents, emulsifiers, suspending agents, sweeteners, flavoring agents, fragrances, antibacterial agents, antifungal agents, lubricants and dispersants, this depends on the mode of administration and the nature of the dosage form.

Specific Pharmacy and Medical Terms

The term "acceptable", as used herein, refers to a prescription component or active ingredient that does not have unduly harmful effects on the health of the general treatment target.

The term "cancer", as used herein, refers to an abnormal growth of cells that cannot be controlled and that can metastasize (spread) under certain conditions. This type of cancer includes, but is not limited to, solid tumors (such as bladder, intestine, brain, chest, uterus, heart, kidney, lung, lymphoid tissue (lymphoma), ovary, pancreas or other endocrine organs (such as thyroid), prostate, skin (melanoma) or hematoma (such as non-leukemic leukemia).

The term "co-administration" or its analogous terms, as used herein, refers to administering several selected therapeutic drugs to a patient in the same or different modes of administration at the same or different times.

The term "enhance" or "enhance", as used herein, means that the expected result can be increased or prolonged in terms of potency or duration. Therefore, in terms of enhancing the therapeutic effect of drugs, the term "enhanced" refers to the ability of drugs to increase or extend potency or duration in the system. "Synergy value" as used herein refers to the ability of another therapeutic drug to be maximized in an ideal system.

The term "immune disease" refers to a disease or symptom that produces an adverse or harmful reaction to endogenous or exogenous antigens. The result is usually cell dysfunction, or destruction and dysfunction, or destruction of organs or tissues that may produce immune symptoms.

The terms "kit" and "product packaging" are synonymous.

The term "subject" or "patient" includes mammals and non-mammals. Mammals include, but are not limited to, mammals: humans and non-human primates such as orangutans, apes and monkeys; agricultural animals such as cows, horses, goats, sheep, pigs; domestic animals such as rabbits and dogs; laboratory animals include rodents, Such as rats, mice and guinea pigs.

Non-mammalian animals include, but are not limited to, birds, fish, etc. In a preferred example, the selected mammal is a human.

The terms "treatment", "treatment process" or "therapy" as used herein include alleviating, inhibiting or improving the symptoms or conditions of diseases; inhibiting the occurrence of complications; improving or preventing underlying metabolic syndrome; inhibiting the occurrence of diseases or symptoms, Such as controlling the development of diseases or conditions; reducing diseases or symptoms; reducing diseases or symptoms; reducing complications caused by diseases or symptoms, or preventing and/or treating signs caused by diseases or symptoms.

As used herein, a certain compound or pharmaceutical composition, after administration, can improve a certain disease, symptom or condition, especially its severity, delay the onset, slow the progression of the disease, or reduce the duration of the disease. Regardless of fixed administration or temporary administration, continuous administration or intermittent administration, it can be attributed to or related to the administration.

Route of Administration

Suitable routes of administration include, but are not limited to, oral, intravenous, rectal, aerosol, parenteral, ocular, pulmonary, transdermal, vaginal, and ear canal administration, Nasal cavity administration and local administration. In addition, for example only, parenteral administration includes intramuscular injection, subcutaneous injection, intravenous injection, intramedullary injection, ventricular injection, intraperitoneal injection, intralymphatic injection, and intranasal injection.

In one aspect, the mode of administration of the compounds described herein is a local rather than a systemic mode of administration. In certain embodiments, the long-acting formulation is administered by implantation (for example, subcutaneously or intramuscularly) or by intramuscular injection. In addition, in another embodiment, the drug is administered through a targeted drug delivery system. For example, liposomes encapsulated by organ-specific antibodies. In this specific embodiment, the liposomes are selectively targeted to specific organs and absorbed.

Pharmaceutical Composition and Dosage

The present invention also provides a pharmaceutical composition, which comprises a therapeutically effective amount of one or more compounds of the present invention formulated together with one or more pharmaceutical carriers (additives) and/or diluents, and optionally one or more of the above-mentioned other therapeutic agents. The compound of the present invention can be administered by any suitable means for any of the above-mentioned purposes, for example, oral administration, such as tablets, pills, powders, granules, elixirs, tinctures, suspensions (including nanosuspensions, microsuspensions, spray-dried Dispersions), syrups and emulsions; sublingually; buccal; parenterally, such as by subcutaneous, intravenous, intramuscular or intrasternal injection or infusion techniques (for example, in a sterile injectable aqueous or non-aqueous solution or suspension Liquid form); nasal, including administration to the nasal membranes, such as by inhalation spray; topical, such as in the form of creams or ointments; or transrectally, such as in the form of suppositories. They can be administered alone, but are usually administered using a pharmaceutical carrier selected based on the chosen route of administration and standard pharmaceutical practice.

The pharmaceutical carrier is formulated according to many factors within the scope of those skilled in the art. These factors include, but are not limited to: the type and nature of the active agent formulated; the subject to whom the composition containing the active agent is to be administered; the expected route of administration of the composition; and the targeted therapeutic indication. Pharmaceutical carriers include aqueous and non-aqueous liquid media and various solid and semi-solid dosage forms.

The above-mentioned carrier may include many different ingredients and additives in addition to the active agent, and the above-mentioned other ingredients are included in the formulation for various reasons known to those skilled in the art, such as stabilizing the active agent, binder, and the like. A description of the factors involved in the selection of suitable pharmaceutical carriers and carriers can be found in many readily available sources, such as Allen L. V. Jr. et al. Remington: The Science and Practice of Pharmacy (2 Volumes), 22nd Edition (2012), Pharmaceutical Press.

Of course, the dosage regimen of the compound of the present invention varies depending on known factors, such as the pharmacodynamic properties of the specific agent and its administration mode and route; the species, age, sex, health status, medical condition and weight of the recipient; The nature and degree of symptoms; the types of simultaneous treatment; the frequency of treatment; the route of administration, the patient's renal and liver function, and the desired effect. According to general guidelines, when used for a given effect, the daily oral dose of each active ingredient should be about 0.001 mg/day to about 10-5000 mg/day, preferably about 0.01 mg/day to about 1000 mg/day, and most preferably The ground is about 0.1 mg/day to about 250 mg/day. During constant rate infusion, the most preferred intravenous dose should be about 0.01 mg/kg/min to about 10 mg/kg/min. The compounds of the present invention may be administered in a single daily dose, or the total daily dose may be administered in divided doses of two, three or four times daily.

The compound is usually in a suitable pharmaceutical diluent, excipient, or carrier (herein) appropriately selected according to the intended administration form (e.g., oral tablets, capsules, elixirs and syrups) and consistent with conventional pharmaceutical practice. Administered in the form of a mixture of drug carriers collectively.

A dosage form (pharmaceutical composition) suitable for administration may contain about 1 mg to about 2000 mg of active ingredient per dosage unit. In these pharmaceutical compositions, the active ingredient will usually be present in an amount of about 0.1-95% by weight based on the total weight of the composition.

A typical capsule for oral administration contains at least one compound of the present invention (250 mg), lactose (75 mg) and magnesium stearate (15 mg). The mixture was passed through a 60 mesh screen and packed into No. 1 gelatin capsules.

A typical injectable formulation can be prepared by aseptically placing at least one compound of the present invention (250 mg) in a bottle, aseptically lyophilizing and sealing. For use, the contents of the bottle are mixed with 2 mL of physiological saline to produce an injectable preparation.

The scope of the present invention includes (alone or in combination with a pharmaceutical carrier) pharmaceutical compositions comprising a therapeutically effective amount of at least one compound of the present invention as an active ingredient. Optionally, the compound of the present invention may be used alone, in combination with other compounds of the present invention, or in combination with one or more other therapeutic agents (eg, anticancer agents or other pharmaceutically active substances).

Regardless of the chosen route of administration, the compound of the present invention (which can be used in a suitable hydrated form) and/or the pharmaceutical composition of the present invention is formulated into a pharmaceutical dosage form by conventional methods known to those skilled in the art.

The actual dosage level of the active ingredient in the pharmaceutical composition of the present invention can be changed, so as to obtain the amount of the active ingredient that is effective for achieving the desired therapeutic response, composition, and administration mode of a specific patient without being toxic to the patient.

The selected dosage level will depend on many factors, including the activity of the particular compound of the invention or its ester, salt or amide used; route of administration; time of administration; excretion rate of the particular compound used; rate and extent of absorption The duration of treatment; other drugs, compounds and/or substances used in combination with the specific compound used; the age, sex, weight, condition, general health and previous medical history of the patient being treated and other factors known in the medical field.

A doctor or veterinarian with ordinary skill in the art can easily determine and prescribe an effective amount of the required pharmaceutical composition. For example, in order to achieve the desired therapeutic effect, the physician or veterinarian can start a competition of the compound of the present invention used in the pharmaceutical composition at a level lower than the required level, and gradually increase the dosage until the desired effect is achieved. Generally, a suitable daily dose of the compound of the invention will be the amount of the compound that is the lowest dose effective to produce a therapeutic effect. Such effective dose usually depends on the above factors. Generally, oral, intravenous, intracerebroventricular, and subcutaneous doses of the compound of the present invention for patients range from about 0.01 to about 50 mg/kg body weight/day. If desired, the effective daily dose of the active compound can be administered in two, three, four, five, six or more sub-doses at appropriate intervals throughout the day, optionally in unit dosage form. In certain aspects of the invention, the medication is administered once a day.

Although the compound of the present invention can be administered alone, it is preferably administered in the form of a pharmaceutical preparation (composition).

Kit/Product Packaging

For the treatment of the above indications, the kit/product packaging is also described here. These kits can be composed of a conveyor, a medicine pack or a container box. The container box can be divided into multiple compartments to accommodate one or more containers, such as vials, test tubes, and the like. Each container contains all A single component of the method. Suitable containers include bottles, vials, syringes and test tubes. The container is made of acceptable materials such as glass or plastic.

For example, the container may contain one or more of the compounds described herein. The compounds may exist in the form of pharmaceutical components, or they may exist as a mixture with other ingredients described herein. The container may have a sterile output port (for example, the container may be an intravenous infusion bag or a bottle, and the stopper may be pierced by a hypodermic syringe needle). Such a kit may contain a compound, and instructions, labels, or operating instructions for the method of use described herein.

A typical kit may include one or more containers. In order to meet the needs of commercial promotion and the use of compounds, each container contains one or more materials (such as reagents, or concentrated mother liquor, and/Or equipment). These materials include, but are not limited to, buffers, diluents, filters, needles, syringes, conveyors, bags, containers, bottles, and/or test tubes, with a list of contents and/or instructions for use, and instructions for the built-in packaging. The entire set of instructions must be included.

The label can be displayed on the container or closely related to the container. The appearance of a label on a container means that the label letters, numbers or other features are pasted, molded, or engraved on the container; the label can also appear in a container box or shipping box containing a variety of containers, such as in a product insert. A label can be used to indicate a specific therapeutic use of the contents. The label may also indicate instructions for use of the content, such as described in the above method.

All the features described in this specification (including any of the claims, abstracts and figures), and/or all steps involved in any method or process, may exist in any combination, unless some features Or the steps are mutually exclusive in the same combination.

The above-mentioned features mentioned in the present invention or the features mentioned in the embodiments can be combined arbitrarily. All the features disclosed in the specification of this case can be used in combination with any composition form, and each feature disclosed in the specification can be replaced by any alternative feature that can provide the same, equal or similar purpose. Therefore, unless otherwise specified, the disclosed features are only general examples of equal or similar features.

The present invention will be further explained below in conjunction with specific embodiments. It should be understood that these embodiments are only used to illustrate the present invention and not to limit the scope of the present invention. The experimental methods that do not indicate specific conditions in the following examples usually follow the conventional conditions or the conditions recommended by the manufacturer. Unless otherwise stated, all percentages, ratios, ratios, or parts are by weight.

The unit of weight-volume percentage in the present invention is well-known to those skilled in the art, for example, refers to the weight of the solute in a 100 ml solution. Unless otherwise defined, all professional and scientific terms used in the text have the same meaning as those familiar to those skilled in the art. In addition, any methods and materials similar or equivalent to the content described can be applied to the method of the present invention. The preferred implementation methods and materials described in this article are for demonstration purposes only.

In the preferred examples of the present invention, the following compounds are provided but not limited to:

| NO. | Structure |
|---|---|
| 1 | 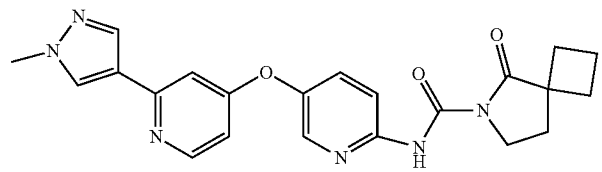 [SMILES: Cn1cc(-c2cc(Oc3ccc(NC(=O)N4CCC5(CCC5)C4=O)nc3)ccn2)cn1] |
| 2 | 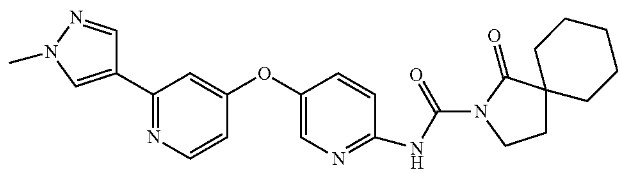 [SMILES: Cn1cc(-c2cc(Oc3ccc(NC(=O)N4CCC5(CCCCC5)C4=O)nc3)ccn2)cn1] |
| 3 | 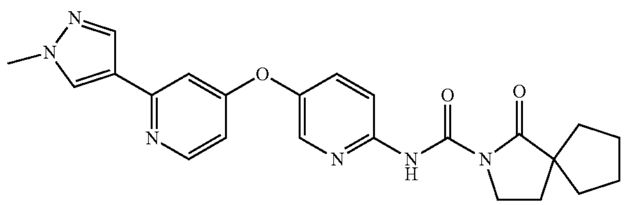 [SMILES: Cn1cc(-c2cc(Oc3ccc(NC(=O)N4CCC5(CCCC5)C4=O)nc3)ccn2)cn1] |
| 4 | 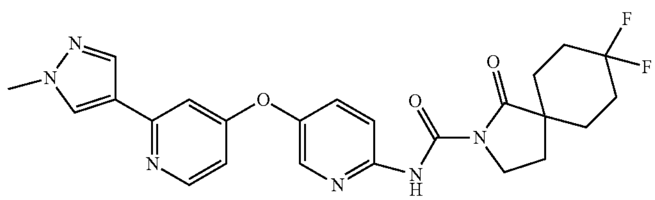 [SMILES: Cn1cc(-c2cc(Oc3ccc(NC(=O)N4CCC5(CCC(F)(F)CC5)C4=O)nc3)ccn2)cn1] |
| 5 | 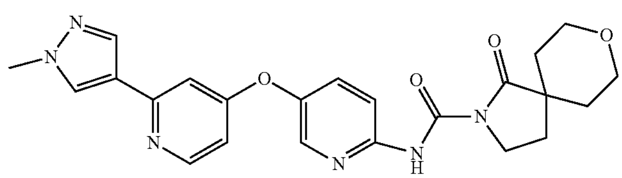 [SMILES: Cn1cc(-c2cc(Oc3ccc(NC(=O)N4CCC5(CCOCC5)C4=O)nc3)ccn2)cn1] |
| 6 | 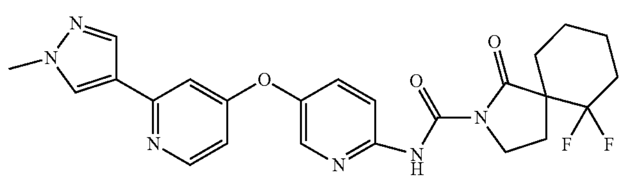 [SMILES: Cn1cc(-c2cc(Oc3ccc(NC(=O)N4CCC5(CCCCC5(F)F)C4=O)nc3)ccn2)cn1] |
| 7 | 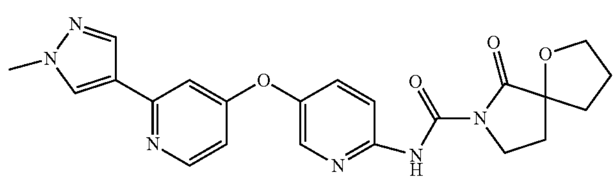 [SMILES: Cn1cc(-c2cc(Oc3ccc(NC(=O)N4CCC5(CCCO5)C4=O)nc3)ccn2)cn1] |
| 8 | 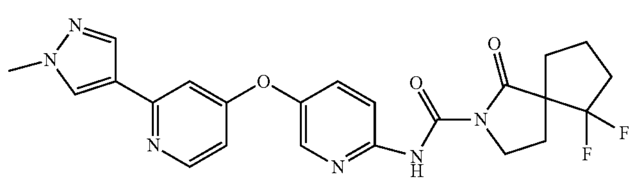 [SMILES: Cn1cc(-c2cc(Oc3ccc(NC(=O)N4CCC5(CCCC5(F)F)C4=O)nc3)ccn2)cn1] |

-continued

| NO. | Structure |
|---|---|
| 9 | 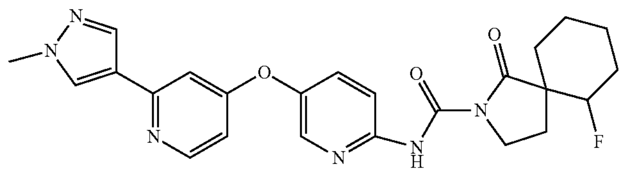 [SMILES: Cn1cc(-c2cc(Oc3ccc(NC(=O)N4CCC5(CCCCC5F)C4=O)nc3)ccn2)cn1] |
| 10 | 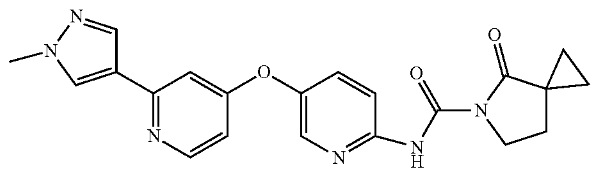 [SMILES: Cn1cc(-c2cc(Oc3ccc(NC(=O)N4CCC5(CC5)C4=O)nc3)ccn2)cn1] |
| 11 | 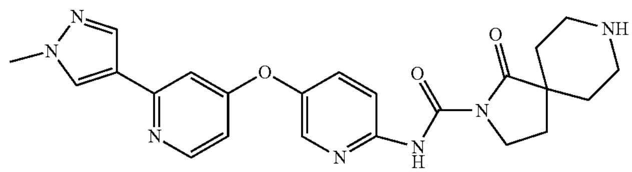 [SMILES: Cn1cc(-c2cc(Oc3ccc(NC(=O)N4CCC5(CCNCC5)C4=O)nc3)ccn2)cn1] |
| 12 | 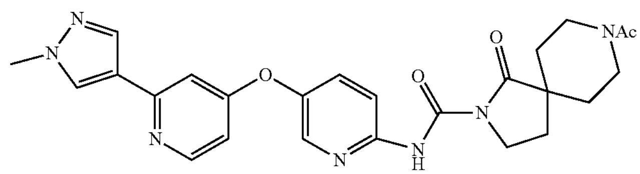 |
| 13 | 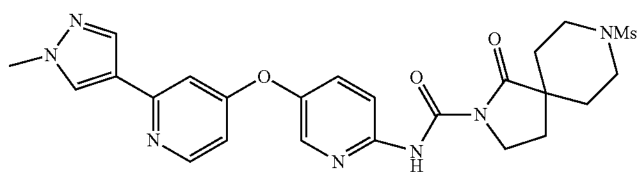 |
| 14 | 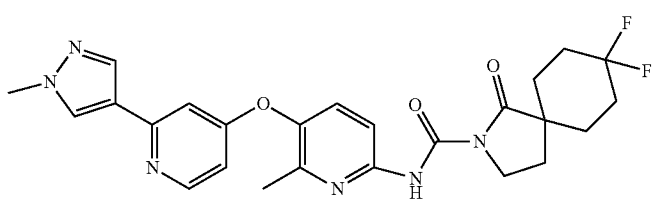 [SMILES: Cc1nc(NC(=O)N2CCC3(CCC(F)(F)CC3)C2=O)ccc1Oc1ccnc(-c2cnn(C)c2)c1] |
| 15 | 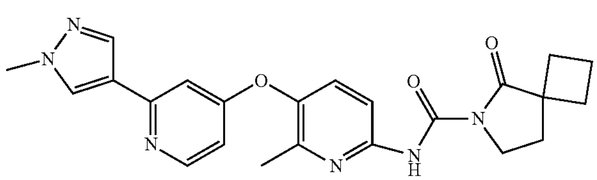 [SMILES: Cc1nc(NC(=O)N2CCC3(CCC3)C2=O)ccc1Oc1ccnc(-c2cnn(C)c2)c1] |
| 16 | 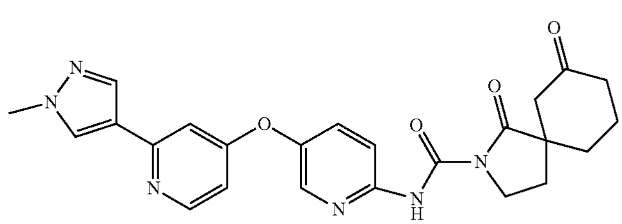 [SMILES: Cn1cc(-c2cc(Oc3ccc(NC(=O)N4CCC5(CCCC(=O)C5)C4=O)nc3)ccn2)cn1] |

| NO. | Structure |
|---|---|
| 17 | 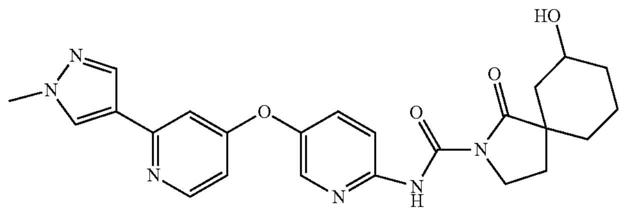 [SMILES: Cn1cc(-c2cc(Oc3ccc(NC(=O)N4CCC5(CCCC(O)C5)C4=O)nc3)ccn2)cn1] |
| 18 | 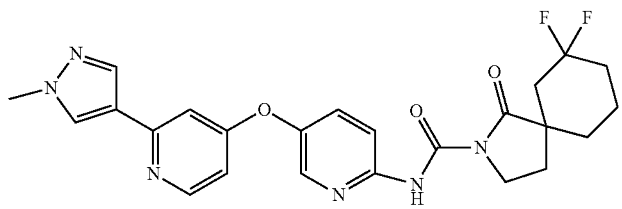 [SMILES: Cn1cc(-c2cc(Oc3ccc(NC(=O)N4CCC5(CCCC(F)(F)C5)C4=O)nc3)ccn2)cn1] |
| 19 | 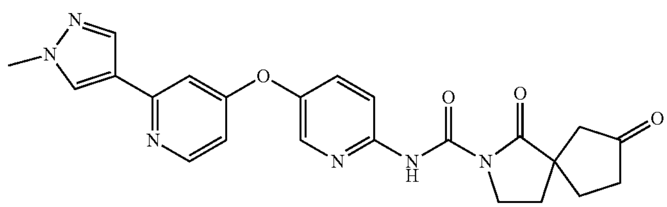 [SMILES: Cn1cc(-c2cc(Oc3ccc(NC(=O)N4CCC5(CCC(=O)C5)C4=O)nc3)ccn2)cn1] |
| 20 | 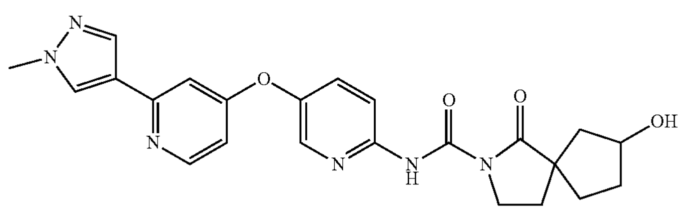 [SMILES: Cn1cc(-c2cc(Oc3ccc(NC(=O)N4CCC5(CCC(O)C5)C4=O)nc3)ccn2)cn1] |
| 21 | 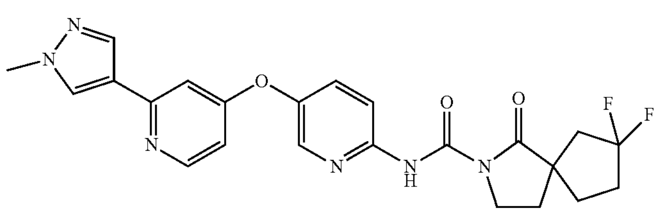 [SMILES: Cn1cc(-c2cc(Oc3ccc(NC(=O)N4CCC5(CCC(F)(F)C5)C4=O)nc3)ccn2)cn1] |
| 22 | 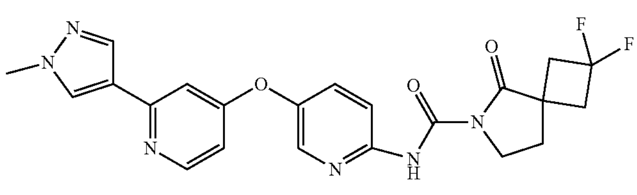 [SMILES: Cn1cc(-c2cc(Oc3ccc(NC(=O)N4CCC5(CC(F)(F)C5)C4=O)nc3)ccn2)cn1] |
| 23 | 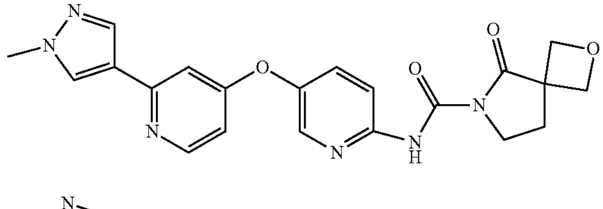 |
| 24 | 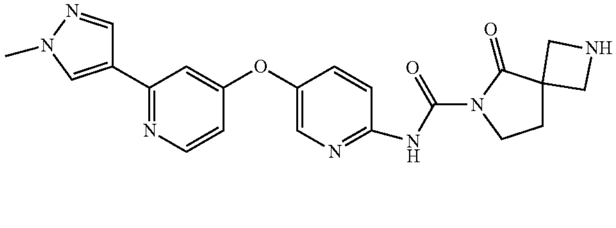 [SMILES: Cn1cc(-c2cc(Oc3ccc(NC(=O)N4CCC5(CNC5)C4=O)nc3)ccn2)cn1] |

-continued

| NO. | Structure |
|---|---|
| 25 | 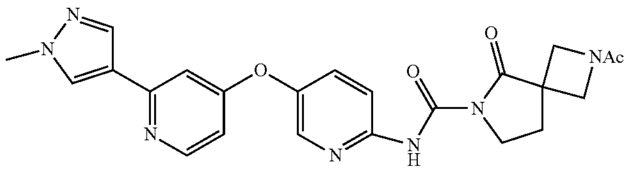 |
| 26 | 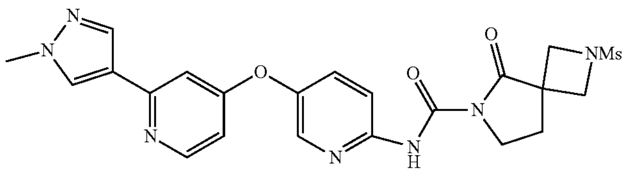 |
| 27 | 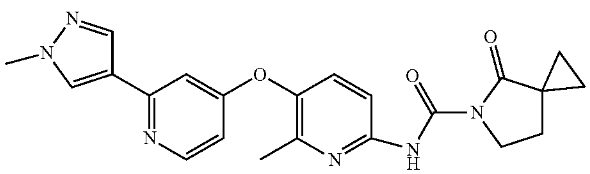 [SMILES: Cc1nc(NC(=O)N2CCC3(CC3)C2=O)ccc1Oc1ccnc(-c2cnn(C)c2)c1] |
| 28 | 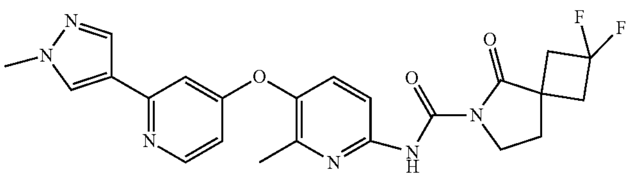 [SMILES: Cc1nc(NC(=O)N2CCC3(CC(F)(F)C3)C2=O)ccc1Oc1ccnc(-c2cnn(C)c2)c1] |
| 29 | 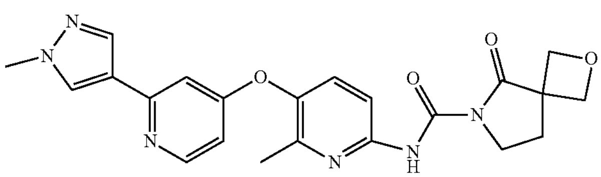 [SMILES: Cc1nc(NC(=O)N2CCC3(COC3)C2=O)ccc1Oc1ccnc(-c2cnn(C)c2)c1] |
| 30 | 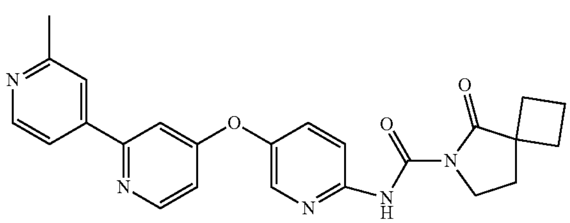 [SMILES: Cc1cc(-c2cc(Oc3ccc(NC(=O)N4CCC5(CCC5)C4=O)nc3)ccn2)ccn1] |
| 31 | 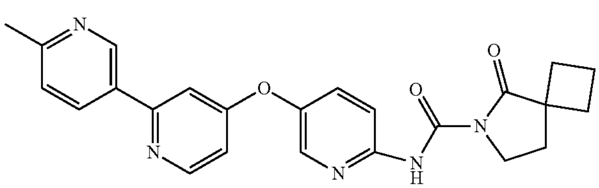 [SMILES: Cc1ccc(-c2cc(Oc3ccc(NC(=O)N4CCC5(CCC5)C4=O)nc3)ccn2)cn1] |
| 32 | 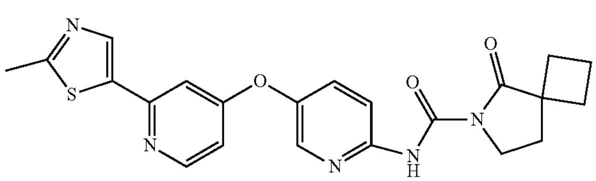 [SMILES: Cc1ncc(-c2cc(Oc3ccc(NC(=O)N4CCC5(CCC5)C4=O)nc3)ccn2)s1] |

| NO. | Structure |
|---|---|
| 33 | 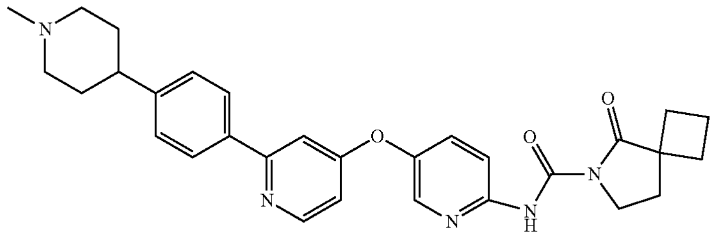 [SMILES: CN1CCC(c2ccc(-c3cc(Oc4ccc(NC(=O)N5CCC6(CCC6)C5=O)nc4)ccn3)cc2)CC1] |
| 34 | 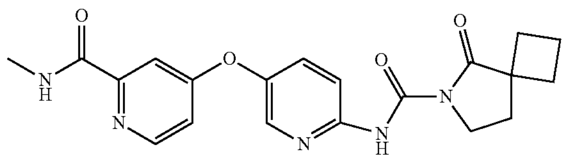 [SMILES: CNC(=O)c1cc(Oc2ccc(NC(=O)N3CCC4(CCC4)C3=O)nc2)ccn1] |
| 35 | 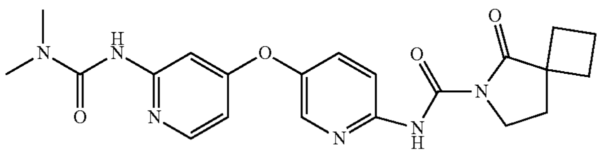 [SMILES: CN(C)C(=O)Nc1cc(Oc2ccc(NC(=O)N3CCC4(CCC4)C3=O)nc2)ccn1] |
| 36 | 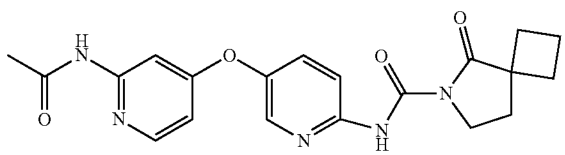 [SMILES: CC(=O)Nc1cc(Oc2ccc(NC(=O)N3CCC4(CCC4)C3=O)nc2)ccn1] |
| 37 | 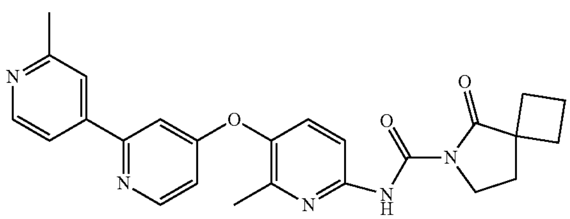 [SMILES: Cc1cc(-c2cc(Oc3ccc(NC(=O)N4CCC5(CCC5)C4=O)nc3C)ccn2)ccn1] |
| 38 | 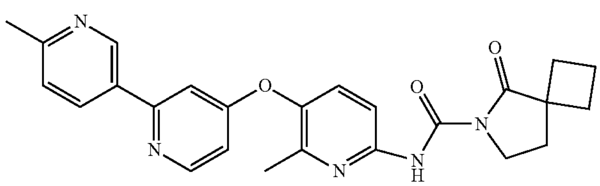 [SMILES: Cc1ccc(-c2cc(Oc3ccc(NC(=O)N4CCC5(CCC5)C4=O)nc3C)ccn2)cn1] |
| 39 | 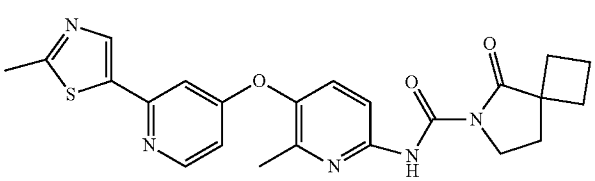 [SMILES: Cc1ncc(-c2cc(Oc3ccc(NC(=O)N4CCC5(CCC5)C4=O)nc3C)ccn2)s1] |
| 40 | 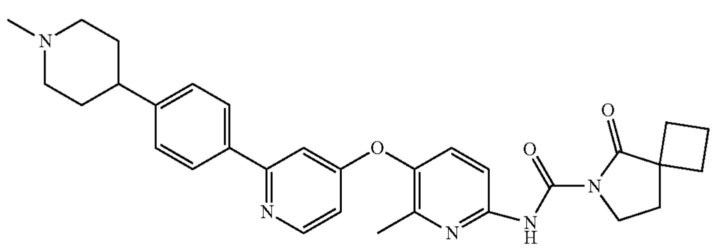 [SMILES: Cc1nc(NC(=O)N2CCC3(CCC3)C2=O)ccc1Oc1ccnc(-c2ccc(C3CCN(C)CC3)cc2)c1] |

-continued

| NO. | Structure |
|-----|-----------|
| 41 | 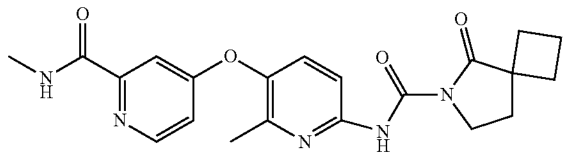 [SMILES: CNC(=O)c1cc(Oc2ccc(NC(=O)N3CCC4(CCC4)C3=O)nc2C)ccn1] |
| 42 | 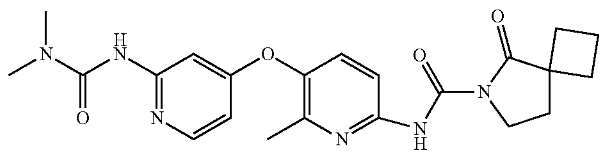 [SMILES: Cc1nc(NC(=O)N2CCC3(CCC3)C2=O)ccc1Oc1ccnc(NC(=O)N(C)C)c1] |
| 43 | 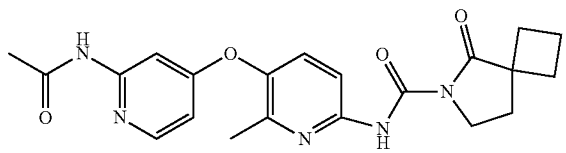 [SMILES: CC(=O)Nc1cc(Oc2ccc(NC(=O)N3CCC4(CCC4)C3=O)nc2C)ccn1] |
| 44 | 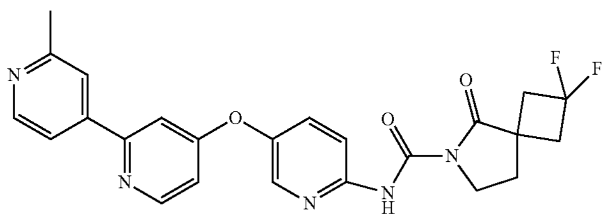 [SMILES: Cc1cc(-c2cc(Oc3ccc(NC(=O)N4CCC5(CC(F)(F)C5)C4=O)nc3)ccn2)ccn1] |
| 45 | 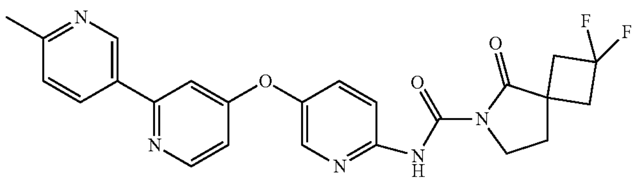 [SMILES: Cc1ccc(-c2cc(Oc3ccc(NC(=O)N4CCC5(CC(F)(F)C5)C4=O)nc3)ccn2)cn1] |
| 46 | 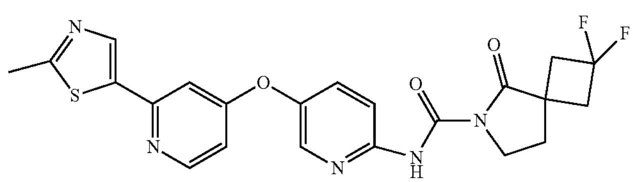 [SMILES: Cc1ncc(-c2cc(Oc3ccc(NC(=O)N4CCC5(CC(F)(F)C5)C4=O)nc3)ccn2)s1] |
| 47 | 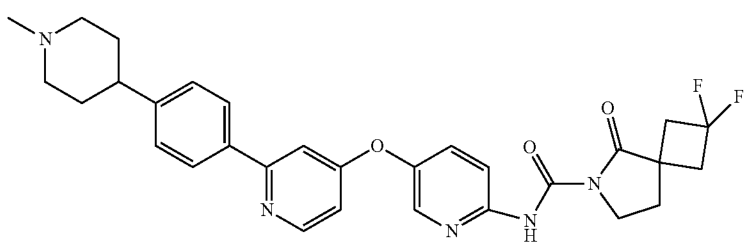 [SMILES: CN1CCC(c2ccc(-c3cc(Oc4ccc(NC(=O)N5CCC6(CC(F)(F)C6)C5=O)nc4)ccn3)cc2)CC1] |
| 48 | 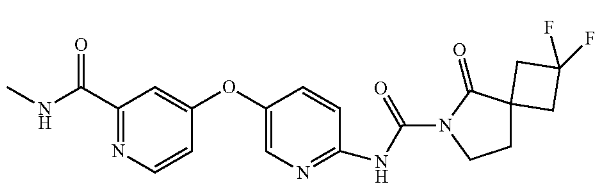 [SMILES: CNC(=O)c1cc(Oc2ccc(NC(=O)N3CCC4(CC(F)(F)C4)C3=O)nc2)ccn1] |

| NO. | Structure |
|---|---|
| 49 | 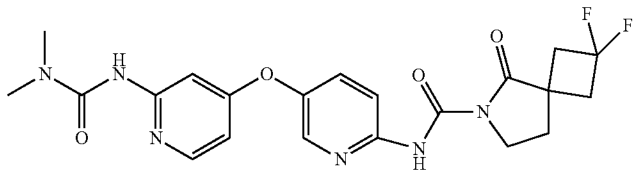 [SMILES: CN(C)C(=O)Nc1cc(Oc2ccc(NC(=O)N3CCC4(CC(F)(F)C4)C3=O)nc2)ccn1] |
| 50 | 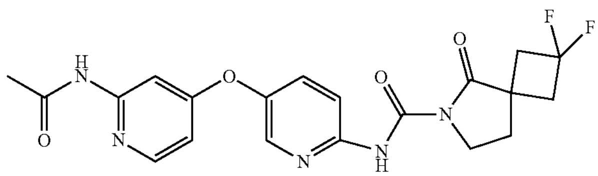 [SMILES: CC(=O)Nc1cc(Oc2ccc(NC(=O)N3CCC4(CC(F)(F)C4)C3=O)nc2)ccn1] |
| 51 | 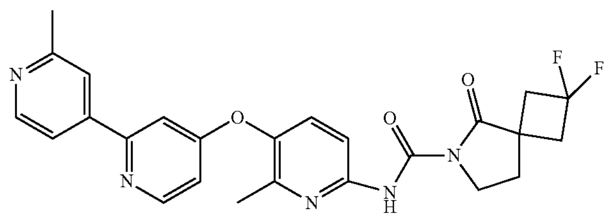 [SMILES: Cc1cc(-c2cc(Oc3ccc(NC(=O)N4CCC5(CC(F)(F)C5)C4=O)nc3C)ccn2)ccn1] |
| 52 | 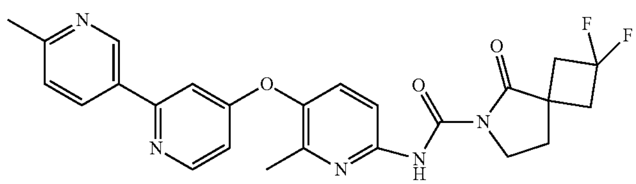 [SMILES: Cc1ccc(-c2cc(Oc3ccc(NC(=O)N4CCC5(CC(F)(F)C5)C4=O)nc3C)ccn2)cn1] |
| 53 | 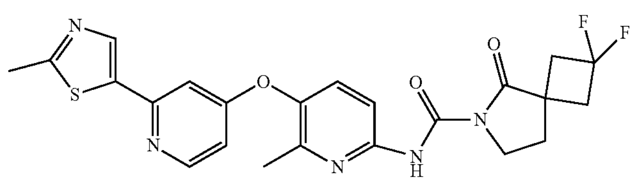 [SMILES: Cc1ncc(-c2cc(Oc3ccc(NC(=O)N4CCC5(CC(F)(F)C5)C4=O)nc3C)ccn2)s1] |
| 54 | 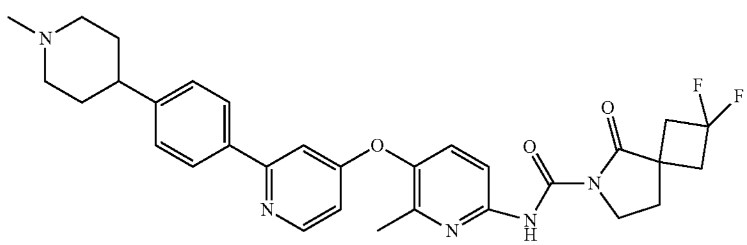 [SMILES: Cc1nc(NC(=O)N2CCC3(CC(F)(F)C3)C2=O)ccc1Oc1ccnc(-c2ccc(C3CCN(C)CC3)cc2)c1] |
| 55 | 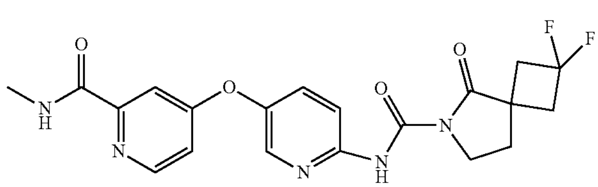 [SMILES: CNC(=O)c1cc(Oc2ccc(NC(=O)N3CCC4(CC(F)(F)C4)C3=O)nc2)ccn1] |
| 56 | 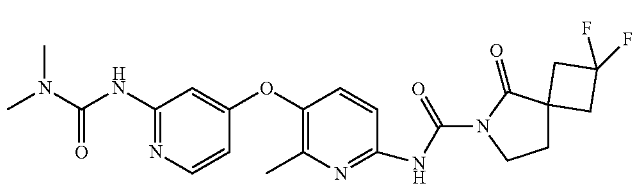 [SMILES: Cc1nc(NC(=O)N2CCC3(CC(F)(F)C3)C2=O)ccc1Oc1ccnc(NC(=O)N(C)C)c1] |

| NO. | Structure |
|---|---|
| 57 | 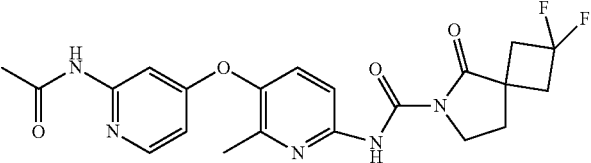 [SMILES: CC(=O)Nc1cc(Oc2ccc(NC(=O)N3CCC4(CC(F)(F)C4)C3=O)nc2C)ccn1] |
| 58 | 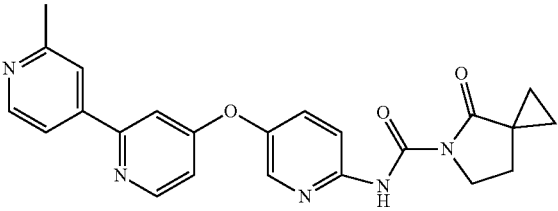 [SMILES: Cc1cc(-c2cc(Oc3ccc(NC(=O)N4CCC5(CC5)C4=O)nc3)ccn2)ccn1] |
| 59 | 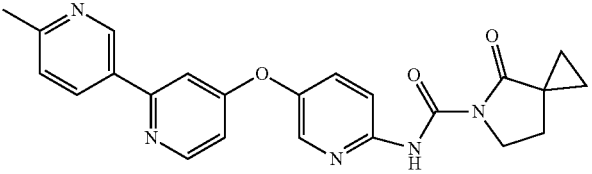 [SMILES: Cc1ccc(-c2cc(Oc3ccc(NC(=O)N4CCC5(CC5)C4=O)nc3)ccn2)cn1] |
| 60 | 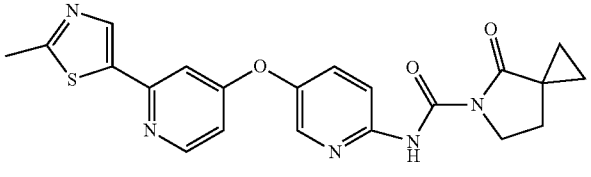 [SMILES: Cc1ncc(-c2cc(Oc3ccc(NC(=O)N4CCC5(CC5)C4=O)nc3)ccn2)s1] |
| 61 | 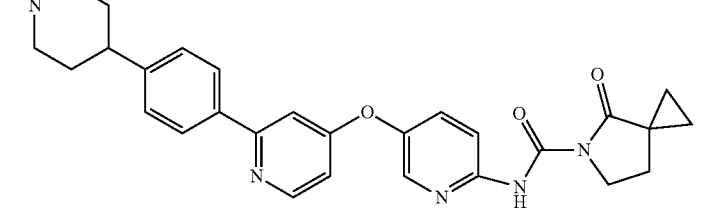 |
| 62 | 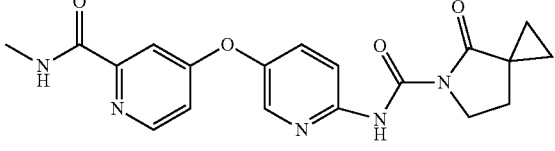 |
| 63 | 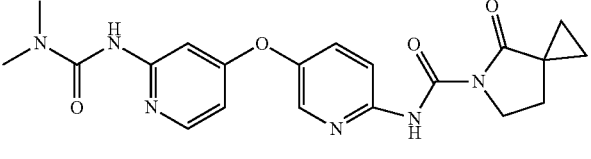 [SMILES: CN(C)C(=O)Nc1cc(Oc2ccc(NC(=O)N3CCC4(CC4)C3=O)nc2)ccn1] |
| 64 | 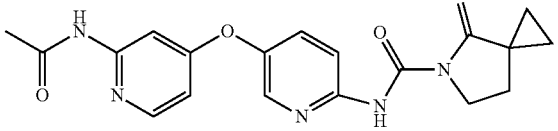 |

-continued

| NO. | Structure |
|---|---|
| 65 | 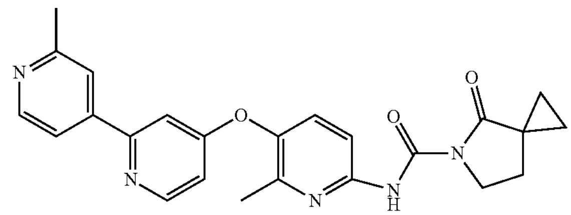 [SMILES: Cc1cc(-c2cc(Oc3ccc(NC(=O)N4CCC5(CC5)C4=O)nc3C)ccn2)ccn1] |
| 66 | 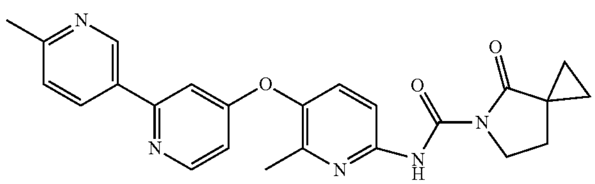 [SMILES: Cc1ccc(-c2cc(Oc3ccc(NC(=O)N4CCC5(CC5)C4=O)nc3C)ccn2)cn1] |
| 67 | 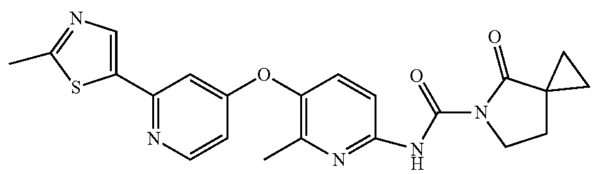 [SMILES: Cc1ncc(-c2cc(Oc3ccc(NC(=O)N4CCC5(CC5)C4=O)nc3C)ccn2)s1] |
| 68 | 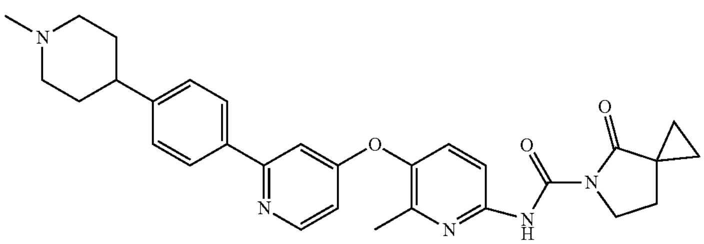 [SMILES: Cc1nc(NC(=O)N2CCC3(CC3)C2=O)ccc1Oc1ccnc(-c2ccc(C3CCN(C)CC3)cc2)c1] |
| 69 | 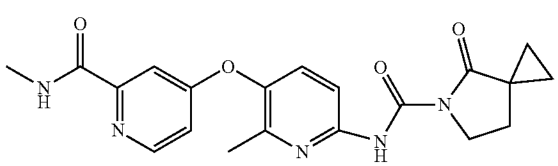 [SMILES: CNC(=O)c1cc(Oc2ccc(NC(=O)N3CCC4(CC4)C3=O)nc2C)ccn1] |
| 70 | 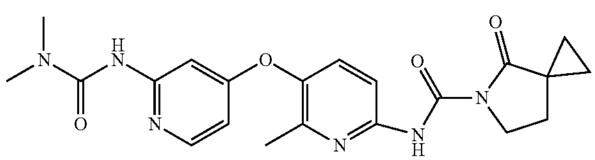 [SMILES: Cc1nc(NC(=O)N2CCC3(CC3)C2=O)ccc1Oc1ccnc(NC(=O)N(C)C)c1] |
| 71 | 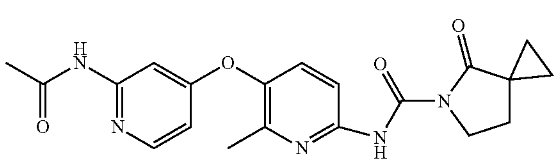 [SMILES: CC(=O)Nc1cc(Oc2ccc(NC(=O)N3CCC4(CC4)C3=O)nc2C)ccn1] |
| 72 | 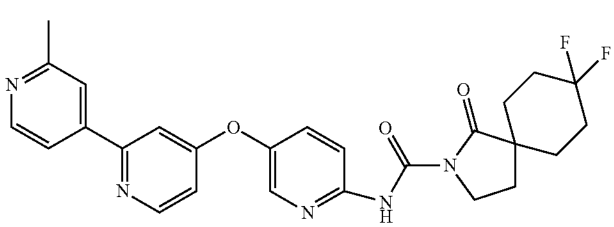 [SMILES: Cc1cc(-c2cc(Oc3ccc(NC(=O)N4CCC5(CCC(F)(F)CC5)C4=O)nc3)ccn2)ccn1] |

-continued

| NO. | Structure |
|---|---|
| 73 | 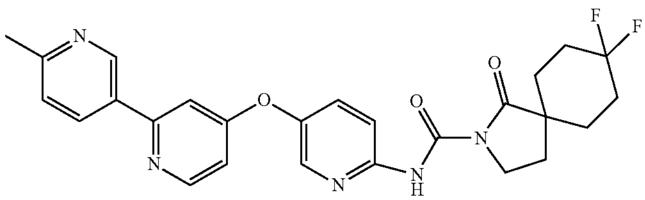 [SMILES: Cc1ccc(-c2cc(Oc3ccc(NC(=O)N4CCC5(CCC(F)(F)CC5)C4=O)nc3)ccn2)cn1] |
| 74 | 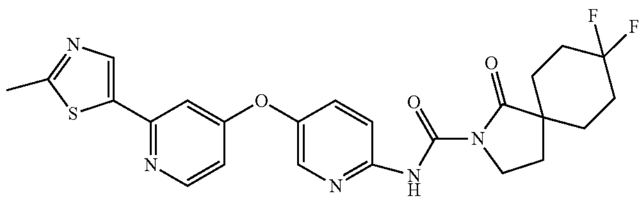 [SMILES: Cc1ncc(-c2cc(Oc3ccc(NC(=O)N4CCC5(CCC(F)(F)CC5)C4=O)nc3)ccn2)s1] |
| 75 | 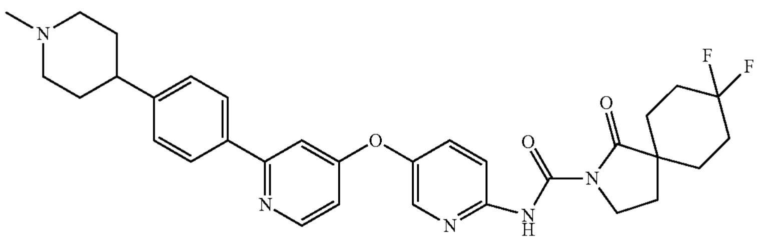 [SMILES: CN1CCC(c2ccc(-c3cc(Oc4ccc(NC(=O)N5CCC6(CCC(F)(F)CC6)C5=O)nc4)ccn3)cc2)CC1] |
| 76 | 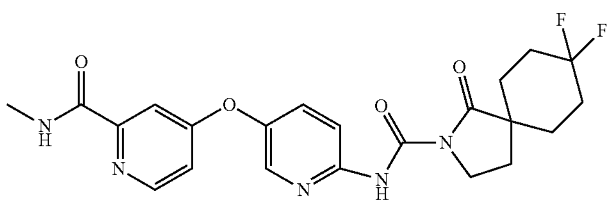 [SMILES: CNC(=O)c1cc(Oc2ccc(NC(=O)N3CCC4(CCC(F)(F)CC4)C3=O)nc2)ccn1] |
| 77 | 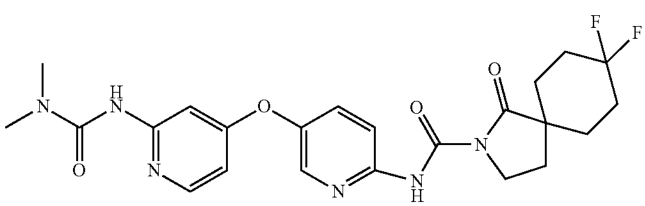 [SMILES: CN(C)C(=O)Nc1cc(Oc2ccc(NC(=O)N3CCC4(CCC(F)(F)CC4)C3=O)nc2)ccn1] |
| 78 | 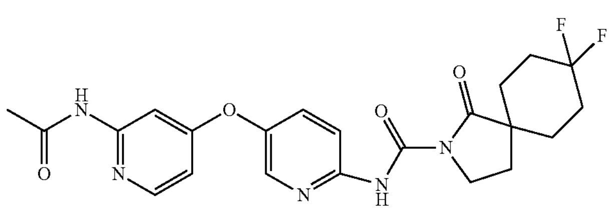 [SMILES: CC(=O)Nc1cc(Oc2ccc(NC(=O)N3CCC4(CCC(F)(F)CC4)C3=O)nc2)ccn1] |
| 79 | 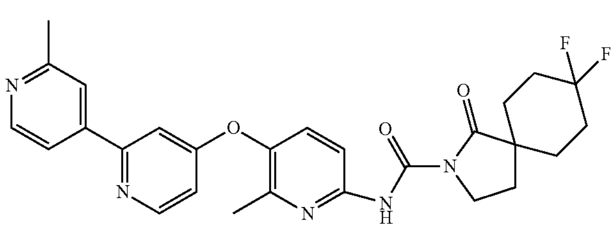 [SMILES: Cc1cc(-c2cc(Oc3ccc(NC(=O)N4CCC5(CCC(F)(F)CC5)C4=O)nc3C)ccn2)ccn1] |

-continued
| NO. | Structure |
|---|---|
| 80 | 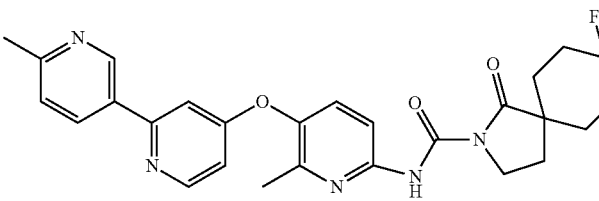 |
| 81 | 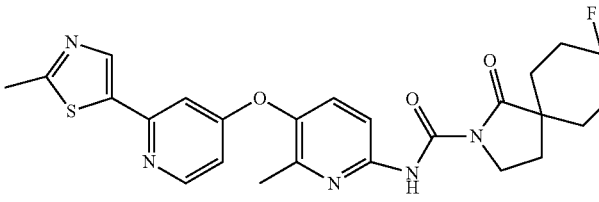 |
| 82 | 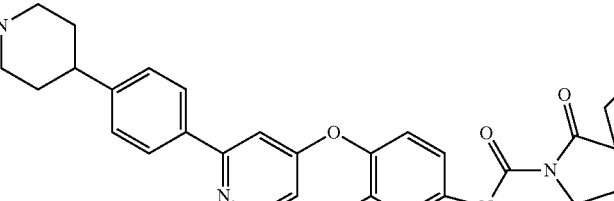 |
| 83 | 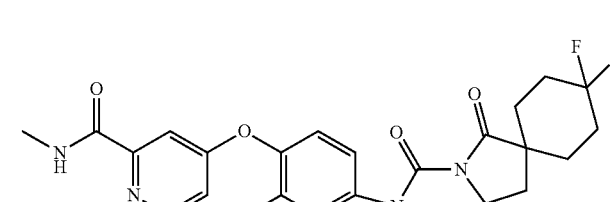 |
| 84 | 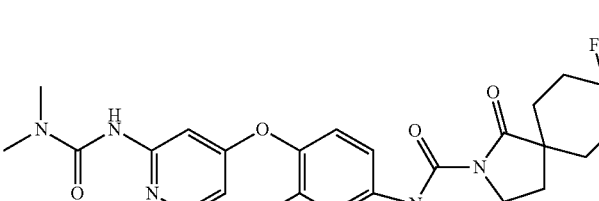 |
| 85 | 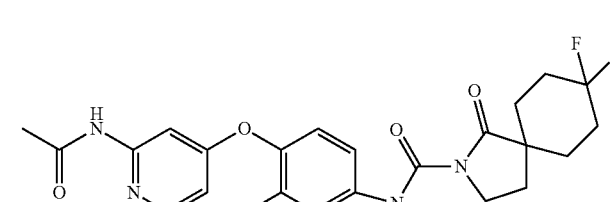 |
| 86 | 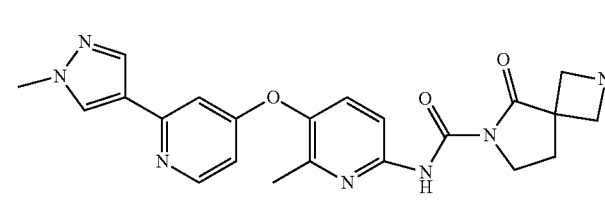 |

-continued

| NO. | Structure |
|---|---|
| 87 | 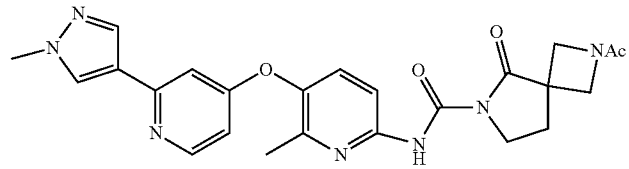 |
| 88 | 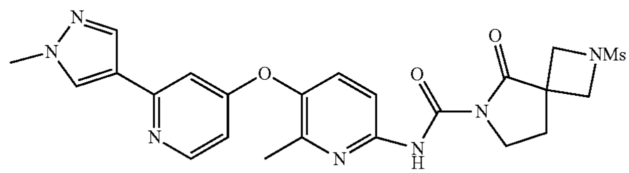 |
| 89 | 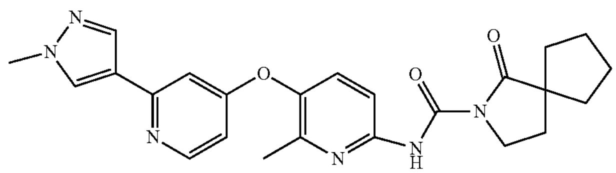 [SMILES: Cc1nc(NC(=O)N2CCC3(CCCC3)C2=O)ccc1Oc1ccnc(-c2cnn(C)c2)c1] |
| 90 | 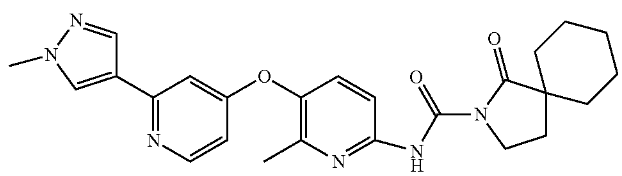 [SMILES: Cc1nc(NC(=O)N2CCC3(CCCCC3)C2=O)ccc1Oc1ccnc(-c2cnn(C)c2)c1] |

The present invention will be further explained below in conjunction with specific embodiments. It should be understood that these embodiments are only used to illustrate the present invention and not to limit the scope of the present invention. The experimental methods that do not indicate specific conditions in the following examples usually follow the conventional conditions or the conditions recommended by the manufacturer. Unless otherwise stated, percentages and parts are calculated by weight.

EXAMPLE

When the preparation route is not included, the relevant intermediates are commercially available (for example from Sigma Aldrich, Alfa).

General Process

The compound represented by the general formula I of the present invention can be prepared by the following method, but the conditions of the method, such as reactants, solvent, base, amount of compound used, reaction temperature, reaction time required, etc. are not limited to the following explanations. The compounds of the present invention can also be conveniently prepared by combining various synthetic methods described in this specification or known in the art, and such combinations can be easily performed by those skilled in the art to which the present invention belongs.

Reaction formula A describes the general synthesis method of compound A4:

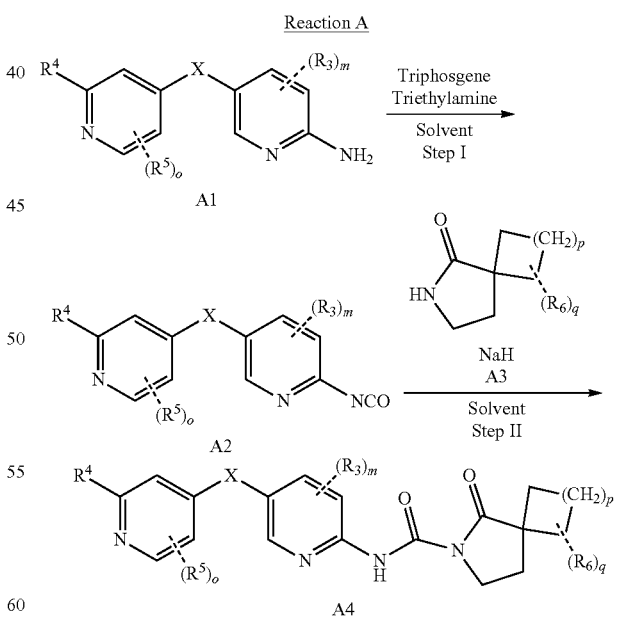

Wherein X, $R^3$, $R^4$, $R^5$, $R^6$, m, and o are as defined above; p is 1, 2 or 3; q is 0, 1, 2, 3 or 4;

Wherein, the solvent in step I and step II is selected from one or any combination of water, methanol, ethanol, THF, DMF, DMSO, dichloromethane, and chloroform.

Reaction formula A1 describes another general synthetic method of compound A4:

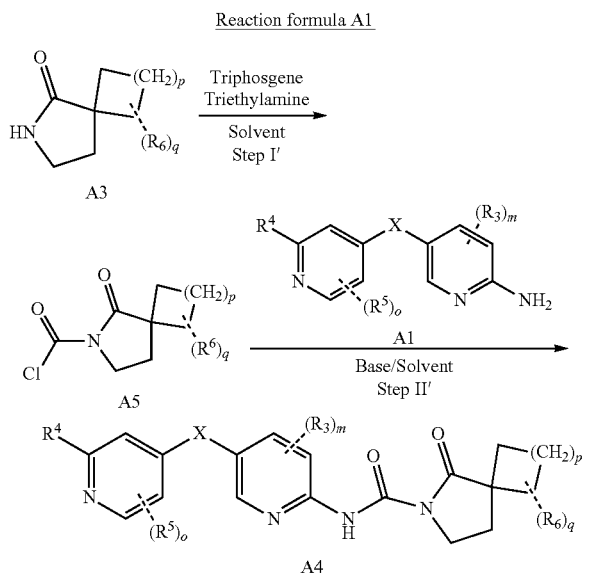

Reaction formula B1 describes the general synthesis method of compound A3:

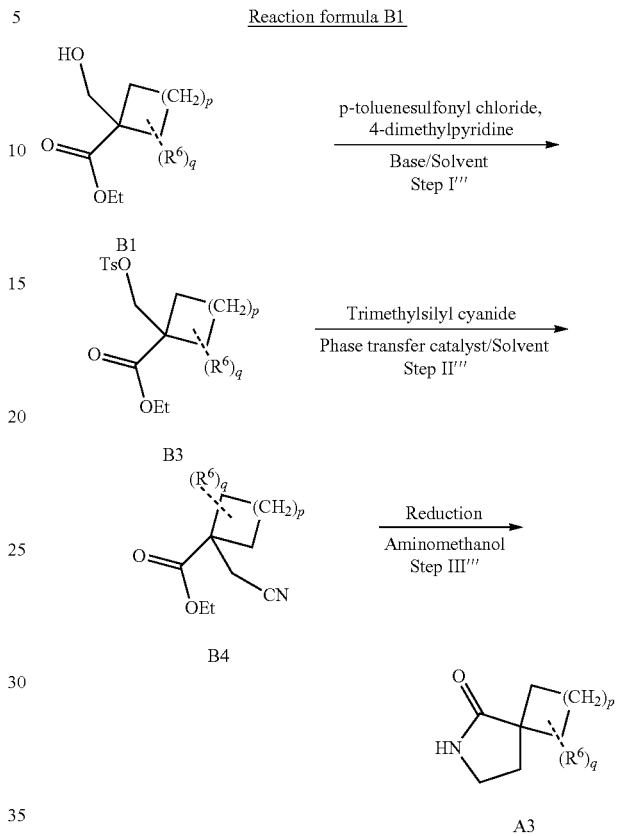

Wherein X, $R^3$, $R^4$, $R^5$, $R^6$, m, and o are as defined above; p is 1, 2 or 3; q is 0, 1, 2, 3 or 4;

Wherein, the solvent in step I' and step II' is selected from one or any combination of water, methanol, ethanol, THF, DMF, DMSO, dichloromethane, and chloroform; the base in step II' is selected from NaOH, NaHCO$_3$, KOH, KHCO$_3$, K$_2$CO$_3$, triethylamine or any combination thereof.

Reaction formula B describes the general synthesis method of compound A3:

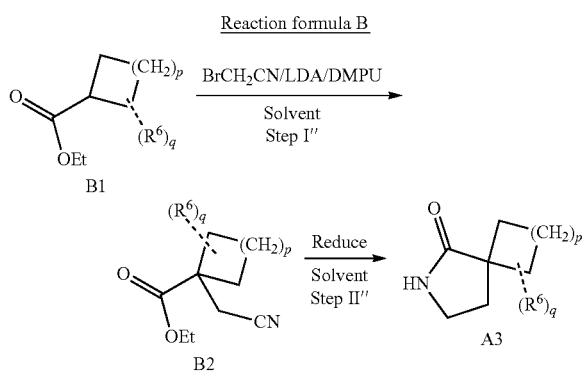

Wherein, p is 1, 2 or 3; q is 0, 1, 2, 3 or 4;

Wherein, the solvent in step I" and step II" is selected from one or any combination of water, methanol, ethanol, THF, DMF, DMSO, dichloromethane, and chloroform; the reaction temperature of step I" is −100° C. to room temperature, preferably −78° C. to room temperature;

The reducing agent used in the reduction reaction in step II' is H2, NaBH4, LiAlH4, and the catalyst used in the reduction reaction is Raney nickel, ferrous chloride, and cobalt chloride; the reaction temperature in step II' is 0° C. to room temperature.

Wherein, p is 1, 2 or 3; q is 0, 1, 2, 3 or 4;

Wherein, the organic solvent in step I''' and step II''' is selected from one or any combination of methanol, ethanol, THF, DMF, DMSO, dichloromethane, and chloroform;

The phase transfer catalyst in step II''' is tetrabutylammonium fluoride, tetrabutylammonium bromide, tetrabutylammonium chloride; cyclic crown ethers: for example: 18 crown 6, 15 crown 5, cyclopaste fine;

Among them, the catalyst used in the reduction reaction of step III''' is Raney nickel, ferrous chloride, and cobalt chloride; and the reducing agent is H$_2$, NaBH$_4$, and LiAlH$_4$.

Use commercially available reagents without further purification. Room temperature refers to 20-27° C. The $^1$H-NMR spectrum was recorded on a Bruker instrument at 400 MHz or 500 MHz. The chemical shift value is expressed in parts per million, that is, the δ value. The following abbreviations are used for the multiplicity of the NMR signal: s=singlet, brs=broad peak, d=doublet, t=triplet, m=multiplet. Coupling constants are listed as J values and measured in Hz. NMR and mass spectrometry results are corrected for background peaks. Chromatography refers to column chromatography performed using 100 mesh silica gel and completed under nitrogen pressure (flash chromatography). The TLC used to monitor the reaction refers to TLC performed using a specific mobile phase and silica gel F254 from Merck as a stationary phase.

The LC/MS experiment is measured under the following conditions:

Instrument: Thermo U3000, ALLtech ELSD, MSQ, UV detector combined with ELSD and MSD (elution ratio 4:1).

Column: Waters X-Bridge C-18, 3.5 μm, 4.6×50 mm; column temperature: 30° C. Gradient [time (min)/solvent B in A (%)]: 0.00/5.0, 0.70/95, 1.40/95, 1.41/5, 1.50/5. (Solvent A=0.01% trifluoroacetic acid in water; Solvent B=0.01% trifluoroacetic acid in acetonitrile). UV detection: 214/254/ 280/300 nm; DAD detection: 200-400 nm; Flow rate: 4 mL/min; MS: ESI, 100-1500 m/z Preparative HPLC usually uses an acidic method (gradient of acetonitrile and water, each containing 0.1% formic acid) with Thermo U3000 AFC-3000; column: Globalsil C-18 12 nm, 250×20 mm, 10 μm, or equivalent; flow rate: 20 mL/min for separation.

Preparation of Compound INT-1

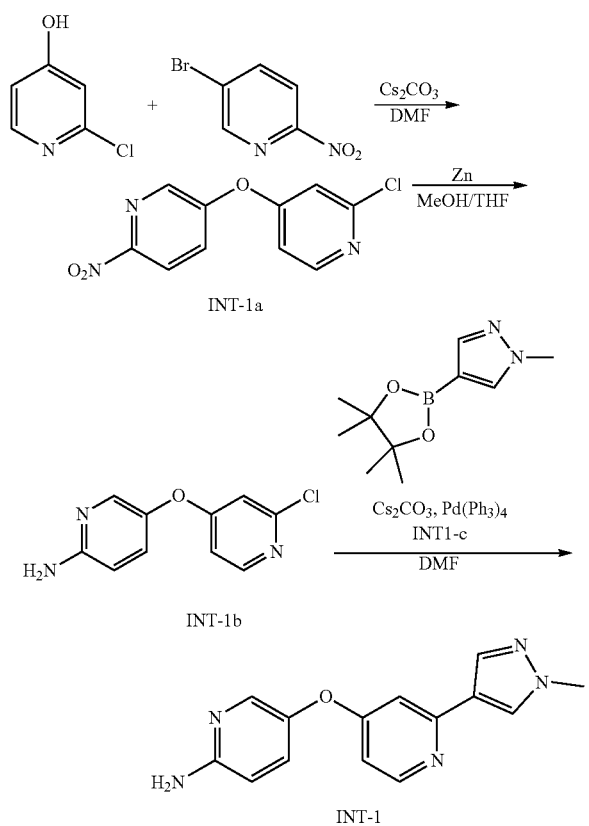

To a solution of 2-chloropyridin-4-ol (70.2 g, 0.54 mol) and 5-bromo-2-nitropyridine (100.0 g, 0.49 mol) in DMF (1.5 L) was added $Cs_2CO_3$ (241.0 g, 0.74 mol). The reaction mixture was stirred at 80° C. for 24 h. Then the reaction was cooled to r.t., filtered and washed with EtOAc. The mixture was concentrated under reduced pressure. The residue was dissolved in 2 L EtOAc, which was washed with $H_2O$ (2 L×2) and brine (1 L×2). The organic layer was dried over $MgSO_4$, filtered and concentrated to give crude compound INT-1a. The crude compound INT-1a was purified by column chromatography on silica gel (petroleum ether: EtOAc=100:1 to 1:1) to afford compound INT-1a (43.5 g, yield 31.9%) as yellow oil. $^1$H NMR (DMSO-$d_6$, 400 MHz) δ 8.64 (s, 1H), 8.47-8.40 (m, 2H), 8.14-8.02 (m, 1H), 7.39 (s, 1H), 7.25 (s, 1H); MS: 252.0 [M+H]$^+$.

To a solution of compound INT-1a (43.5 g, 0.17 mol) and $NH_4Cl$ (91.0 g, 1.7 mol) in THF (500 mL) and MeOH (500 mL) was added Zn (110.5 g, 1.7 mol). The reaction was stirred at room temperature for 16 hours. The reaction was filtered. The filtrate was concentrated to give compound INT-1b (37.3 g, 97.5% yield) as a rbrown solid. MS: 222.0 [M+H]$^+$.

To a solution of compound INT-1b (37.3 g, 0.17 mol) and compound INT-1c (42.0 g, 0.20 mol) in DMF (500 mL) and $H_2O$ (200 mL) was added $Pd(PPh_3)_4$ (9.7 g, 8.4 mmol) and $Cs_2CO_3$ (220 g, 0.67 mol). The reaction was stirred at 90° C. for 24 hours under $N_2$. The reaction was filtered. The filtrate was dissolved in 1 L EtOAc, which was washed with $H_2O$ (1 L×2) and brine (1 L×2). The organic layer was dried over $MgSO_4$, filtered and concentrated to give crude compound INT-1. The crude compound INT-1 was purified by column chromatography on silica gel (petroleum ether: EtOAc=100:1 to 1:1) to afford compound INT-1 (23.5 g, yield 52.2%) as a white solid. $^1$H NMR (DMSO-$d_6$, 400 MHz) δ 8.33 (d, J=5.7 Hz, 1H), 8.25 (s, 1H), 7.95 (s, 1H), 7.82 (d, J=2.7 Hz, 1H), 7.30 (dd, J=8.9, 2.7 Hz, 1H), 7.16 (d, J=2.4 Hz, 1H), 6.59 (dd, J=5.7, 2.4 Hz, 1H), 6.55-6.46 (m, 1H), 6.03 (s, 2H), 3.86 (s, 3H); MS: 268.0 [M+H]$^+$.

Preparation of Compound INT-2

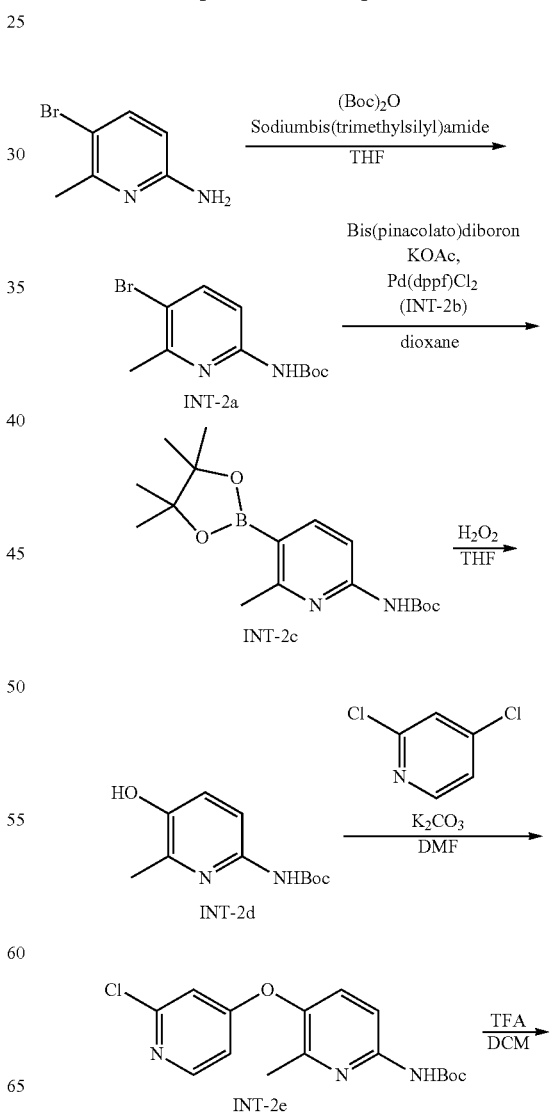

-continued

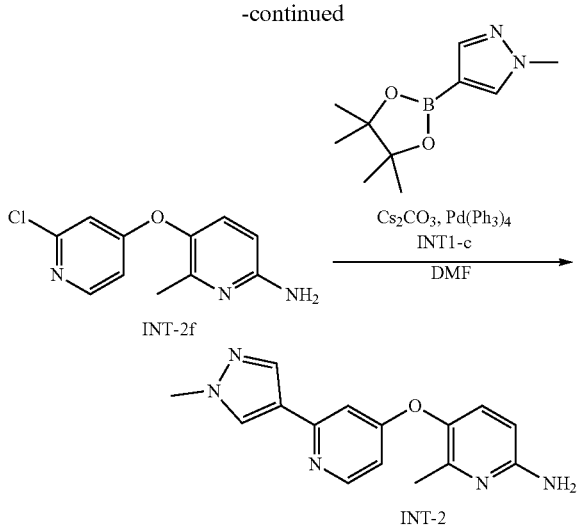

To a solution of 5-bromo-6-methyl-pyridin-2-amine (500 mg, 2.67 mmol) in DCM (10 mL) was added sodium bis(trimethylsilyl)amide (2.0 M, 4.68 mL) under 0° C. The reaction was stirred at room temperature for 1 hour. Then tert-butoxycarbonyl tert-butyl carbonate (700 mg, 3.21 mmol) in THF (5 mL) was added by dropwise. The reaction was stirred at room temperature for 1 hour. LC/MS showed the starting material was consumed. H$_2$O (30 mL) and DCM (20 mL) was added. The mixture was separated. The organic phase was washed with brine (30 mL×2), dried over Na$_2$SO$_4$ and concentrated to give the crude product. The crude product was purified by column chromatography on silica gel (EtOAc/petroleum ether from 0 to 20%) to give INT-2a (582 mg, 75.8% yield) as a white solid.

To a solution of INT-2a (582 mg, 2.03 mmol) and 4,4,5,5-tetramethyl-2-(4,4,5,5-tetramethyl-1,3,2-dioxaborolan-2-yl)-1,3,2-dioxaborolane (669 mg, 2.63 mmol) in dioxane (12 mL) was added INT-2b (148 mg, 2.03 mmol) and KOAc (398 mg, 4.05 mmol). The reaction was stirred at 90° C. for 16 hours under N$_2$. LC/MS showed the starting material was consumed. The reaction was concentrated and purified by column chromatography on silica gel (EtOAc/petroleum ether from 0 to 30%) to give INT-2c (330 mg, 41.9% yield) as a white solid. $^1$H NMR (DMSO-d$_6$, 500 MHz) δ 9.78 (s, 1H), 7.85 (d, J=8.2 Hz, 1H), 7.60 (d, J=8.2 Hz, 1H), 2.50 (s, 3H), 1.43 (s, 9H), 1.27 (s, 12H).

To a solution of INT-2c (330 mg, 0.85 mmol) in THF (3 mL) was added H$_2$O$_2$ (482 mg, 4.25 mmol, 30% w/w) under 0° C. The reaction was stirred for 3 hours at room temperature. 5% aq. Na$_2$SO$_3$ (5 mL) was added under 0° C. EtOAc (30 mL) and H$_2$O (25 mL) was added. The reaction was separated. The organic phase was washed with brine (30 mL×2). The organic was dried over Na$_2$SO$_4$ and concentrated to give the crude product. The crude product was purified by column chromatography on silica gel (EtOAc:petroleum ether=0:100 to 1:3) to give INT-2d (100 mg, 52.2% yield) as a white solid. $^1$H NMR (DMSO-d$_6$, 500 MHz) δ 9.30 (s, 1H), 9.22 (s, 1H), 7.36 (d, J=8.5 Hz, 1H), 7.06 (d, J=8.5 Hz, 1H), 2.21 (s, 3H), 1.43 (s, 9H).

To a solution of compound INT-2d (100 mg, 0.45 mmol) and 2,4-dichloropyridine (86 mg, 0.58 mmol) in DMF (5 mL) was added Cs$_2$CO$_3$ (290 mg, 0.89 mmol). The reaction was stirred at 65° C. for 3 hours. LC/MS showed the starting material was consumed. H$_2$O (20 mL) and EtOAc (20 mL) was added. The mixture was separated. The water layer was extracted with EtOAc (20 mL). The organic layers were combined, which was washed with brine (40 mL×2), dried over Na$_2$SO$_4$ and concentrated to give the crude product. The crude product was purified by preparative TLC (EtOAc:petroleum ether=1:4) to give INT-2e (60 mg, 40% yield) as a yellow solid.

To a solution of INT-2e (60 mg, 0.18 mmol) in DCM (2 mL) was added TFA (0.5 mL). The reaction was stirred at room temperature for 3 hours. LC/MS showed the reaction was worked well. The reaction was concentrated. DCM (10 mL) and 5% aq. NaHCO$_3$ (10 mL) was added. The reaction was separated. The organic was concentrated to give INT-2f (35 mg, 83% yield) as white solid. $^1$H NMR (DMSO-d$_6$, 500 MHz) δ 8.24 (d, J=5.8 Hz, 1H), 7.31 (d, J=8.4 Hz, 1H), 6.93 (s, 1H), 6.88 (dd, J=5.8, 1.9 Hz, 1H), 6.43 (d, J=8.4 Hz, 1H), 2.06 (s, 3H).

Compound INT-2 was prepared using the similar procedures as described for compound INT-1 using compound INT-2f to replace compound INT-1b. $^1$H NMR (DMSO-d$_6$, 500 MHz) δ 8.38 (d, J=6.0 Hz, 1H), 7.87 (s, 1H), 7.25 (s, 1H), 7.21 (d, J=8.7 Hz, 1H), 6.93 (d, J=2.3 Hz, 1H), 6.64-6.57 (m, 1H), 6.47 (d, J=8.7 Hz, 1H), 3.94 (s, 3H), 2.28 (s, 3H); MS: 282.7 [M+H]$^+$.

Preparation of Compound INT-3

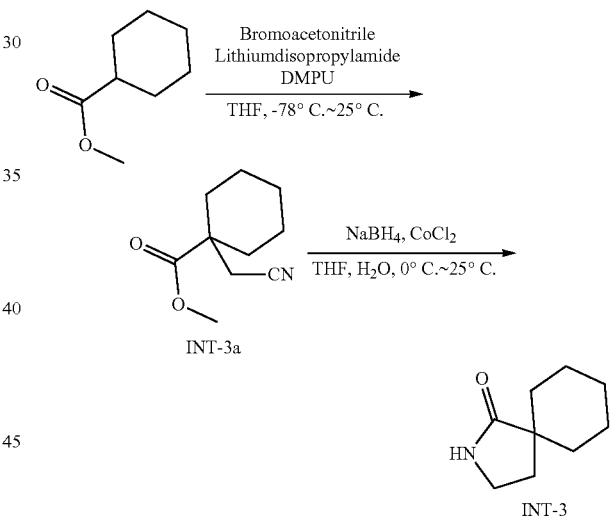

A solution of methyl cyclohexane carboxylate (2.0 g, 14.1 mmol) in dry THF (30 mL), The mixture was cooled to −78° C. Then LDA (2.0 M in THF, 7.8 mL) was added dropwise. The reaction was stirred at −78° C. for 1.5 hour. A solution of 2-bromoacetonitrile (2.0 g, 16.9 mmol) and DMPU (0.90, 7.0 mmol) in THF (10 mL) was added dropwise while keeping the inner temperature at −78° C. The reaction was then warmed up to room temperature and stirred for overnight. TLC showed the starting material was consumed. 1N HCl (20 mL) was added. The volatiles were removed, and the resulting aqueous layer was extracted with EtOAc (20 mL×3). The combine organic phase was washed with brine (50 mL×2), dried with sodium sulfate and concentrated to give the crude product. The crude product was purified by chromatography on silica gel (EtOAc:petroleum ether=1:15) to give compound INT-3a (1.10 g, 43% yield) as yellow oil. $^1$H NMR (CDCl$_3$, 400 MHz) δ 3.67 (s, 3H), 2.70 (s, 2H), 1.96-1.92 (m, 2H), 1.56-1.50 (m, 2H), 1.47-1.27 (m, 6H).

To a solution of compound INT-3a (1.0 g, 5.52 mmol) and CoCl$_2$ (0.36 g, 2.76 mmol) in H$_2$O (10 ml) and THF (20 mL) was added NaBH$_4$ (1.04 g, 27.6 mmol) in portions under 0° C. The reaction was then warmed up to room temperature and stirred for 16 hours. CoCl$_2$ (0.18 g, 1.38 mmol) and NaBH$_4$ (0.50 g, 13.8 mmol) was further added and the reaction was stirred at room temperature for another 16 hours. The reaction was filtered and the filtrate was concentrated. The residue was re-dissolved by EtOAc (100 mL), which was washed with brine (100 mL×2), dried with sodium sulfate and concentrated to give the crude product. The crude product was purified by chromatography on silica gel (EtOAc/petroleum ether=1/3) to give compound INT-3 (230 mg, 27% yield) as a white solid. $^1$H NMR (CDCl$_3$, 400 MHz) δ 5.95 (brs, 1H), 3.30 (t, J=6.8 Hz, 2H), 2.03 (t, J=7.2 Hz, 2H), 1.74-1.62 (m, 5H), 1.46-1.44 (m, 2H), 1.38-1.26 (m, 3H).

Compounds INT-4, INT-5, INT-6, INT-7, INT-8 was prepared using the similar procedures as described for synthesis of compound INT-3. The corresponding spectral information was shown in the following table:

| Structure | Data |
|---|---|
| 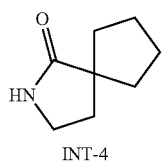<br>INT-4 | White solid; $^1$H NMR (CDCl$_3$, 400 MHz) δ 5.60 (brs, 1H), 3.30 (t, J = 6.8 Hz, 2H), 2.00 (t, J = 6.8 Hz, 2H), 1.96-1.90 (m, 2H), 1.83-1.76 (m, 2H), 1.67-1.62 (m, 2H), 1.58-1.53 (m, 2H) |
| 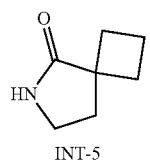<br>INT-5 | White solid; $^1$H NMR (CDCl$_3$, 400 MHz) δ 6.21 (br s, 1H), 3.20 (t, J = 6.8 Hz, 2H), 2.42-2.31 (m, 2H), 2.17 (t, J = 6.8 Hz, 2H), 2.02-1.78 (m, 4H) |
| 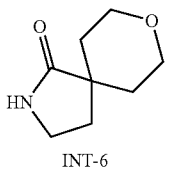<br>INT-6 | Pale yellow solid; $^1$H NMR (CDCl$_3$, 400 MHz) δ 5.65 (s, 1H), 4.00-3.97 (m, 2H), 3.56-3.45 (m, 2H), 3.35 (t, J = 6.8 Hz, 2H), 2.12 (t, J = 6.8 Hz, 2H), 2.01-1.95 (m, 2H), 1.39-1.35 (m, 2H). |
| 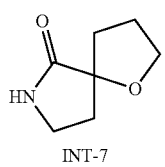<br>INT-7 | Brown solid; $^1$H NMR (CDCl$_3$, 400 MHz) δ 5.93 (br s, 1H), 4.06-3.98 (m, 1H), 3.97-3.93 (m, 1H), 3.45-3.39 (m, 1H), 3.29-3.23 (m, 1H), 2.30-2.08 (m, 4H), 1.99-1.89 (m, 1H), 1.88-1.81 (m, 1H). |
| 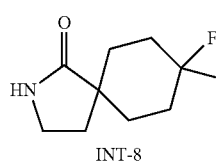<br>INT-8 | White solid; $^1$H NMR (DMSO-d$_6$, 500 MHz) δ 7.58 (br s, 1H), 3.13 (t, J = 6.5 Hz, 2H), 2.20-2.00 (m, 2H), 1.92 (t, J = 6.5 Hz, 2H), 1.85-1.75 (m, 2H), 1.70-1.64 (m, 2H), 1.48-1.42 (m, 2H). |

Preparation of Compound INT-9

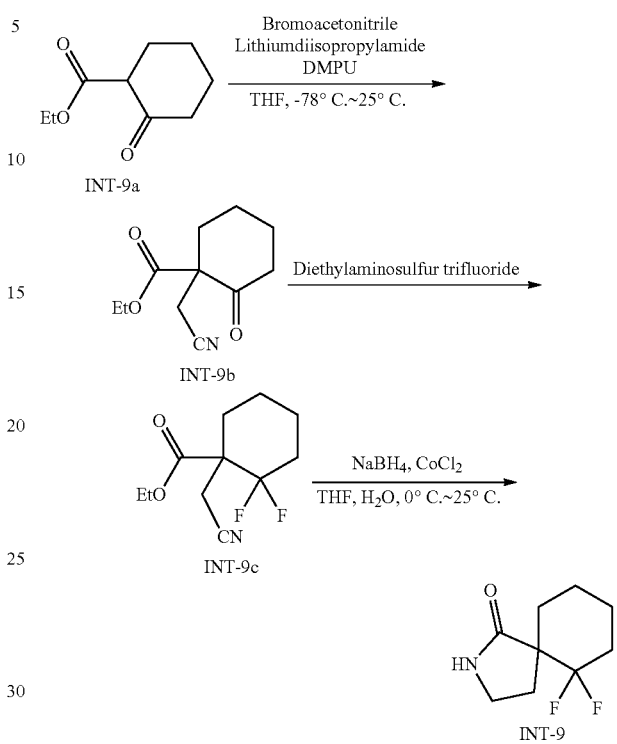

Compound INT-9b was prepared from starting material INT-9a using the similar procedures as described for synthesis of compound INT-3a.

A solution of Compound INT-9b (1.60 g, 7.65 mmol) in diethylaminosulfur trifluoride (3 mL). The reaction was stirred at room temperature for 16 hours. Ice water (20 mL) was added to the reaction slowly, Followed by the addition of 5% aq. NaHCO$_3$ to adjust pH to 8-9. The resulting mixture was extracted with EtOAc (50 mL×3). The organic phase was combined, washed with brine (100 mL×2), dried with sodium sulfate and concentrated to give the crude product. The crude product was purified by chromatography on silica gel (EtOAc:petroleum ether=1:5) to give compound INT-9c (1.00 g, 57% yield) as colorless oil. MS: 232.3 [M+H]$^+$.

Compound INT-9 as pale yellow solid was prepared from starting material INT-9c using the similar procedures as described for synthesis of compound INT-3. $^1$HNMR (CDCl$_3$, 400 MHz) δ 5.64 (brs, 1H), 3.34-3.16 (m, 2H), 2.65-2.55 (m, 1H), 2.50-2.29 (m, 1H), 1.98-1.68 (m, 5H), 1.43-1.33 (m, 1H).

Compounds INT-10, INT-11 was prepared using the similar procedures as described for synthesis of compound INT-9. The corresponding spectral information was shown in the following table:

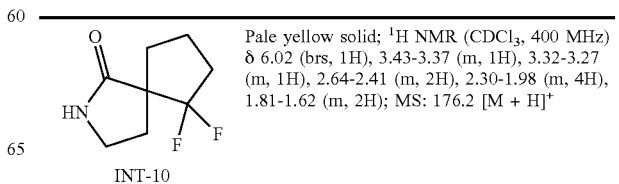

INT-10 — Pale yellow solid; $^1$H NMR (CDCl$_3$, 400 MHz) δ 6.02 (brs, 1H), 3.43-3.37 (m, 1H), 3.32-3.27 (m, 1H), 2.64-2.41 (m, 2H), 2.30-1.98 (m, 4H), 1.81-1.62 (m, 2H); MS: 176.2 [M + H]$^+$

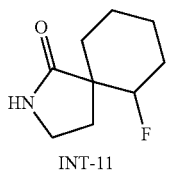

Pale yellow solid; ¹H NMR (CDCl₃, 400 MHz) δ 6.11 (brs, 1H), 4.83-4.67 (m, 1H), 3.37-3.28 (m, 2H), 2.39-2.35 (m, 1H), 2.07-1.95 (m, 2H), 1.77-1.65 (m, 3H), 1.62-1.31 (m, 3H); MS: 172.3 [M + H]⁺.

INT-11

Preparation of Compound INT-12

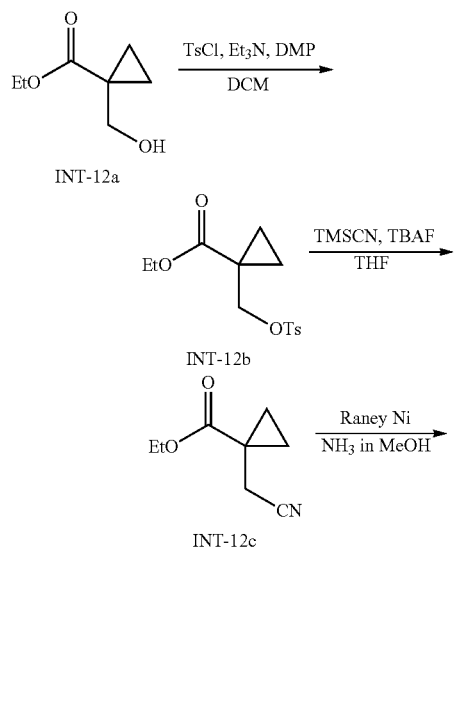

To a solution of compound INT-12a (700 mg, 4.86 mmol), DMAP (59 mg, 0.49 mmol) and Et₃N (9.71 mmol, 1.36 mL) in DCM (10 mL) was added 4-methylbenzenesulfonyl chloride (1.11 g, 5.83 mmol). The reaction was stirred at room temperature for 16 hours. TLC (EtOAc:petroleum ether=1:5) showed the starting material was consumed. DCM (20 mL) and H₂O (40 mL) was added and the organic phase was washed with brine (40 mL×2), dried over Na₂SO₄ and concentrated to give the crude product. The crude product was purified by chromatography on silica gel (EtOAc: petroleum ether from 0 to 30%) to give compound INT-12b (1.0 g, 69% yield) as colorless oil. ¹H NMR (500 MHz, DMSO-d₆) δ 7.78 (d, J=8.2 Hz, 2H), 7.49 (d, J=8.2 Hz, 2H), 4.15 (s, 2H), 3.97 (q, J=7.0 Hz, 2H), 2.43 (s, 3H), 1.17 (brs, 2H), 1.07 (t, J=7.0 Hz, 3H), 0.99 (brs, 2H); MS: 299.4 [M+H]⁺.

To a solution of compound INT-12b (1.22 g, 4.1 mmol) and trimethylsilylformonitrile (1.22 g, 12.3 mmol) in THF (15 mL) was added TBAF (1 M in THF, 12.3 mL). The reaction was stirred at room temperature for 16 hours. TLC showed the starting material was consumed. EtOAc (50 mL) and H₂O (50 mL) was added and the organic phase was washed with brine (50 mL×2), dried over Na₂SO₄ and concentrated to give the crude product. The crude product was purified by chromatography on silica gel (EtOAc/petroleum ether from 0 to 25%) to give compound INT-12b (500 mg, 80% yield) as pale yellow oil. ¹H NMR (500 MHz, DMSO-d₆) δ 4.10 (q, J=7.1 Hz, 2H), 2.79 (s, 2H), 1.19 (brs, 2H), 1.18 (t, J=7.1 Hz, 3H), 1.00 (brs, 2H).

To a solution of compound INT-12b (100 mg, 0.65 mmol) in methanol solution of ammonia (7 M in MeOH, 3 mL) was added Raney Ni (100 mg, 0.65 mmol). The mixture was stirred for 48 hours under H₂ balloon at room temperature. After filtration, the filtrate was concentrated to give the crude product. The crude product was purified by chromatography on silica gel (DCM:MeOH from 0 to 10%) to give compound INT-12 (34 mg, 47% yield) as a white solid. ¹H NMR (500 MHz, DMSO-d₆) δ 7.54 (s, 1H), 3.29 (t, J=7.1 Hz, 2H), 2.08 (t, J=7.1 Hz, 2H), 0.78 (brs, 2H), 0.67 (brs, 2H).

Preparation of Compound INT-13

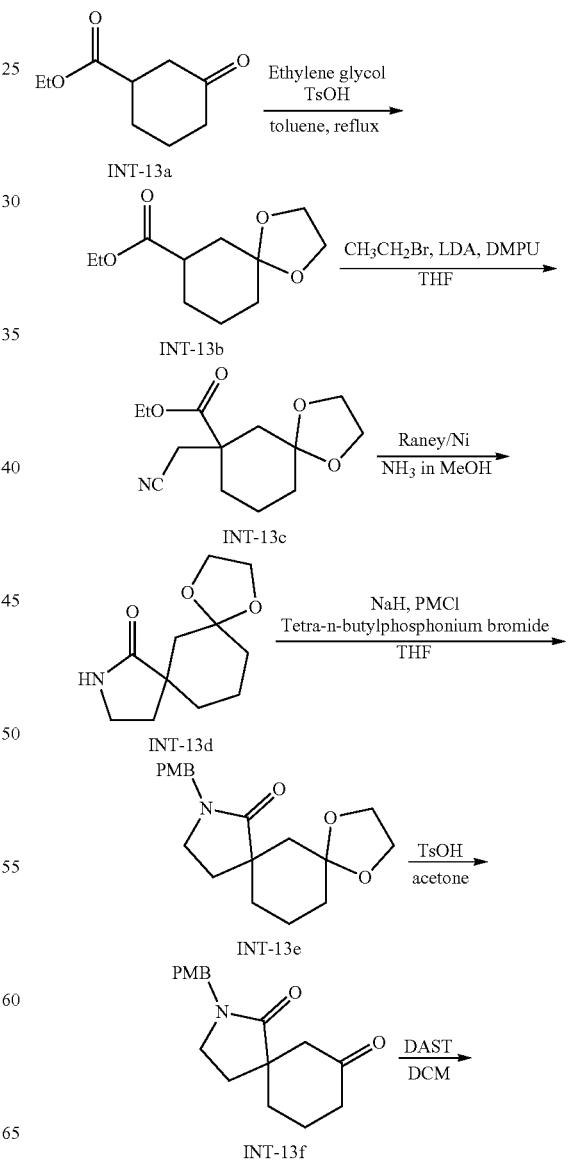

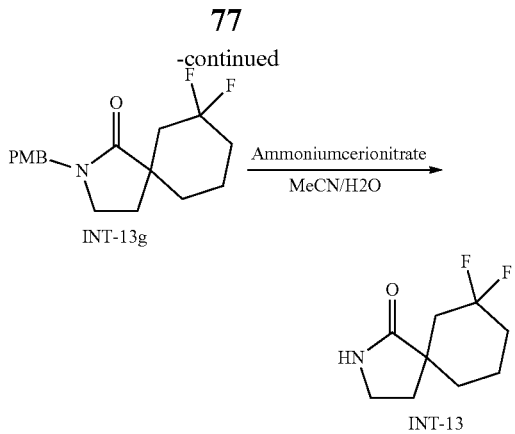

To a solution of compound INT-13a (1.03 g, 6.06 mmol) and Ethylene glycol (0.45 g, 7.27 mmol) in toluene (100 mL) was added TsOH (57 mg, 0.30 mmol). The reaction was refluxed for 16 hours. 5% aq. NaHCO$_3$ (100 mL) and EtOAc (100 mL) was then added and the aqueous layer was further extracted with EtOAc (100 mL). The organic layers were combined, washed with brine, dried over Na$_2$SO$_4$, filtered and concentrated under reduced pressure. The residue was purified by chromatography on silica gel (petroleum ether:EtOAc=10:1) to give compound INT-13b (1.09 g, 84% yield) as pale yellow oil; MS: 215.4 [M+H]$^+$.

Compound INT-13c as pale yellow oil was prepared from starting material INT-13b using the similar procedures as described for synthesis of compound INT-3a; MS: 254.3 [M+H]$^+$.

Compound INT-13d as a white solid was prepared from starting material INT-13c using the similar procedures as described for synthesis of compound INT-12; $^1$H NMR (400 MHz, CDCl$_3$) δ 6.23 (brs, 1H), 3.94 (s, 4H), 3.31-3.27 (m, 2H), 2.40-2.25 (m, 1H), 2.15-2.00 (m, 1H), 1.99-1.93 (m, 1H), 1.85-1.70 (m, 2H), 1.69-1.64 (m, 1H), 1.60-1.45 (m, 4H); MS: 212.4 [M+H]$^+$.

To a solution of compound INT-13d (430 mg, 2.04 mmol) in THF (10 mL) was added NaH (122 mg, 3.06 mmol, 60% w/w). The reaction was stirred at room temperature for 30 minutes. Then PMBCl (383 mg, 2.45 mmol) and Tetra-n-butylphosphonium bromide (69 mg, 0.20 mmol) was added. The reaction was stirred at room temperature for 16 hours. H$_2$O (50 mL) and EtOAc (50 mL) was then added and the aqueous layer was further extracted with EtOAc (50 mL). The organic layers were combined, washed with brine, dried over Na$_2$SO$_4$, filtered and concentrated under reduced pressure. The residue was purified by chromatography on silica gel (petroleum ether:EtOAc=1:1) to give compound INT-13e (555 mg, 82% yield) as pale yellow oil; MS: 332.2 [M+H]$^+$.

To a solution of compound INT-13e (555 mg, 1.68 mmol) in acetone (10 mL) was added TsOH (32 mg). The reaction was stirred at room temperature for 16 hours. 5% aq. NaHCO$_3$ (50 ml) and EtOAc (50 mL) was then added and the aqueous layer was further extracted with EtOAc (50 mL). The organic layers were combined, washed with brine, dried over Na$_2$SO$_4$, filtered and concentrated under reduced pressure. The residue was purified by chromatography on silica gel (petroleum ether:EtOAc=1:1) to give compound INT-13f (444 mg, 92% yield) as colorless oil; MS: 288.3 [M+H]$^+$.

To a solution compound INT-13f (44 mg, 1.55 mmol) in DCM (10 mL) was added diethylaminosulfur trifluoride (2.49 g, 15.5 mmol). The reaction was stirred at room temperature for 16 hours. 5% aq. NaHCO$_3$ (50 mL) and EtOAc (50 mL) was then added and the aqueous layer was further extracted with EtOAc (50 mL). The organic layers were combined, washed with brine, dried over Na$_2$SO$_4$, filtered and concentrated under reduced pressure. The residue was purified by chromatography on silica gel (petroleum ether:EtOAc=2:1) to give compound INT-13g (410 mg, 86% yield) as pale yellow oil; MS: 310.3 [M+H]$^+$.

To a solution of compound INT-13g (410 mg, 1.33 mmol) in MeCN (15 mL) was added ammonium ceric nitrate (3.64 g, 6.63 mmol) in H$_2$O (3 mL). The reaction was stirred at room temperature for 16 hours. 5% aq. NaHCO$_3$ (50 mL) and EtOAc (50 mL) was added and the aqueous layer was further extracted with EtOAc (50 mL). The organic layers were combined, washed with brine, dried over Na$_2$SO$_4$, filtered and concentrated under reduced pressure. The residue was purified by chromatography on silica gel (petroleum ether:EtOAc=2:1 to 0:1) to give compound INT-13 (132 mg, 53% yield) as pale yellow solid; $^1$H NMR (400 MHz, CDCl$_3$) δ 6.03 (brs, 1H), 3.40-3.26 (m, 2H), 2.25-2.04 (m, 4H), 1.95-1.80 (m, 2H), 1.80-1.60 (m, 4H); MS: 190.1 [M+H]$^+$.

Compounds INT-14, INT-15 was prepared using the similar procedures as described for synthesis of compound INT-13. The corresponding spectral information was shown in the following table:

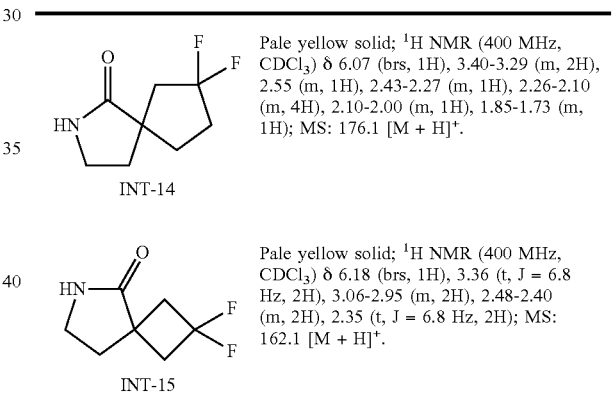

INT-14: Pale yellow solid; $^1$H NMR (400 MHz, CDCl$_3$) δ 6.07 (brs, 1H), 3.40-3.29 (m, 2H), 2.55 (m, 1H), 2.43-2.27 (m, 1H), 2.26-2.10 (m, 4H), 2.10-2.00 (m, 1H), 1.85-1.73 (m, 1H); MS: 176.1 [M + H]$^+$.

INT-15: Pale yellow solid; $^1$H NMR (400 MHz, CDCl$_3$) δ 6.18 (brs, 1H), 3.36 (t, J = 6.8 Hz, 2H), 3.06-2.95 (m, 2H), 2.48-2.40 (m, 2H), 2.35 (t, J = 6.8 Hz, 2H); MS: 162.1 [M + H]$^+$.

Preparation of Compound 1

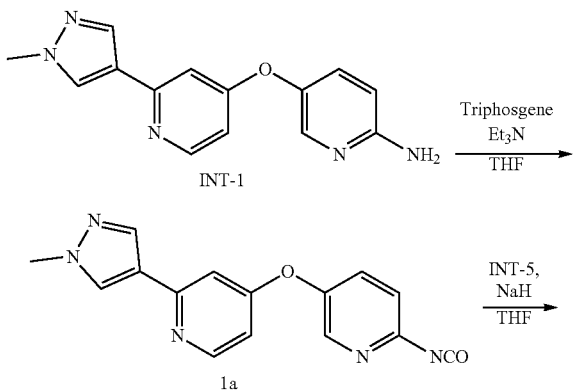

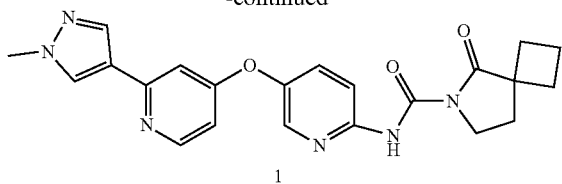

1

To a solution of compound INT-1 (107 mg, 0.40 mmol) and Et₃N (222 µL, 1.60 mmol) in THF (5 mL) was added triphosgene (95 mg, 0.32 mmol) in THF (2 mL) under 0° C. The reaction was stirred at room temperature for 1 hour. LC/MS showed the starting material was consumed. The reaction was concentrated and the residue was re-dissolved in a mixture of H₂O (15 mL) and DCM:MeOH=10:1 (v/v, 15 mL) The resulting organic layer was washed with brine (15 mL×2), dried over Na₂SO₄, filtered and concentrated under reduced pressure to give compound 1a, which was used for next step directly.

To a solution of compound INT-5 (50 mg, 0.4 mmol) in THF (5 mL) was added NaH (122 mg, 3.06 mmol, 60% w/w) under 0° C. The reaction was stirred at room temperature for 0.5 hour. Then compound 1a in THF (3 ml) was added and the reaction was stirred at room temperature for 1 hour. LC/MS showed the compound 1a was consumed. H₂O (0.5 mL) was added to quench the reaction. The volatiles were removed and the residue was re-dissolved in a mixture of DCM (15 mL) and H₂O (15 mL) The resulting organic layer was washed with brine (15 mL×2), dried over Na₂SO₄, filtered and concentrated under reduced pressure. The residue was purified by preparative TLC (DCM:MeOH=20:1) to give compound 1 as a white solid; ¹H NMR (DMSO-d₆, 500 MHz) δ 11.09 (s, 1H), 8.37 (d, J=5.0 Hz, 1H), 8.28 (s, 1H), 8.26 (s, 1H), 8.07 (d, J=9.0 Hz, 1H), 7.96 (s, 1H), 7.78-7.72 (m, 1H), 7.23 (s, 1H), 6.70 (d, J=5.0 Hz, 1H), 3.84 (s, 3H), 3.69 (t, J=6.5 Hz, 2H), 2.40-2.25 (m, 2H), 2.18 (t, J=6.5 Hz, 2H), 2.05-1.85 (m, 4H); MS: 419.5 [M+H]⁺.

Compounds 2, 3, 4, 5, 6, 7, 8, 9, 10, 24, 25, 26 was prepared using the similar procedures as described for synthesis of compound 1. The corresponding spectral information was shown in the following table:

| | |
|---|---|
| 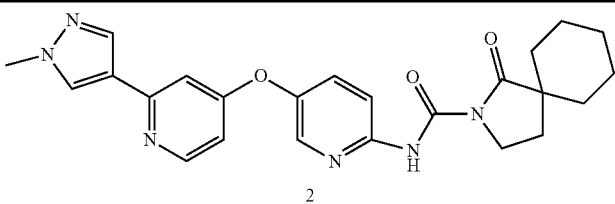<br>2 | ¹H NMR (DMSO-d₆, 500 MHz) δ 11.11 (s, 1H), 8.37 (d, J = 6.0 Hz, 1H), 8.27 (d, J = 2.5 Hz, 1H), 8.26 (s, 1H), 8.07 (d, J = 9.0 Hz, 1H), 7.96 (s, 1H), 7.76 (dd, J = 9.0, 2.5 Hz, 1H), 7.23 (d, J = 2.5 Hz, 1H), 6.70 (dd, J = 6.0, 2.5 Hz, 1H), 3.84 (s, 3H), 3.75 (t, J = 7.0 Hz, 2H), 1.96 (t, J = 7.0 Hz, 2H), 1.69-1.47 (m, 6H), 1.39-1.19 (m, 4H); MS: 447.4 [M + H]⁺. |
| 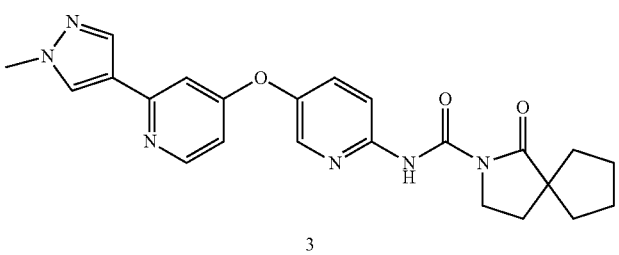 [SMILES: Cn1cc(-c2cc(Oc3ccc(NC(=O)N4CCC5(CCCC5)C4=O)nc3)ccn2)cn1]<br>3 | ¹H NMR (DMSO-d₆, 500 MHz) δ 11.09 (s, 1H), 8.37 (d, J = 5.5 Hz, 1H), 8.27 (d, J = 3.0 Hz, 1H), 8.26 (s, 1H), 8.08 (d, J = 9.0 Hz, 1H), 7.96 (s, 1H), 7.76 (dd, J = 9.0, 3.0 Hz, 1H), 7.23 (d, J = 3.0 Hz, 1H), 6.69 (dd, J = 5.5, 3.0 Hz, 1H), 3.84 (s, 3H), 3.75 (t, J = 6.5 Hz, 2H), 1.93 (t, J = 6.5 Hz, 2H), 1.90-1.82 (m, 2H), 1.75-1.64 (m, 6H); MS: 433.4 [M + H]⁺. |
| 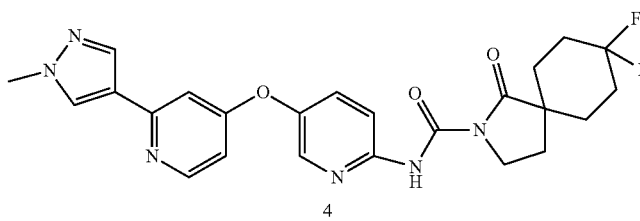<br>4 | 1H NMR (DMSO-d₆, 500 MHz) δ 11.04 (s, 1H), 8.39 (d, J = 5.5 Hz, 1H), 8.29 (d, J = 2.5 Hz, 1H), 8.27 (s, 1H), 8.09 (d, J = 9.0 Hz, 1H), 7.98 (s, 1H), 7.77 (dd, J = 9.0, 2.5 Hz, 1H), 7.25 (d, J = 2.5 Hz, 1H), 6.71 (dd, J = 5.5, 2.5 Hz, 1H), 3.86 (s, 3H), 3.81 (t, J = 7.0 Hz, 2H), 2.18-2.08 (m, 2H), 2.05 (t, J = 7.0 Hz, 2H), 2.01-1.88 (m, 2H), 1.86-1.74 (m, 4H); MS: 483.3 [M + H]⁺. |
| 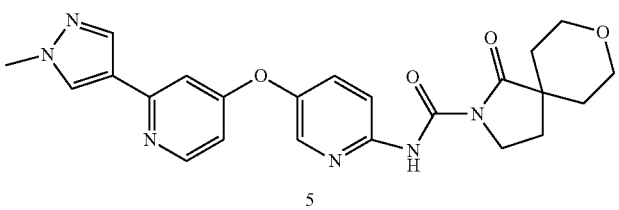 [SMILES: Cn1cc(-c2cc(Oc3ccc(NC(=O)N4CCC5(CCOCC5)C4=O)nc3)ccn2)cn1]<br>5 | ¹H NMR (CDCl₃, 500 MHz) δ 11.13 (s, 1H), 8.41 (d, J = 5.5 Hz, 1H), 8.19 (d, J = 2.5 Hz, 1H), 8.17 (d, J = 9.0 Hz, 1H), 7.86 (s, 1H), 7.48 (dd, J = 9.0, 2.5 Hz, 1H), 7.25 (d, J = 2.5 Hz, 1H), 7.00 (s, 1H), 6.73-6.67 (m, 1H), 4.03-4.00 (m, 2H), 3.98 (s, 3H), 3.89 (t, J = 7.0 Hz, 2H), 3.62-3.56 (m, 2H), 2.08 (t, J = 7.0 Hz, 2H), 2.06-2.02 (m, 2H), 1.53-1.48 (m, 2H); MS: 449.4 [M + H]⁺. |

-continued

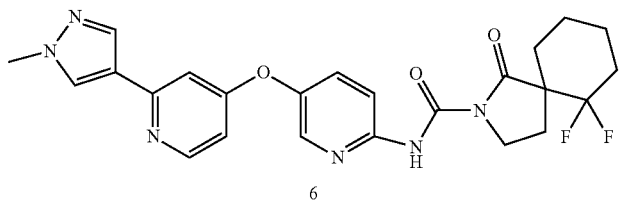 [SMILES: Cn1cc(-c2cc(Oc3ccc(NC(=O)N4CCC5(CCCCC5(F)F)C4=O)nc3)ccn2)cn1]

6

¹H NMR (CDCl₃, 500 MHz) δ 11.12 (s, 1H), 8.44 (d, J = 5.5 Hz, 1H), 8.24-8.20 (m, 2H), 7.88 (s, 1H), 7.51 (d, J = 9.0 Hz, 1H), 7.25 (s, 1H), 7.05 (s, 1H), 6.80-6.74 (m, 1H), 4.03-4.00 (m, 2H), 3.97 (s, 3H), 3.95-3.91 (m, 1H), 3.86-3.80 (m, 1H), 2.68-2.58 (m, 1H), 2.51-2.38 (m, 1H), 2.13-2.01 (m, 2H), 1.92-1.80 (m, 2H), 1.75-1.60 (m, 4H); MS: 483.5 [M + H]⁺.

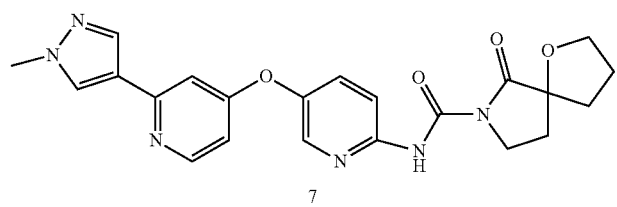 [SMILES: Cn1cc(-c2cc(Oc3ccc(NC(=O)N4CCC5(CCCO5)C4=O)nc3)ccn2)cn1]

7

¹H NMR (CDCl₃, 500 MHz) δ 11.05 (s, 1H), 8.43 (d, J = 5.5 Hz, 1H), 8.24-8.20 (m, 2H), 7.88 (s, 1H), 7.50 (d, J = 8.5 Hz, 1H), 7.25 (s, 1H), 7.00 (s, 1H), 6.78-6.72 (m, 1H), 4.08-4.04 (m, 2H), 3.96 (s, 3H), 3.94-3.88 (m, 1H), 3.81-3.75 (m, 1H), 2.34-2.20 (m, 3H), 2.17-2.09 (m, 1H), 2.09-2.00 (m, 1H), 2.00-1.90 (m, 1H); MS: 435.5 [M + H]⁺.

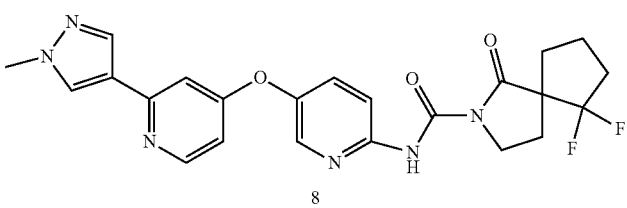 [SMILES: Cn1cc(-c2cc(Oc3ccc(NC(=O)N4CCC5(CCCC5(F)F)C4=O)nc3)ccn2)cn1]

8

¹H NMR (DMSO-d₆, 500 MHz) δ 10.92 (s, 1H), 8.40 (d, J = 5.5 Hz, 1H), 8.31 (d, J = 3.0 Hz, 1H), 8.28 (s, 1H), 8.10 (d, J = 9.0 Hz, 1H), 7.98 (s, 1H), 7.80 (dd, J = 9.0, 3.0 Hz, 1H), 7.25 (d, J = 2.5 Hz, 1H), 6.73 (dd, J = 5.5, 2.5 Hz, 1H), 3.87 (s, 3H), 3.82-3.72 (m, 2H), 2.45-2.20 (m, 4H), 2.08-2.03 (m, 1H), 1.98-1.75 (m, 3H); MS: 469.5 [M + H]⁺.

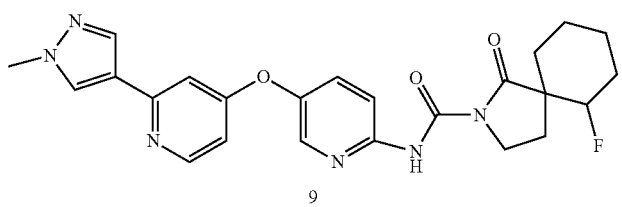 [SMILES: Cn1cc(-c2cc(Oc3ccc(NC(=O)N4CCC5(CCCCC5F)C4=O)nc3)ccn2)cn1]

9

¹H NMR (DMSO-d₆, 500 MHz) δ 11.06 (s, 1H), 8.41 (d, J = 5.5 Hz, 1H), 8.31 (d, J = 3.0 Hz, 1H), 8.29 (s, 1H), 8.10 (d, J = 9.0 Hz, 1H), 7.99 (s, 1H), 7.79 (dd, J = 9.0, 3.0 Hz, 1H), 7.26 (d, J = 2.0 Hz, 1H), 6.74 (dd, J = 5.5, 2.0 Hz, 1H), 4.86-4.73 (m, 1H), 3.87 (s, 3H), 3.84-3.79 (m, 2H), 2.21-2.18 (m, 1H), 2.03-1.99 (m, 1H), 1.88-1.83 (m, 1H), 1.76-1.70 (m, 1H), 1.59-1.45 (m, 3H), 1.40-1.28 (m, 2H); MS: 465.7 [M + H]⁺.

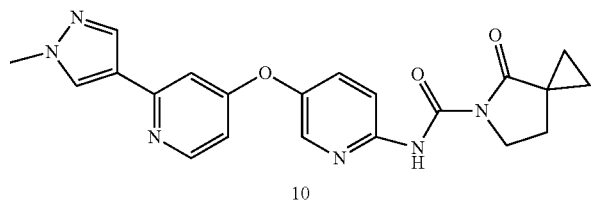 [SMILES: Cn1cc(-c2cc(Oc3ccc(NC(=O)N4CCC5(CC5)C4=O)nc3)ccn2)cn1]

10

¹H NMR (DMSO-d₆, 500 MHz) δ 11.08 (s, 1H), 8.39 (d, J = 5.6 Hz, 1H), 8.30-8.28 (m, 2H), 8.12 (d, J = 8.8 Hz, 1H), 7.98 (s, 1H), 7.80-7.76 (m, 1H), 7.26 (s, 1H), 6.75-6.70 (m, 1H), 3.93-3.95-3.90 (m, 2H), 3.86 (s, 3H), 2.20-2.15 (m, 2H), 1.17-1.12 m, 2H), 1.10-1.05 (m, 2H); MS: 405.5 [M + H]⁺.

| | | |
|---|---|---|
| 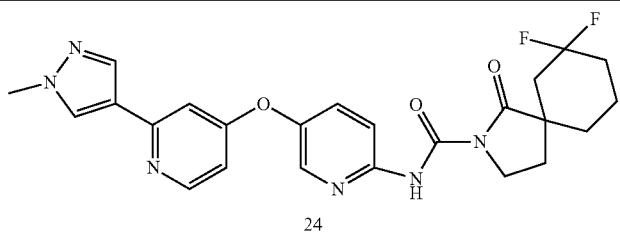<br>24 | | ¹H NMR (500 MHz, DMSO-d₆) δ 11.02 (s, 1H), 8.40 (d, J = 5.7 Hz, 1H), 8.30 (d, J = 2.5 Hz, 1H), 8.28 (s, 1H), 8.11 (d, J = 9.0 Hz, 1H), 7.98 (s, 1H), 7.79 (dd, J = 9.0, 2.8 Hz, 1H), 7.26 (d, J = 2.2 Hz, 1H), 6.72 (dd, J = 5.7, 2.4 Hz, 1H), 3.87 (s, 3H), 3.8-3.84 (m, 1H), 3.75-3.70 (m, 1H), 2.15-2.04 (m, 5H), 1.91-1.77 (m, 3H), 1.68-1.63 (m, 1H), 1.48-1.43 (m, 1H); MS: 483.5 [M + H]⁺. |
| 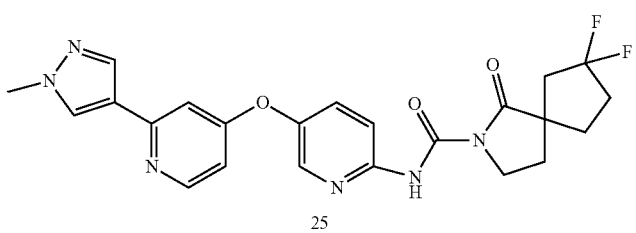 [SMILES: Cn1cc(-c2cc(Oc3ccc(NC(=O)N4CCC5(CCC(F)(F)C5)C4=O)nc3)ccn2)cn1]<br>25 | | ¹H NMR (500 MHz, DMSO-d₆) δ 10.99 (s, 1H), 8.40 (d, J = 5.7 Hz, 1H), 8.31 (d, J = 2.8 Hz, 1H), 8.28 (s, 1H), 8.11 (d, J = 9.0 Hz, 1H), 7.98 (s, 1H), 7.79 (dd, J = 9.0, 2.8 Hz, 1H), 7.26 (d, J = 2.3 Hz, 1H), 6.72 (dd, J = 5.7, 2.4 Hz, 1H), 3.87 (s, 3H), 3.85-3.81 (m, 1H), 3.80-3.74 (m, 1H), 2.54-2.53 (m, 1H), 2.32-2.26 (m, 3H), 2.15-2.08 (m, 3H), 2.00-1.94 (m, 1H); MS: 469.6 [M + H]⁺. |
| 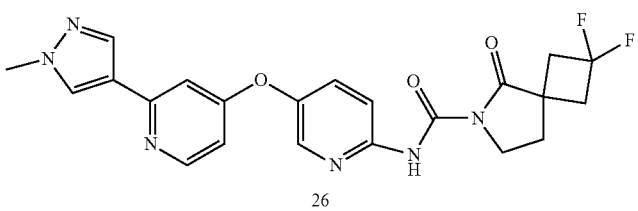 [SMILES: Cn1cc(-c2cc(Oc3ccc(NC(=O)N4CCC5(CC(F)(F)C5)C4=O)nc3)ccn2)cn1]<br>26 | | ¹H NMR (500 MHz, DMSO-d₆) δ 10.98 (s, 1H), 8.40 (d, J = 5.7 Hz, 1H), 8.31 (d, J = 2.7 Hz, 1H), 8.28 (s, 1H), 8.11 (d, J = 9.0 Hz, 1H), 7.99 (s, 1H), 7.79 (dd, J = 9.0, 2.8 Hz, 1H), 7.27 (d, J = 2.2 Hz, 1H), 6.73 (dd, J = 5.7, 2.4 Hz, 1H), 3.87 (s, 3H), 3.79 (t, J = 6.9 Hz, 2H), 3.03-2.94 (m, 2H), 2.77-2.70 (m, 2H), 2.29 (t, J = 6.8 Hz, 2H) MS: 455.6 [M + H]⁺. |

Preparation of Compound 11

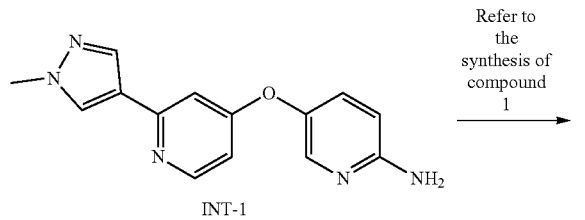

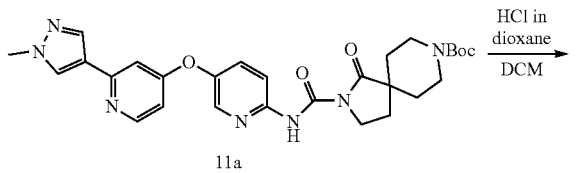

Compound 11a as white solid was prepared from starting material INT-1 using the similar procedures as described for synthesis of compound 1. ¹HNMR (DMSO-d₆, 500 MHz) δ 11.04 (s, 1H), 8.37 (d, J=5.7 Hz, 1H), 8.27 (d, J=3.0 Hz, 1H), 8.25 (s, 1H), 8.08 (d, J=9.0 Hz, 1H), 7.96 (s, 1H), 7.76 (dd, J=9.0, 3.0 Hz, 1H), 7.23 (d, J=3.0 Hz, 1H), 6.69 (dd, J=5.7, 3.0 Hz, 1H), 3.84 (s, 3H), 3.79 (t, J=7.1 Hz, 4H), 3.07-2.92 (m, 2H), 2.03 (t, J=7.1 Hz, 2H), 1.65-1.53 (m, 4H), 1.40 (s, 9H); MS: 548.3 [M+H]⁺.

To a solution of 11a (350 mg, 0.64 mmol) in DCM (6 mL) was added HCl (4 M in dioxane, 0.8 mL). The reaction was stirred at room temperature for 4 hours. LC/MS showed the starting material was consumed. The reaction was concentrated to give 11 as white solid. ¹H NMR (500 MHz, DMSO-d₆) δ 11.05 (s, 11H), 8.78 (s, 1H), 8.56 (d, J=6.0 Hz, 1H), 8.46 (s, 1H), 8.41 (s, 1H), 8.14 (d, J=9.0 Hz, 1H), 7.91 (d, J=9.0 Hz, 1H), 7.75 (s, 1H), 7.21-7.16 (m, 1H), 3.92 (s, 3H), 3.80 (t, J=7.0 Hz, 2H), 3.29-3.24 (m, 2H), 3.04-3.00 (m, 2H), 2.07 (t, J=7.0 Hz, 2H), 1.99-1.95 (m, 2H), 1.83-1.77 (m, 2H); MS: 448.5 [M+H]⁺.

Preparation of Compound 12

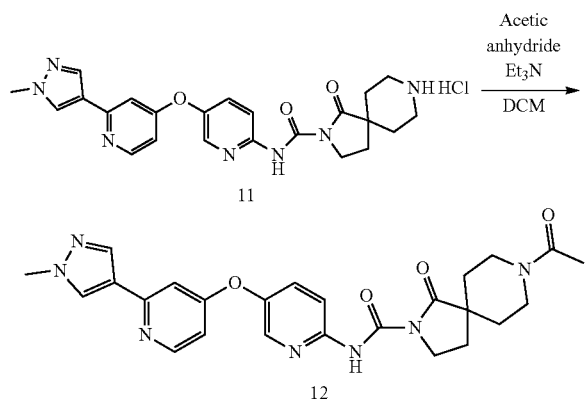

To a solution of compound 11 (120 mg, 0.25 mmol) and acetic anhydride (30.4 mg, 0.30 mmol) in DCM (5 ml) was added Et$_3$N (50 mg, 0.50 mmol). The reaction was stirred at room temperature for 4 hours. LC/MS showed the starting material was consumed. DCM (15 mL) and H$_2$O (20 ml) was then added and the organic layer was washed with brine (20 mL×2), dried over Na$_2$SO$_4$, filtered and concentrated under reduced pressure. The residue was purified by preparative TLC (DCM:MeOH=10:1) to give compound 12 (65 mg, 53% yield) as a white solid. $^1$H NMR (500 MHz, DMSO-d$_6$) δ 11.04 (s, 1H), 8.37 (d, J=6.0 Hz, 1H), 8.27 (br s, 1H), 8.26 (s, 1H), 8.07 (d, J=9.0 Hz, 1H), 7.95 (s, 1H), 7.76 (d, J=9.0 Hz, 1H), 7.23 (s, 1H), 6.69 (d, J=6.0 Hz, 1H), 4.16-4.11 (m, 1H), 3.83 (s, 3H), 3.82-3.71 (m, 3H), 3.24-3.16 (m, 1H), 2.90-2.82 (m, 1H), 2.05 (t, J=7.0 Hz, 2H), 2.00 (s, 3H), 1.72-1.68 (m, 1H), 1.65-1.54 (m, 3H); MS: 490.4 [M+H]$^+$.

Preparation of Compound 13

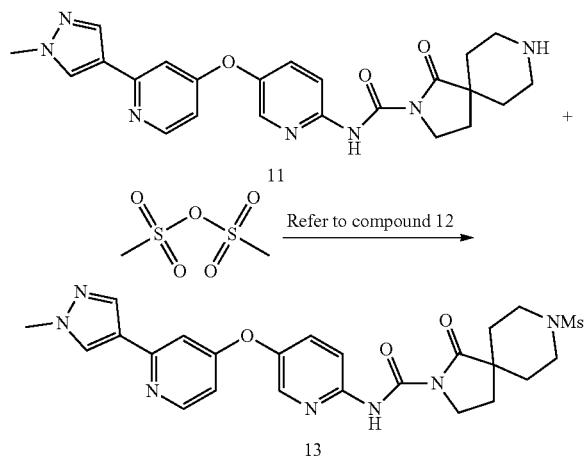

Compound 13 as a white solid was prepared from starting material 11 and methanesulfonic anhydride using the similar procedures as described for synthesis of compound 12. $^1$H NMR (500 MHz, DMSO-d$_6$) δ 11.04 (s, 1H), 8.37 (d, J=5.5 Hz, 1H), 8.27 (d, J=3.0 Hz, 1H), 8.26 (s, 1H), 8.08 (d, J=9.0 Hz, 1H), 7.96 (s, 1H), 7.76 (dd, J=9.0, 3.0 Hz, 1H), 7.23 (d, J=2.0 Hz, 1H), 6.69 (dd, J=5.5, 2.0 Hz, 1H), 3.84 (s, 3H), 3.80 (t, J=7.1 Hz, 2H), 3.49-3.47 (m, 2H), 2.95-2.91 (m, 2H), 2.89 (s, 3H), 2.02 (t, J=7.1 Hz, 2H), 1.83-1.71 (m, 4H); MS: 526.3 [M+H]$^+$.

Preparation of Compound 14

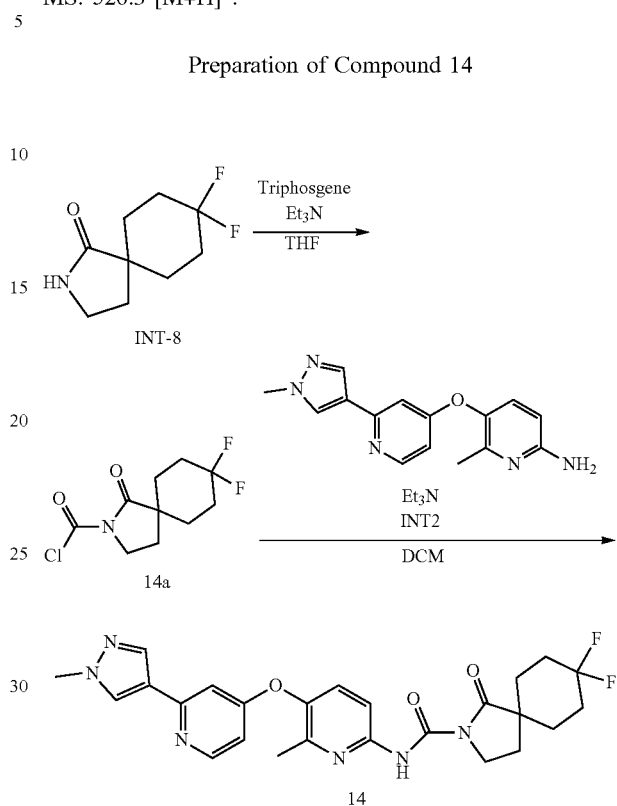

To a solution of compound INT-8 (20 mg, 0.15 mmol) and Et$_3$N (21.4 mg, 0.21 mmol) in THF (2 ml) was added triphosgene (23.5 mg, 0.79 mmol) in THF (1 ml) dropwise under 0° C. The reaction was stirred at room temperature for 1 hour and refluxed for 1 hour. The reaction was 5 cooled to room temperature. EtOAc (15 mL) and H$_2$O (15 ml) was then added and the organic layer was washed with brine (20 mL×2), dried over Na$_2$SO$_4$, filtered and concentrated under reduced pressure to give crude product compound 14a, which was used for the next step directly.

To a solution of compound INT-2 (30 mg, 0.106 mmol) and Et$_3$N (21.4 mg, 0.211 mmol) in DCM (3 mL) was added compound 14a in DCM (1 mL). The reaction was stirred at room temperature for 16 hours. DCM (15 mL) and H$_2$O (20 mL) was then added and the organic layer was washed with brine (20 mL×2), dried over Na$_2$SO$_4$, filtered and concentrated under reduced pressure. The residue was purified by preparative TLC (DCM:MeOH=20:1) to give compound 14 (19 mg, 36% yield) as a white solid. $^1$H NMR (500 MHz, DMSO-d$_6$) δ 10.98 (s, 1H), 8.40 (d, J=6.0 Hz, 1H), 8.31 (s, 1H), 8.01 (s, 1H), 7.93 (d, J=8.8 Hz, 1H), 7.68 (d, J=8.8 Hz, 1H), 7.25 (brs, 1H), 6.68 (br s, 1H), 3.87 (s, 3H), 3.80 (t, J=7.0 Hz, 2H), 2.28 (s, 3H), 2.17-2.07 (m, 2H), 2.05 (t, J=7.0 Hz, 2H), 2.00-1.90 (m, 2H), 1.85-1.75 (m, 4H); MS: 497.5 [M+H]$^+$.

Compound 15, 16 was prepared using the similar procedures as described for synthesis of compound 14. The corresponding spectral information was shown in the following table:

| | |
|---|---|
| 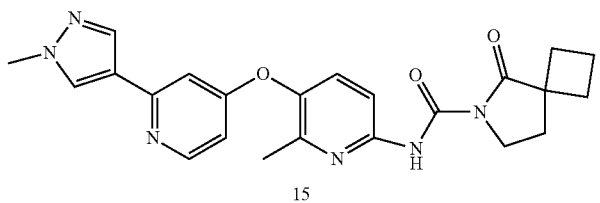 [SMILES: Cc1nc(NC(=O)N2CCC3(CCC3)C2=O)ccc1Oc1ccnc(-c2cnn(C)c2)c1] 15 | ¹H NMR (DMSO-d₆, 500 MHz) δ 11.04 (s, 1H), 8.37 (d, J = 5.5 Hz, 1H), 8.27 (s, 1H), 7.97 (s, 1H), 7.92 (d, J = 9.0 Hz, 1H), 7.66 (d, J = 9.0 Hz, 1H), 7.18 (s, 1H), 6.64-6.60 (m, 1H), 3.86 (s, 3H), 3.71 (t, J = 6.5 Hz, 2H), 2.39-2.32 (m, 2H), 2.28 (s, 3H), 2.18 (t, J = 6.5 Hz, 2H), 2.05-1.90 (m, 4H); MS: 433.5 [M + H]⁺. |
| 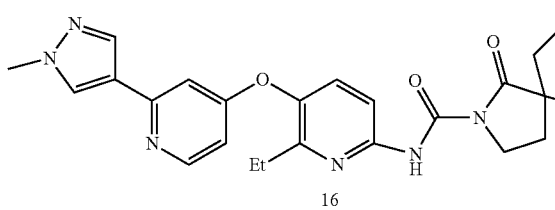 16 | ¹H NMR (DMSO-d₆, 500 MHz) δ 10.99 (s, 1H), 8.37 (d, J = 5.7 Hz, 1H), 8.26 (s, 1H), 7.97 (s, 1H), 7.93 (d, J = 8.8 Hz, 1H), 7.66 (d, J = 8.8 Hz, 1H), 7.20 (d, J = 2.4 Hz, 1H), 6.60 (dd, J = 5.7, 2.4 Hz, 1H), 3.85 (s, 3H), 3.80 (t, J = 7.1 Hz, 2H), 2.60 (q, J = 7.6 Hz, 2H), 2.12 (dd, J = 22.0, 13.0 Hz, 2H), 2.05 (t, J = 7.1 Hz, 2H), 1.94 (dd, J = 28.6, 13.5 Hz, 2H), 1.80 (tdd, J = 17.2, 13.1, 3.8 Hz, 4H), 1.13 (t, J = 7.5 Hz, 3H); MS: 511.3 [M + H]⁺. |

Preparation of Compound 17

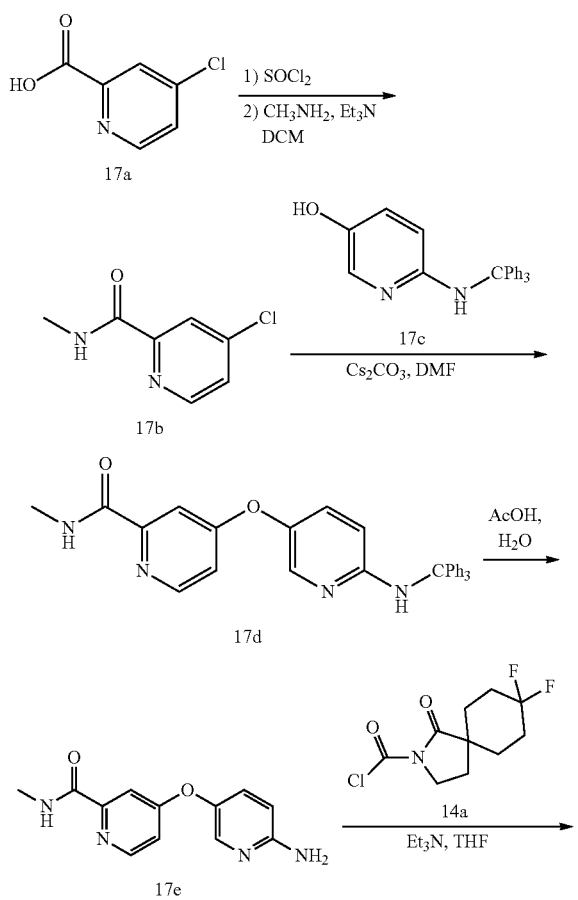

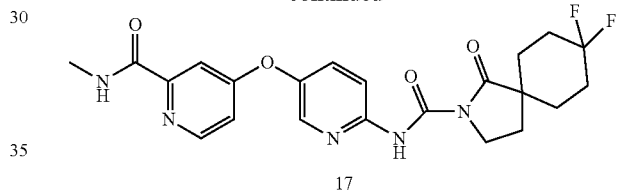

17

A solution of compound 17a (500 mg, 3.2 mmol) in SOCl₂ (1 mL) was stirred at 80° C. for 3 hours. The reaction was concentrated. And the residue was re-dissolved in DCM (8 mL), which was further added methylamine (118 mg, 3.8 mmol) and Et₃N (0.88 mL, 6.4 mmol). The reaction was stirred at room temperature for 2 hours. The volatiles were removed and the residue was purified by chromatography on silica gel (petroleum ether:EtOAc=0:100 to 50:100) to give compound 17b (250 mg, 46% yield) as yellow oil.

To a solution of compound 17b (218 mg, 1.28 mmol) and 17c (450 mg, 1.28 mmol) in DMF (15 mL) was added Cs₂CO₃ (832 mg, 2.55 mmol). The reaction mixture was stirred at 90° C. for 16 h. After cooling to room temperature. EtOAc (100 mL) and H₂O (100 ml) was added and the organic layer was washed with brine (100 mL), dried over Na₂SO₄, filtered and concentrated under reduced pressure. The residue was purified by chromatography on silica gel (petroleum ether:EtOAc=0:100 to 50:100) to give compound 17d (420 mg, 68% yield) as a white solid.

A solution of compound 17d (400 mg, 0.82 mmol) in AcOH (2 mL) and H₂O (0.6 mL). The reaction was stirred at 75° C. for 2 hours. Then the reaction was cooled to room temperature. After filtration, EtOAc (40 mL) was added to the filtrate, which was adjusted to pH=8 using 20% w/w NaOH solution. The resulting organic layer was then washed with brine (100 mL), dried over Na₂SO₄, filtered and concentrated under reduced pressure to give compound 17e (150 mg, 75% yield) as white solid. MS: 245.4 [M+H]⁺.

Compound 17 was prepared from starting material compounds 17e and 14a using the similar procedures as described for synthesis of compound 14. 1H NMR (500 MHz, DMSO-d6) δ 11.06 (s, 1H), 8.79 (d, J=4.8 Hz, 1H), 8.54 (d, J=5.6 Hz, 1H), 8.33 (d, J=2.9 Hz, 1H), 8.12 (d, J=9.0 Hz, 1H), 7.83 (dd, J=9.0, 2.9 Hz, 1H), 7.42 (d, J=2.6 Hz, 1H), 7.20 (dd, J=5.6, 2.6 Hz, 1H), 3.80 (t, J=7.1 Hz, 2H), 2.79 (d, J=4.8 Hz, 3H), 2.15-2.07 (m, 2H), 2.05 (t, J=7.1 Hz, 2H), 2.00-1.88 (m, 2H), 1.85-1.75 (m, 4H); MS: 460.2 [M+H]$^+$.

Preparation of Compound 18

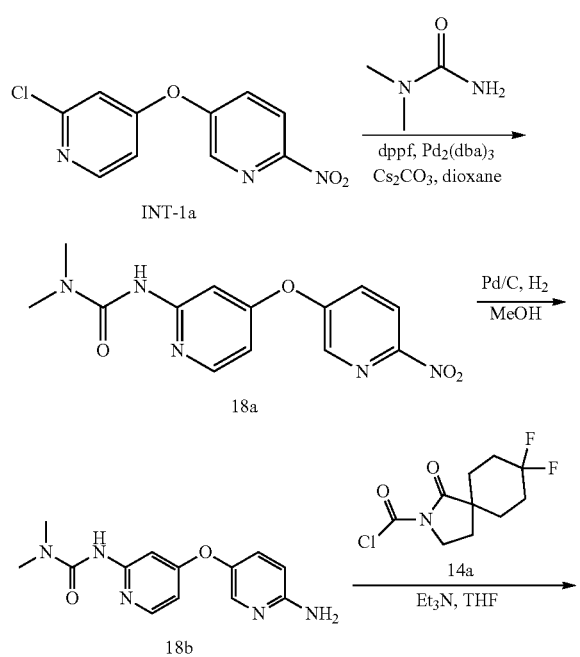

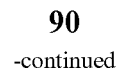

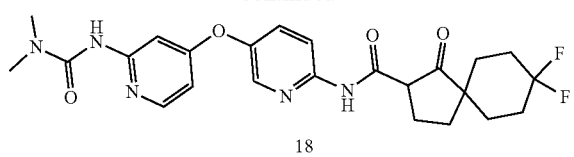

To a solution of compound INT-1a (150 mg, 0.60 mmol) and 1,1-dimethylurea (105 mg, 1.20 mmol) in dioxane (5 mL) was added dppf (33 mg, 0.06 mmol), Pd$_2$(dba)$_3$ (27 mg, 0.03 mmol) and Cs$_2$CO$_3$ (388 mg, 1.20 mmol). The reaction was stirred at 95° C. for 16 hours under N$_2$. The reaction was cooled to room temperature and concentrated under reduced pressure. The residue was purified by chromatography on silica gel (petroleum ether:EtOAc=0:100 to 80:100) to give compound 18a (110 mg, 61% yield) as a yellow solid. MS: 304.4 [M+H]$^+$.

To a solution of compound 18a (88 mg, 0.29 mmol) in MeOH (10 mL) was added Pd/C (10 mg, 10% w/w). The reaction was stirred at room temperature for 16 hours under H$_2$ (1 atm). After filtration, the filtrate was concentrated under reduced pressure to give compound 18b (78 mg, 98% yield) as a yellow solid. MS: 274.0 [M+H]$^+$.

Compound 18 was prepared from starting material compounds 18b and 14a using the similar procedures as described for synthesis of compound 14. 1H NMR (500 MHz, DMSO-d6) δ 11.05 (s, 1H), 8.93 (s, 1H), 8.27 (d, J=2.5 Hz, 1H), 8.14 (d, J=5.7 Hz, 1H), 8.10 (d, J=9.0 Hz, 1H), 7.76 (dd, J=9.0, 2.8 Hz, 1H), 7.41 (d, J=2.0 Hz, 1H), 6.63 (dd, J=5.7, 2.3 Hz, 1H), 3.81 (t, J=7.1 Hz, 2H), 2.90 (s, 6H), 2.16-2.09 (m, 2H), 2.05 (t, J=7.1 Hz, 2H), 1.98-1.90 (m, 2H), 1.86-1.76 (m, 4H); MS: 489.5 [M+H]$^+$.

Compound 19 was prepared using the similar procedures as described for synthesis of compound 18. The corresponding spectral information was shown in the following table:

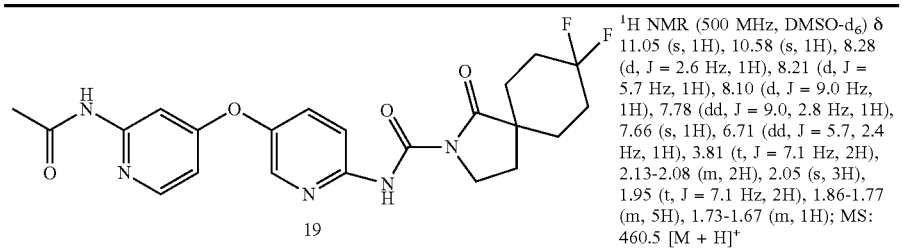

| Structure | Spectral Data |
|---|---|
| 19 | $^1$H NMR (500 MHz, DMSO-d$_6$) δ 11.05 (s, 1H), 10.58 (s, 1H), 8.28 (d, J = 2.6 Hz, 1H), 8.21 (d, J = 5.7 Hz, 1H), 8.10 (d, J = 9.0 Hz, 1H), 7.78 (dd, J = 9.0, 2.8 Hz, 1H), 7.66 (s, 1H), 6.71 (dd, J = 5.7, 2.4 Hz, 1H), 3.81 (t, J = 7.1 Hz, 2H), 2.13-2.08 (m, 2H), 2.05 (s, 3H), 1.95 (t, J = 7.1 Hz, 2H), 1.86-1.77 (m, 5H), 1.73-1.67 (m, 1H); MS: 460.5 [M + H]$^+$ |

Preparation of Compound 20

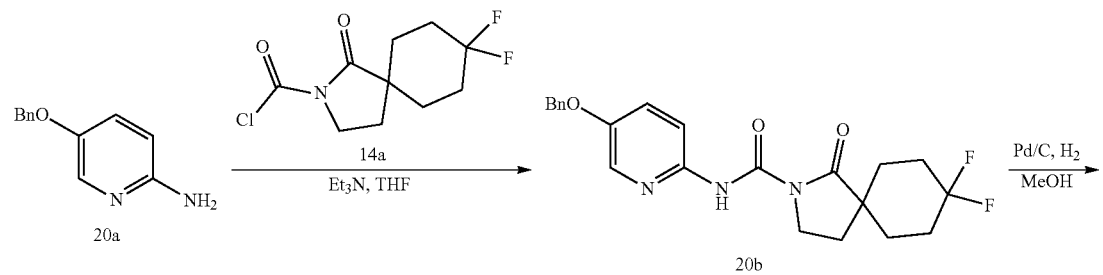

-continued

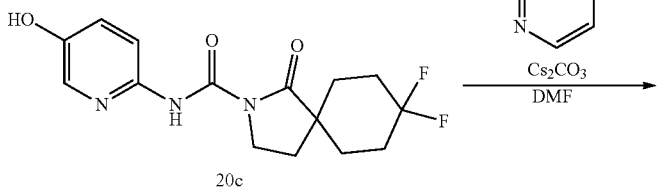

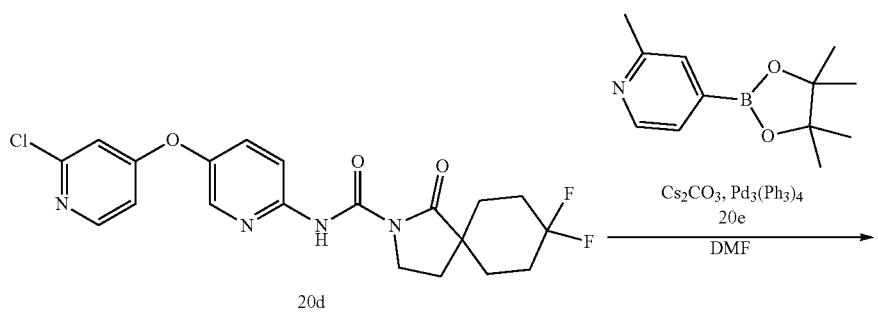

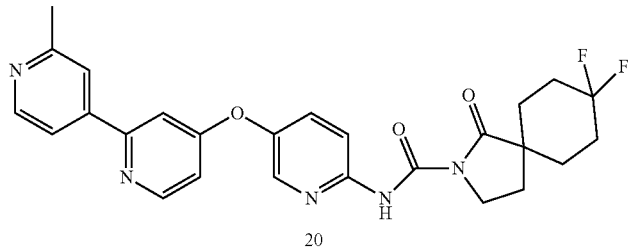

Compound 20b was prepared from starting material compounds 20a and 14a using the similar procedures as described for synthesis of compound 14.

To a solution of compound 20b (2.86 g, 6.9 mmol) in MeOH (150 mL) was added Pd/C (300 mg, 10% w/w). The reaction was stirred at room temperature for 16 hours under $H_2$ (1 atm). After filtration, the filtrate was concentrated under reduced pressure to give compound 20c (2.20 g, 98% yield) as a yellow solid. MS: 326.4 [M+H]$^+$.

To a solution of compound 20c (2.2 g, 6.1 mmol) and 2-chloro-4-fluoropyridine (841 mg, 6.4 mmol) in DMF (15 ml) was added $Cs_2CO_3$ (2.58 g, 7.9 mmol). The reaction was stirred at room temperature for 2 hours. EtOAc (150 mL) and $H_2O$ (150 ml) was then added and the organic layer was washed with brine, dried over $Na_2SO_4$, filtered and concentrated under reduced pressure. The residue was purified by chromatography on silica gel (petroleum ether:EtOAc=1:1) to give compound 20d (2.1 g, 80% yield) as a yellow solid. MS: 436.1 [M+H]$^+$.

Compound 20 as yellow solid was prepared from starting material compounds 20d and 20e using the similar procedures as described for synthesis of compound INT-1. $^1$H NMR (500 MHz, CDCl3) δ 11.10 (s, 1H), 8.60 (d, J=5.5 Hz, 2H), 8.21 (d, J=2.0 Hz, 1H), 8.18 (d, J=8.5 Hz, 1H), 7.73 (s, 1H), 7.60 (s, 1H), 7.50 (dd, J=8.9, 2.6 Hz, L H), 7.31 (d, J=1.9 Hz, 1H), 6.86 (dd, J=5.4, 2.1 Hz, 1H), 3.90 (t, J=7.1 Hz, 2H), 2.65 (s, 3H), 2.38-2.27 (s, 2H), 2.05-2.00 (m, 4H), 1.94-1.84 (m, 2H), 1.76-1.71 (m, 2H); MS: 494.3 [M+H]$^+$.

Compound 21, 22, 23 was prepared using the similar procedures as described for synthesis of compound 20. The specific spectral information was shown in the following table:

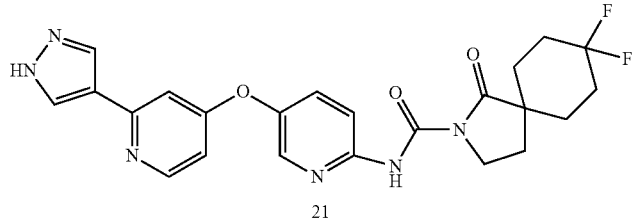 [SMILES: O=C(Nc1ccc(Oc2ccnc(-c3cn[nH]c3)c2)cn1)N1CCC2(CCC(F)(F)CC2)C1=O]

21

$^1$HNMR (500 MHz, CDCl$_3$) δ 11.09 (s, 1H), 8.46 (d, J = 5.4 Hz, 1H), 8.25-8.05 (m, 4H), 7.49 (dd, J = 8.9, 2.4 Hz, 1H), 7.05 (s, 1H), 6.70 (d, J = 5.1 Hz, 1H), 3.90 (t, J = 7.0 Hz, 2H), 2.38-2.24 (m, 2H), 2.11-1.98 (m, 4H), 1.96-1.83 (m, 2H), 1.77-1.70 (m, 2H); MS: 469.7 [M + H]$^+$

-continued

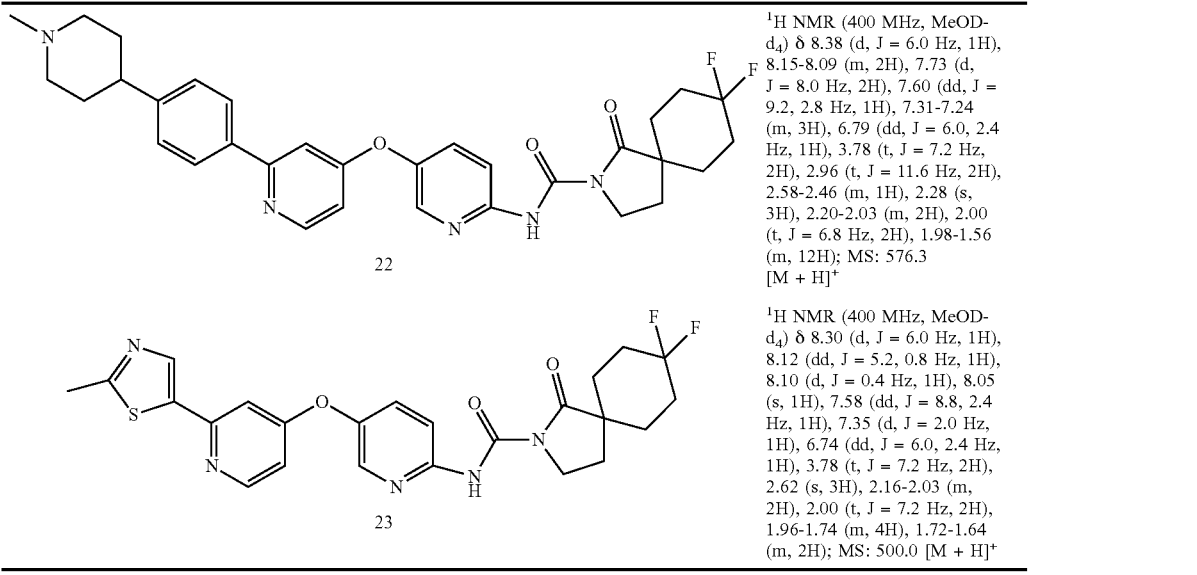

| | ¹H NMR (400 MHz, MeOD-d₄) δ 8.38 (d, J = 6.0 Hz, 1H), 8.15-8.09 (m, 2H), 7.73 (d, J = 8.0 Hz, 2H), 7.60 (dd, J = 9.2, 2.8 Hz, 1H), 7.31-7.24 (m, 3H), 6.79 (dd, J = 6.0, 2.4 Hz, 1H), 3.78 (t, J = 7.2 Hz, 2H), 2.96 (t, J = 11.6 Hz, 2H), 2.58-2.46 (m, 1H), 2.28 (s, 3H), 2.20-2.03 (m, 2H), 2.00 (t, J = 6.8 Hz, 2H), 1.98-1.56 (m, 12H); MS: 576.3 [M + H]⁺ |
|---|---|
| 22 | |
| 23 | ¹H NMR (400 MHz, MeOD-d₄) δ 8.30 (d, J = 6.0 Hz, 1H), 8.12 (dd, J = 5.2, 0.8 Hz, 1H), 8.10 (d, J = 0.4 Hz, 1H), 8.05 (s, 1H), 7.58 (dd, J = 8.8, 2.4 Hz, 1H), 7.35 (d, J = 2.0 Hz, 1H), 6.74 (dd, J = 6.0, 2.4 Hz, 1H), 3.78 (t, J = 7.2 Hz, 2H), 2.62 (s, 3H), 2.16-2.03 (m, 2H), 2.00 (t, J = 7.2 Hz, 2H), 1.96-1.74 (m, 4H), 1.72-1.64 (m, 2H); MS: 500.0 [M + H]⁺ |

Biological Test Example

Example 1: Kinase Activity Test

The specific operation is as follows: Set the concentration gradient of the test compound and dilute the test compound to the working concentration with DMSO. In a 384-well plate, add 10 nL of the test compound to each well with the Echo 550 sample loading device. The dilution buffer of CSF1R is IX Enzymatic buffer containing 5 mM MgCl2, 1 mM MnCl2, 1 mM DTT, 12.5 nM SEB. Use this buffer to adjust the concentration of CSF1R to 0.02 ng/ul. Add 5 μL of buffer containing CSF1R to the 384-well plate after centrifugation at 1000 g for 30 seconds and incubate at room temperature for 10 minutes. Add 5 μL of buffer containing TK-substrate-biotin (2 μM) and ATP (8 μM) (the formula is the same as above) After centrifugation at 1000 g for 30 seconds, incubate at room temperature for 40 minutes, then add 10 μL of stop solution (containing 5 μL of 250 nM Sa-XL665 and 5 μL of TK-antibody-Cryptate), incubate for 60 minutes and use Envision 2104 plate reader to detect at 620 Fluorescence signal of nm (Cryptaet) and 665 nm (XL665), get the ratio (665/620 nm). The inhibition rate of each point is obtained by the following formula:

% Inhibition is calculated as follow:

$$\% \text{ Inhibition} = \left[1 - \frac{\text{Ratio}_{cmpd} - \overline{\text{Ratio}}_{positive}}{\overline{\text{Ratio}}_{vehicle} - \overline{\text{Ratio}}_{positive}}\right] * 100$$

Wherein, $\overline{\text{Ratio}}_{positive}$: the experimental positive control None; $\overline{\text{Ratio}}_{vehicle}$: is the test value of 0.1% DMSO. With the compound concentration and inhibition rate on the abscissa and ordinate, the curve was drawn, and the curve was fitted with Graphpad 5.0 software and the IC50 was calculated.

c-Kit, PDGFRα, PDGFRβ, FLT-3 Kinase Activity Test

Caliper mobility shift assay was used to determine the kinase activities of c-Kit, PDGFRα, PDGFRβ, and FLT-3. Among them, c-Kit comes from Eurofins (cat #: 14-559M); PDGFRα comes from BPS (cat #: 40260); PDGFRβ comes from Invitrogen (cat #: PR4465B); FLT-3 comes from Carna (cat #: 08-154); Peptide substrate P2 is provided by GL Biochem (cat #: 112394) as a substrate of FLT-3 kinase; Peptide substrate P22 is provided by GL Biochem (cat #: 112393) as c-Kit, PDGFRα, PDGFRβ kinase substrate.

The final concentration of the kinase and its corresponding substrate (ATP and peptide substrate P2 or P22) during the experiment is as follows:

| c-Kit: 10 nM | PDGFRα: 3.5 nM | PDGFRβ: 5.0 nM | FLT-3: 0.9 nM |
|---|---|---|---|
| substrate: 6 μM | substrate: 134 μM | substrate: 54 μM | substrate: 97 μM |

Add 5 μL of compound (10% DMSO) at 5 times the final concentration of the reaction to a 384-well plate. Add 10 μL of 2.5×enzyme solution and incubate for 10 minutes at room temperature, then add 10 μL of 2.5×substrate (ATP and peptide substrate, P2 or P22). After incubating at 28° C. for 60 minutes, add 25 μL stop solution to stop the reaction. Read conversion rate data on Caliper EZ Reader II (Caliper Life Sciences). Convert the conversion rate into inhibition rate data (% inhibition rate=(max−sample conversion rate)/(max−min)×100). Where max refers to the conversion rate of the DMSO control, and min refers to the conversion rate of the control without enzyme activity. Draw a curve with compound concentration and inhibition rate on the abscissa and ordinate, use XLFit excel add-in version 4.3.1 software to fit the curve and calculate IC50.

The results of the activity of the compounds listed in the examples on CSF1R, c-Kit, PDGFRα, PDGFRβ and FLT-3:

| Compound NO. | CSF1R IC₅₀ (nM) | c-Kit IC₅₀ (nM) | PDGFRα IC₅₀ (nM) | PDGFRβ IC₅₀ (nM) | FLT-3 IC₅₀ (nM) |
|---|---|---|---|---|---|
| 1 | 0.66 | 3.5 | 101 | 2855 | >10000 |
| 2 | 6.2 | 5.4 | | 1575 | |
| 3 | 1.1 | 2.6 | | 1625 | |
| 4 | 8.5 | 16 | 40 | 783 | >10000 |
| 5 | 9.1 | | | | |
| 6 | 5.4 | | | | |
| 7 | 2.7 | | | | |

-continued

| Compound NO. | CSF1R IC$_{50}$ (nM) | c-Kit IC$_{50}$ (nM) | PDGFRα IC$_{50}$ (nM) | PDGFRβ IC$_{50}$ (nM) | FLT-3 IC$_{50}$ (nM) |
|---|---|---|---|---|---|
| 8 | 2.3 | | | | |
| 9 | 2.1 | | | | |
| 10 | 0.55 | | | | |
| 11 | 300 | | | | |
| 12 | 171 | | | | |
| 13 | 25 | | | | |
| 14 | 6.2 | 17 | 198 | >10000 | >10000 |
| 15 | 1.2 | 29 | 512 | >10000 | >10000 |
| 16 | 6.4 | | | | |
| 17 | 6.5 | | | | |
| 18 | 4.7 | 8.4 | 65 | 343 | 8632 |
| 19 | 5.4 | 11 | 121 | 719 | >10000 |
| 20 | 5.9 | 24.7 | 64.6 | 8437 | |
| 21 | 2.8 | 10.1 | 43 | 7447 | |
| 22 | 6.7 | | | | |
| 23 | 5.3 | | | | |
| 24 | 4.8 | 20 | 93 | | |
| 25 | 2.0 | 5.0 | 62 | | |
| 26 | 1.4 | 4.5 | 42 | 2808 | >10000 |

Example 2

Inhibition test of compound on FMS phosphorylation (ELISA test) Set the concentration gradient of the test compound with DMSO solution, and dilute the test compound at 1:500 with RPMI1640 (cat #: 01-100-1ACS, BI) containing 10% inactivated serum (cat #: 1707125, BI). Harvest THP-1 cells and adjust the cell density to 2×10$^6$ cells/ml. Take 500 µL of the cell suspension and the above-diluted compound and mix it 1:1 and spread it into a 24-well plate (cat #: 3524, costar). Place the culture plate in a cell incubator and incubate for 4 hours. The incubation conditions are 37° C., 5% CO2, and humidity 95%. After the incubation, the recombinant human MCSF (cat #: 216-MC, R&D Systems) was diluted with RPMI1640 containing 10% inactivated serum to make the final concentration 100 ng/ml. Add the diluted recombinant human MCSF to a 24-well plate at 100 µL per well, mix quickly and incubate in an incubator for 4 minutes. The incubation conditions are: temperature 37° C., 5% C02, and humidity 95%. After incubation, perform protein extraction and ELISA experiments according to the method suggested in the phosphorylated CSF1R detection kit (cat #: DYC3268, R&D Systems). After reading the data with the microplate reader, calculate the inhibition rate of the test compound, use GraphPad Prism to plot and calculate the EC50 of the test compound.

| Compound NO. | FMS EC$_{50}$ (nM) |
|---|---|
| BLZ-945 | 182 |
| 1 | 3.5 |
| 4 | 15.5 |
| 10 | 4.0 |
| 14 | 118 |
| 26 | 9.0 |

Example 3: Anti-Tumor Effect of the Compound in Mouse Colon Cancer MC38 Cell Line Allotransplanted in C57BL/6 Mouse Animal Model Experimental animals: C57BL/6 mice, female, 6-8 weeks (weeks of age at the time of tumor cell inoculation), weighing 18-22 g. Purchased from Shanghai Lingchang Biological Technology Co., Ltd., animal certificate number: 2013001832351. Feeding environment: SPF level.

Weigh a certain amount of the drug, add 0.5% methylcellulose aqueous solution to prepare 0.24, 0.8, and 2.4 mg/mL colorless, clear and transparent liquid or uniformly dispersed suspension. The corresponding doses were 2.4, 8.0 and 24 mg/kg, and the dose volume was 10 mL/kg.

MC38 cells were cultured in DMEM medium containing 10% fetal bovine serum. Collect MC38 cells in the exponential growth phase and resuspend in PBS to a suitable concentration for subcutaneous tumor inoculation in $C_{57}BL/6$ mice.

The experimental mice were subcutaneously inoculated with 1×10$^6$ MC38 cells on the right back, and the cells were resuspended in PBS (0.1 ml/mouse). The tumor growth was observed regularly. When the tumor grew to an average volume of 101 mm3, the mice were randomly grouped according to tumor size and weight Administration. Dosing frequency is twice a day; tumor size is tested every other day.

T/C % is the relative tumor growth rate, that is, the percentage value of the relative tumor volume between the treatment group and the control group at a certain point in time. T and C are the relative tumor volume (RTV) of the treatment group and the control group at a specific time point, respectively.

All experimental results are expressed as the average tumor volume±SEM (mean standard error). Statistical analysis between different groups selects the best drug treatment point (usually after the last dose). The independent sample T test method was used to compare whether the relative tumor volume and tumor weight of the treatment group were significantly different from the control group. All data were analyzed with SPSS 18.0. p<0.05 is a significant difference.

Figure 2:
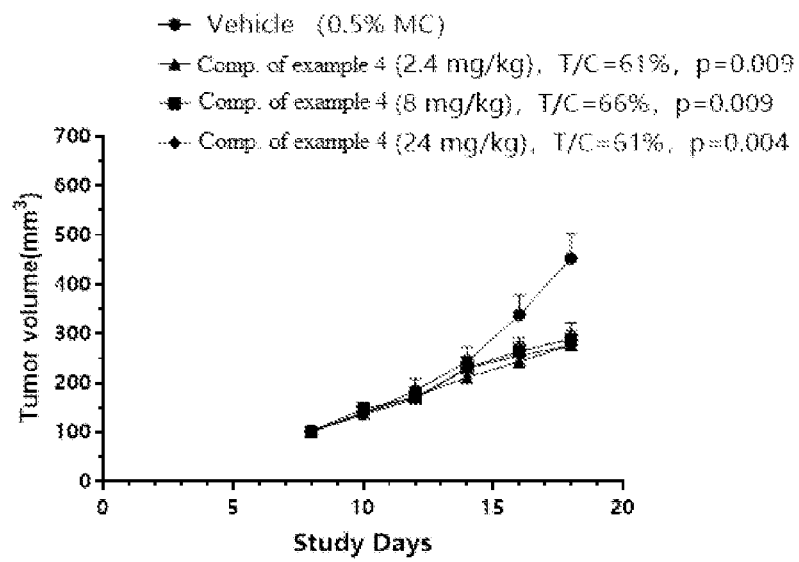
FIG. 2 shows the efficacy results of the compound of Example 4.

The efficacy results of the test compound are shown in FIGS. 1-2.

Pharmacokinetic Evaluation

Using mice as the test animals, the LC/MS/MS method was used to determine that the mice were intragastrically administered the compound of Example 1, the compound of Example 2, the compound of Example 3, the compound of Example 4, the compound of Example 10, and the compound of Example 14. Compound, the concentration of the drug in the plasma at different times after the compound of Example 26. Study the pharmacokinetic behavior of the compound of the present invention in mice and evaluate its pharmacokinetic characteristics.

The test animals were CD-1 mice, purchased from Shanghai Slack Laboratory Animal Co., Ltd.

Weigh a certain amount of drug, add 5% volume of DMSO or DMAc, 5% volume of PEG400 and 90% volume of normal saline to prepare 1.0 mg/mL colorless, clear and transparent liquid or uniformly dispersed suspension.

CD-1 mice were fasted overnight and then administered by gavage. The dosage was 10 mg/kg and the dosage was 10 mL/kg.

Gavage the mice before and after administration at 0.25, 0.5, 1.0, 2.0, 4.0, 6.0, 8.0, 24.0 hours to collect 0.1 mL of blood, place it in a K2-EDTA anticoagulation tube, and centrifuge at 3500 rpm for 10 minutes. Plasma, stored at −20° C.

To determine the content of the test compound in mouse plasma after gavage of different concentrations of drugs: take 20 uL of mouse plasma at each moment after administration, add propranolol and tolbutamide (each 100 ng/mL) 200 uL of acetonitrile solution, vortex for 5 minutes, centrifuge for 12 minutes (4000 rpm), and take 5 uL of the supernatant from the plasma sample for LC/MS/MS analysis.

The pharmacokinetic parameters of the compound of the present invention are as follows:

| Comp. NO. | Cmax (ug/mL) | AUC (ug/mL/h) | T½ (h) | F % |
|---|---|---|---|---|
| 1 | 3.39 | 26.6 | 2.73 | 100% |
| 2 | 0.86 | 6.1 | 3.14 | 71.5% |
| 3 | 3.20 | 15.8 | 3.30 | 89.5% |
| 4 | 5.27 | 38.8 | 2.64 | 100% |
| 10 | 2.24 | 21.3 | 5.18 | 64.0% |
| 14 | 1.40 | 20.3 | 5.91 | 67.3% |
| 26 | 4.49 | 48.3 | 6.72 | 79.0% |

The above are only some preferred embodiments of the present invention. It should be pointed out that for those of ordinary skill in the art, without departing from the technical principles of the present invention, several improvements and modifications can be made. These improvements and Retouching should also be regarded as within the protection scope of the present invention.

The invention claimed is:

1. A compound of formula I or a pharmaceutically acceptable salt, solvate, hydrate, stereoisomer, a mixture of stereoisomers or a racemic mixture of stereoisomers thereof:

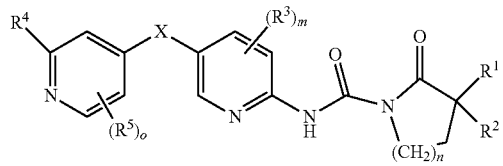

(1)

wherein, X represents $CR^aR^{a'}$,

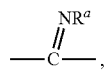

$NR^a$, —C(O)—, O, S, S(O), or $S(O)_2$;

$R_1$ and $R_2$, together with the carbon atom directly attached thereto form a saturated or unsaturated 3 to 12 membered cycloalkyl or cycloheteroalkyl ring, the heterocycloalkyl group contains at least one heteroatom selected from O, N and S, the cycloalkyl group or heterocycloalkyl group can be optionally substituted by 0, 1, 2, 3 or 4 substituents each independently selected from the following $R^6$: halogen, hydroxy, $C_1$-$C_8$ alkyl, $C_3$-$C_8$ cycloalkyl, $C_3$-$C_8$ heterocycloalkyl, $C_2$-$C_8$ alkenyl, $C_2$-$C_8$ alkynyl, $C_1$-$C_8$ haloalkyl, $C_1$-$C_8$ alkoxy, $C_1$-$C_8$ haloalkoxy, $C_3$-$C_8$ cycloalkoxy, $C_3$-$C_8$ heterocyclic alkoxy, —S—($C_1$-$C_8$) alkyl, —S—($C_3$-$C_8$) cycloalkyl, —S—($C_3$-$C_8$) heterocycloalkyl, cyano, nitro, —($C_0$-$C_8$) alkyl-$NR^9R^{a'}$, —C=$NR^a$, —O-Cy1, —O—($C_0$-$C_8$)alkyl-$Cy^1$, —($C_2$-$C_8$)alkenyl-$Cy^1$, —($C_2$-$C_8$)alkynyl-$Cy^1$, —C(O)$OR^a$, —C(O)$R^a$, —OC(O)$R^a$, —C(O)—$NR^aR^{a'}$, —$NR^a$—C(O)—$R^a$, —$NR^a$—C(O)—$OR^a$, —($C_1$-$C_8$) alkyl-$NR^a$—C(O)$R^a$, —$SO_2$—$NR^aR^{a'}$ and —$SO_2R^a$;

$R^3$ and $R^5$ each independently represent hydrogen, halogen, $C_1$-$C_8$ alkyl, $C_1$-$C_8$ alkoxy, $C_3$-$C_8$ cycloalkyl, $C_3$-$C_8$ heterocycloalkyl, halogenated $C_1$-$C_8$ alkyl, hydroxyl, amino, nitro, cyano, —C(O)$OR^a$, —OC(O)$R^a$, —C(O)—$NR^aR^{a'}$, —$NR^a$—C(O)—$R^a$, —$NR^a$—C(O)—$OR^a$, —($C_1$-$C_8$)alkyl-$NR^a$—C(O)$R^a$, —$SO_2$—$NR^aR^{a'}$ or —$SO_2R^a$;

$R^4$ represents $Cy^2$, —NHC(O)$R^a$, —NHC(O)$NR^aR^{a'}$, —C(O)$R^a$, —C(O)$NR^aR^{a'}$, —$S(O)_2R^a$, —$S(O)_2NR^aR^{a'}$, $NHS(O)_2R^a$ or —$NHS(O)_2NR^aR^{a'}$;

wherein, $Cy^1$ and $Cy^2$ each independently represent a 5-12 membered ring which was independently substituted by 0, 1, 2, 3 or 4 substituents, wherein the substituents are halogen, $C_1$-$C_8$ alkyl, $C_1$-$C_8$ alkoxy, $C_3$-$C_9$ cycloalkyl, $C_3$-$C_9$ heterocycle alkyl, halogenated $C_1$-$C_8$ alkyl, hydroxy, nitro, cyano, —C(O)$OR^a$, —OC(O)$R^a$, —C(O)—$NR^aR^{a'}$, —$NR^a$—C(O)— $R^a$, —$NR^a$—C(O)—$OR^a$, —($C_1$-$C_8$)alkyl-$NR^a$—C(O)$R^a$, —$SO_2$—$NR^aR^{a'}$ and —$SO_2R^a$;

wherein, $R^a$ and $R^{a'}$ independently represent hydrogen, $C_1$-$C_8$ alkyl, $C_3$-$C_9$ cycloalkyl, hydroxyl, halogen, amino, $C_1$-$C_8$ haloalkyl, $C_1$-$C_8$ alkylamino, di-$C_1$-$C_8$ alkylamino group or $R^a$, $R^{a'}$ together with the atom directly attached thereto form a 3-9 membered cycloalkyl or heterocycloalkyl ring;

n is 1, 2 or 3; m and o independently represent 0, 1, 2 or 3, for the above-defined alkyl, cycloalkyl, heterocycloalkyl, aryl, and heteroaryl groups, can further be substituted with the substituents selected from the following: $C_1$-$C_8$ alkyl, $C_2$-$C_8$ alkenyl, $C_2$-$C_8$ alkynyl, $C_3$-$C_8$ cycloalkyl, 5-12 membered aryl, 5-12 membered heteroaryl, $C_1$-$C_8$ haloalkyl, $C_1$-$C_8$ alkoxy, $C_1$-$C_8$ alkylthio, halogen, hydroxyl, cyano, sulfonic and nitro;

for the above-defined substituents, each of the different substituents $R^a$ or $R^{a'}$ has its own independent definition.

2. The compound of claim 1 or a pharmaceutically acceptable salt, solvate, hydrate, stereoisomer, a mixture of stereoisomers or a racemic mixture of stereoisomers thereof, wherein $R^1$, $R^2$ together with the carbon atom directly attached thereto form a saturated or unsaturated 3-6 membered cycloalkyl or cycloheteroalkyl ring, and the said cycloalkyl or heterocycloalkyl, and the heterocycloalkyl contains at least one heteroatom selected from O, N and S atoms, the cycloalkyl or heterocycloalkyl group may be optionally substituted with 0, 1, 2, 3, or 4 substituents each independently selected from the following $R^6$, wherein $R^6$ is as defined in claim 1.

3. The compound of claim 1 or a pharmaceutically acceptable salt, solvate, hydrate, stereoisomer, a mixture of stereoisomers or a racemic mixture of stereoisomers thereof, wherein $R^1$, $R^2$ and together with the carbon atom directly attached thereto form the following structures:

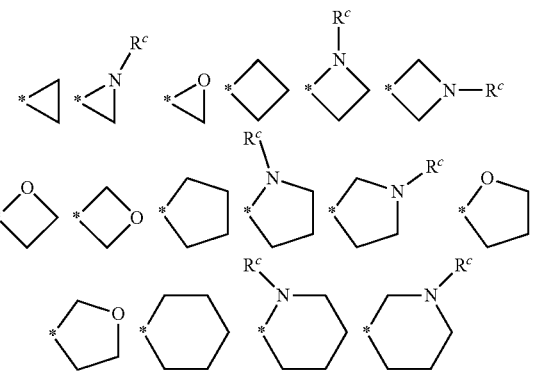

-continued

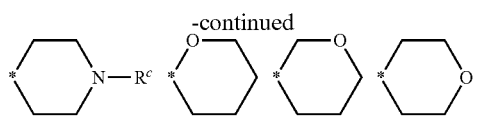

wherein, $R^c$ is selected from hydrogen, $C_1$-$C_6$ alkyl, $C_3$-$C_8$ cycloalkyl, —C(O)$R^a$, —C(O)O$R^a$, —C(O)—N$R^a R^{a'}$, —SO$_2$—N$R^a R^{a'}$, and —SO$_2 R^a$;

\* represents the binding site of $R^1$ and $R^2$ and the carbon atom connected to them;

and the above-mentioned groups may be optionally substituted by 0, 1, 2, 3, 4 substituents independently selected from the following $R^6$ substitution, wherein $R^a$, $R^{a'}$ and $R^6$ are as defined in claim 1.

4. The compound according to claim 1 or a pharmaceutically acceptable salt, solvate, hydrate, stereoisomer, a mixture of stereoisomers or a racemic mixture of stereoisomers thereof, wherein X is selected from C$R^a R^{a'}$, N$R^a$, O and S; wherein, $R^a$ and $R^{a'}$ are selected from hydrogen, $C_1$-$C_8$ alkyl, $C_3$-$C_8$ cycloalkyl, hydroxyl, halogen, $C_1$-$C_8$ haloalkyl, $C_1$-$C_8$ alkylamino, di-($C_1$-$C_8$) alkylamino, or $R^a$, $R^{a'}$ together with the atom directly attached thereto form a 3-9 membered cycloalkyl or heterocycloalkyl ring.

5. The compound of claim 1 or a pharmaceutically acceptable salt, solvate, hydrate, stereoisomer, mixture of stereoisomers or racemic mixture of stereoisomers thereof, wherein: $R^4$ is Cy$^2$, —NHC(O)$R^a$, —C(O)N$R^a R^{a'}$ or —NHC(O)N$R^a R^{a'}$, wherein Cy$^2$, $R^a$, $R^{a'}$ are as defined in claim 1.

6. The compound of claim 1 or a pharmaceutically acceptable salt, solvate, hydrate, stereoisomer, a mixture of stereoisomers or a racemic mixture of stereoisomers thereof, wherein: Cy$^2$ is selected from phenyl, pyridyl, pyrazinyl, cyclopropyl, cyclopentyl, cyclohexyl, furyl, thiazolyl, piperidinyl, piperazinyl, oxazolyl, imidazolyl and thienyl; and the Cy$^2$ can be optionally substituted by $C_1$-$C_8$ alkyl, $C_1$-$C_8$ alkoxy, $C_3$-$C_9$ cycloalkane group, $C_3$-$C_9$ heterocyclic group, $C_1$-$C_8$ haloalkyl, halogen, cyano, sulfonic acid, nitro or hydroxy.

7. The compound according to claim 1, or a pharmaceutically acceptable salt, solvate, hydrate, stereoisomer, a mixture of stereoisomers or a racemic mixture of stereoisomers thereof, wherein: $R^a$ and $R^{a'}$ are hydrogen, halogen or $C_1$-$C_8$ alkyl.

8. The compound according to claim 1 or a pharmaceutically acceptable salt, solvate, hydrate, stereoisomer, a mixture of stereoisomers or a racemic mixture of stereoisomers thereof, wherein the compound has a structure selected from:

| NO. | Structure |
|---|---|
| 1 | 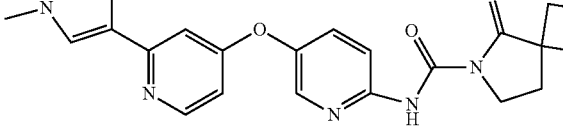 |
| 2 | 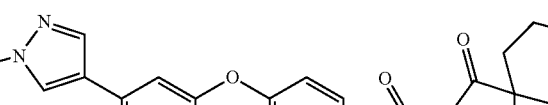 |
| 3 | 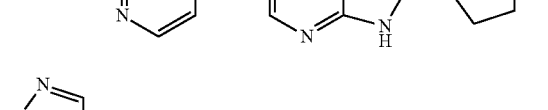 |
| 4 | 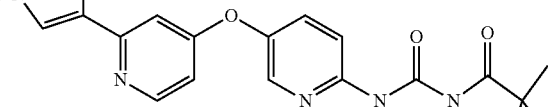 |
| 5 | 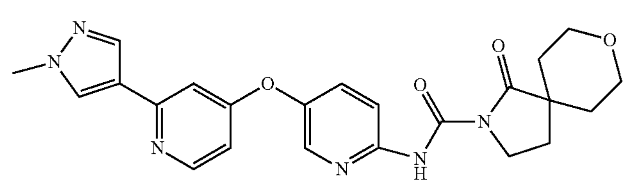 [SMILES: Cn1cc(-c2cc(Oc3ccc(NC(=O)N4CCC5(CCOCC5)C4=O)nc3)ccn2)cn1] |

| NO. | Structure |
|---|---|
| 6 | 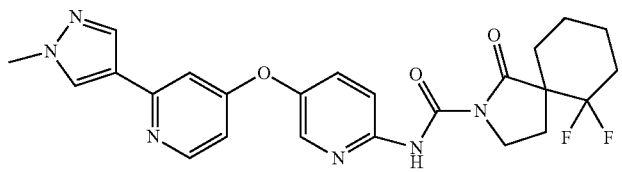 [SMILES: Cn1cc(-c2cc(Oc3ccc(NC(=O)N4CCC5(CCCCC5(F)F)C4=O)nc3)ccn2)cn1] |
| 7 | 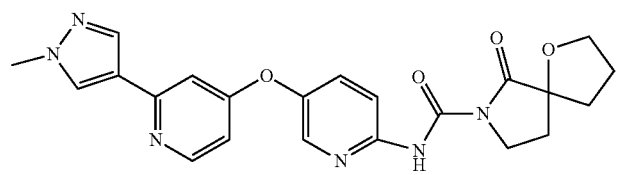 [SMILES: Cn1cc(-c2cc(Oc3ccc(NC(=O)N4CCC5(CCCO5)C4=O)nc3)ccn2)cn1] |
| 8 | 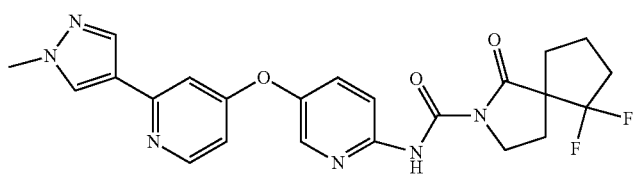 [SMILES: Cn1cc(-c2cc(Oc3ccc(NC(=O)N4CCC5(CCCC5(F)F)C4=O)nc3)ccn2)cn1] |
| 9 | 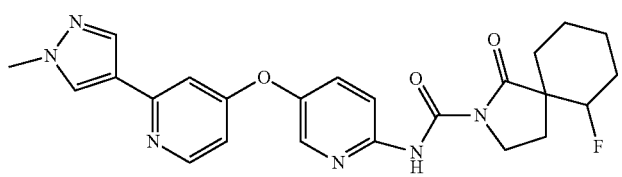 [SMILES: Cn1cc(-c2cc(Oc3ccc(NC(=O)N4CCC5(CCCCC5F)C4=O)nc3)ccn2)cn1] |
| 10 | 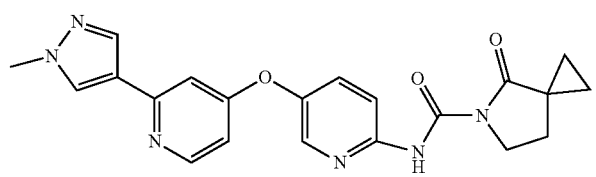 [SMILES: Cn1cc(-c2cc(Oc3ccc(NC(=O)N4CCC5(CC5)C4=O)nc3)ccn2)cn1] |
| 11 | 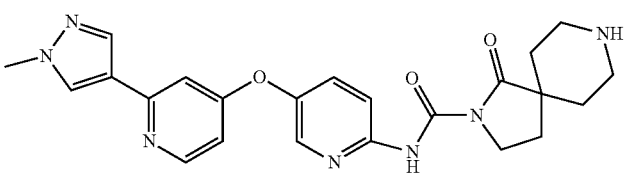 [SMILES: Cn1cc(-c2cc(Oc3ccc(NC(=O)N4CCC5(CCNCC5)C4=O)nc3)ccn2)cn1] |
| 12 | 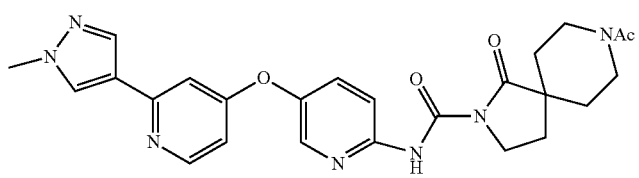 |
| 13 | 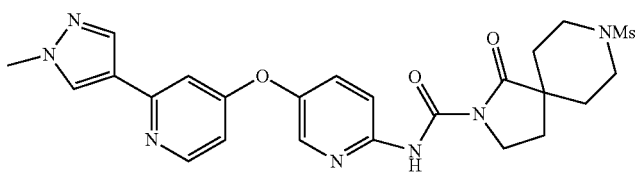 |

-continued

| NO. | Structure |
|---|---|
| 14 | 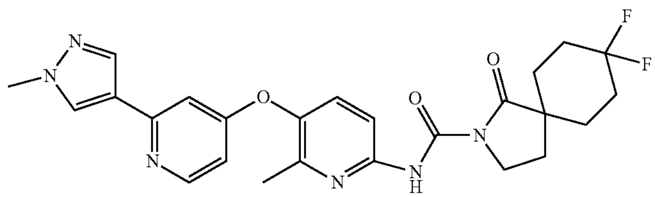 [SMILES: Cc1nc(NC(=O)N2CCC3(CCC(F)(F)CC3)C2=O)ccc1Oc1ccnc(-c2cnn(C)c2)c1] |
| 15 | 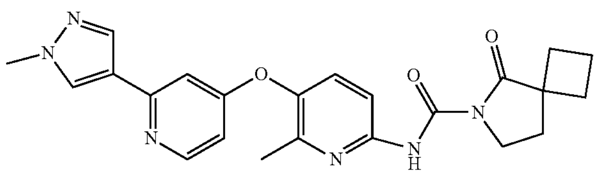 [SMILES: Cc1nc(NC(=O)N2CCC3(CCC3)C2=O)ccc1Oc1ccnc(-c2cnn(C)c2)c1] |
| 16 | 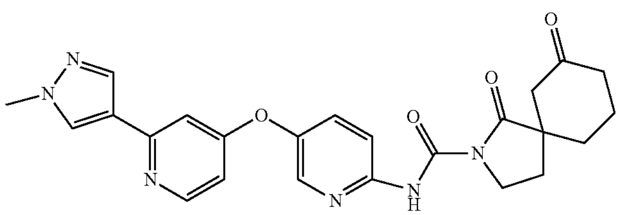 [SMILES: Cn1cc(-c2cc(Oc3ccc(NC(=O)N4CCC5(CCCC(=O)C5)C4=O)nc3)ccn2)cn1] |
| 17 | 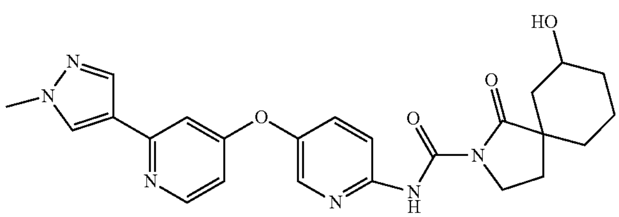 [SMILES: Cn1cc(-c2cc(Oc3ccc(NC(=O)N4CCC5(CCCC(O)C5)C4=O)nc3)ccn2)cn1] |
| 18 | 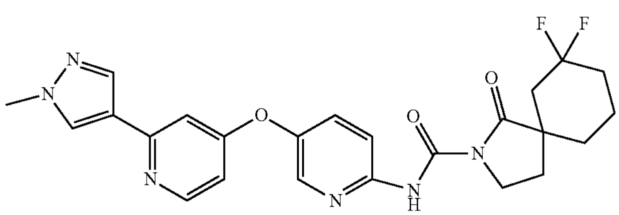 [SMILES: Cn1cc(-c2cc(Oc3ccc(NC(=O)N4CCC5(CCCC(F)(F)C5)C4=O)nc3)ccn2)cn1] |
| 19 | 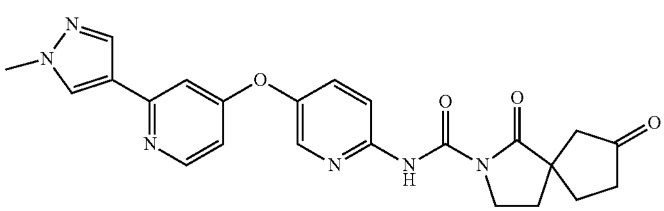 [SMILES: Cn1cc(-c2cc(Oc3ccc(NC(=O)N4CCC5(CCC(=O)C5)C4=O)nc3)ccn2)cn1] |
| 20 | 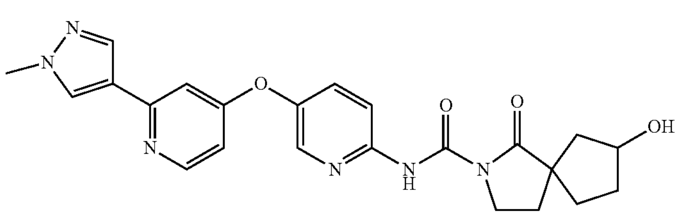 [SMILES: Cn1cc(-c2cc(Oc3ccc(NC(=O)N4CCC5(CCC(O)C5)C4=O)nc3)ccn2)cn1] |

-continued

| NO. | Structure |
|---|---|
| 21 | 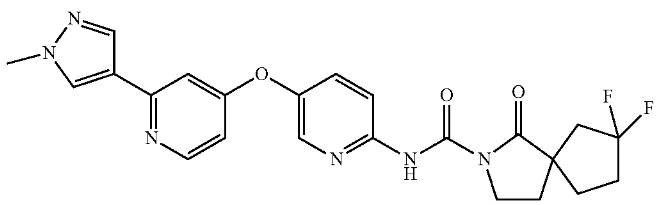 [SMILES: Cn1cc(-c2cc(Oc3ccc(NC(=O)N4CCC5(CCC(F)(F)C5)C4=O)nc3)ccn2)cn1] |
| 22 | 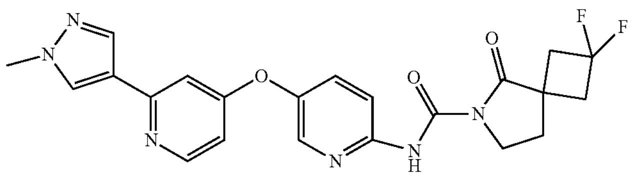 [SMILES: Cn1cc(-c2cc(Oc3ccc(NC(=O)N4CCC5(CC(F)(F)C5)C4=O)nc3)ccn2)cn1] |
| 23 | 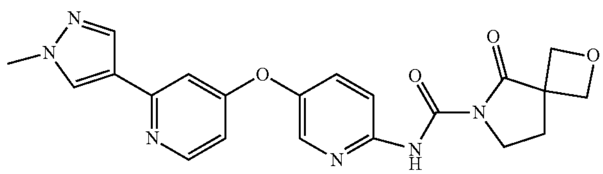 [SMILES: Cn1cc(-c2cc(Oc3ccc(NC(=O)N4CCC5(COC5)C4=O)nc3)ccn2)cn1] |
| 24 | 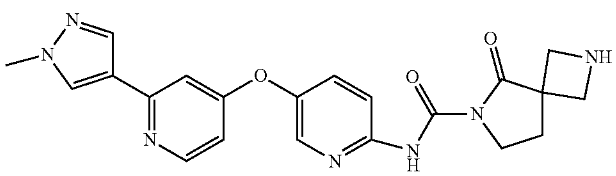 [SMILES: Cn1cc(-c2cc(Oc3ccc(NC(=O)N4CCC5(CNC5)C4=O)nc3)ccn2)cn1] |
| 25 | 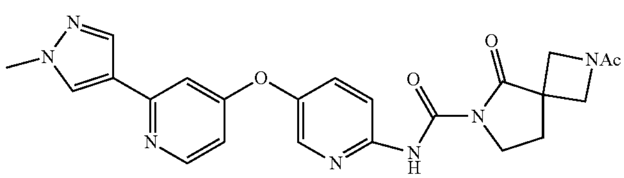 |
| 26 | 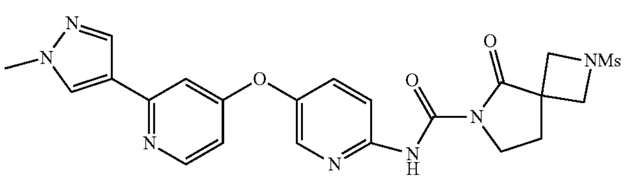 |
| 27 | 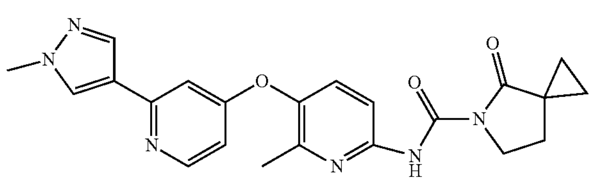 [SMILES: Cc1nc(NC(=O)N2CCC3(CC3)C2=O)ccc1Oc1ccnc(-c2cnn(C)c2)c1] |
| 28 | 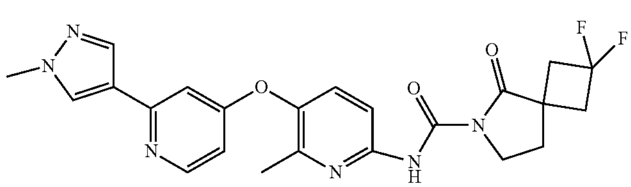 [SMILES: Cc1nc(NC(=O)N2CCC3(CC(F)(F)C3)C2=O)ccc1Oc1ccnc(-c2cnn(C)c2)c1] |

-continued

| NO. | Structure |
|---|---|
| 29 | 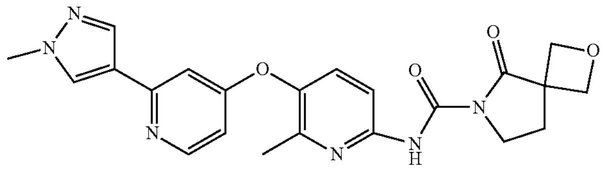 [SMILES: Cc1nc(NC(=O)N2CCC3(COC3)C2=O)ccc1Oc1ccnc(-c2cnn(C)c2)c1] |
| 30 | 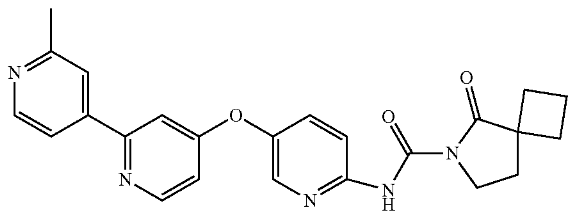 [SMILES: Cc1cc(-c2cc(Oc3ccc(NC(=O)N4CCC5(CCC5)C4=O)nc3)ccn2)ccn1] |
| 31 | 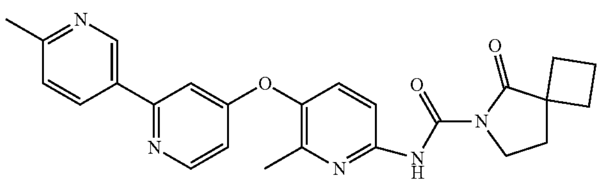 [SMILES: Cc1ccc(-c2cc(Oc3ccc(NC(=O)N4CCC5(CCC5)C4=O)nc3C)ccn2)cn1] |
| 32 | 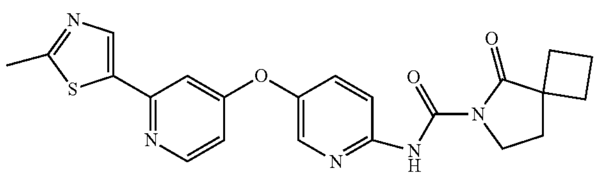 [SMILES: Cc1ncc(-c2cc(Oc3ccc(NC(=O)N4CCC5(CCC5)C4=O)nc3)ccn2)s1] |
| 33 | 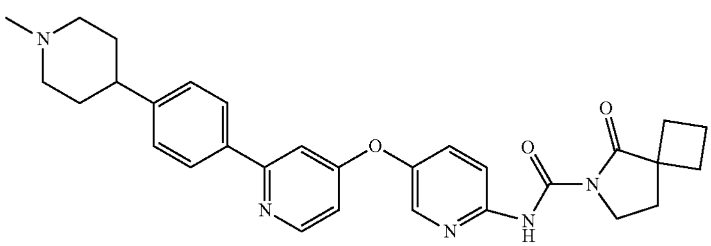 [SMILES: CN1CCC(c2ccc(-c3cc(Oc4ccc(NC(=O)N5CCC6(CCC6)C5=O)nc4)ccn3)cc2)CC1] |
| 34 | 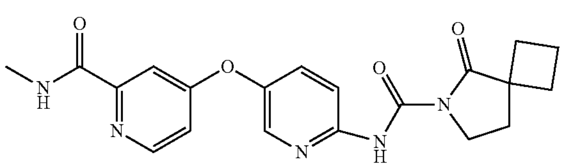 [SMILES: CNC(=O)c1cc(Oc2ccc(NC(=O)N3CCC4(CCC4)C3=O)nc2)ccn1] |
| 35 | 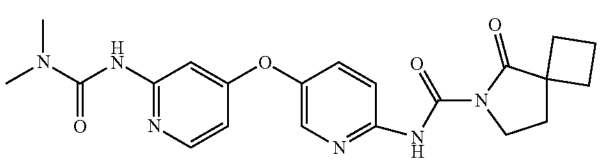 [SMILES: CN(C)C(=O)Nc1cc(Oc2ccc(NC(=O)N3CCC4(CCC4)C3=O)nc2)ccn1] |
| 36 | 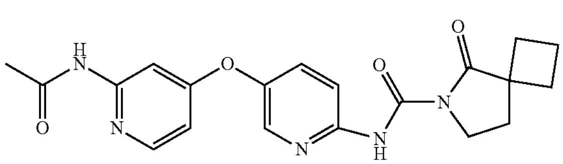 [SMILES: CC(=O)Nc1cc(Oc2ccc(NC(=O)N3CCC4(CCC4)C3=O)nc2)ccn1] |

| NO. | Structure |
|---|---|
| 37 | 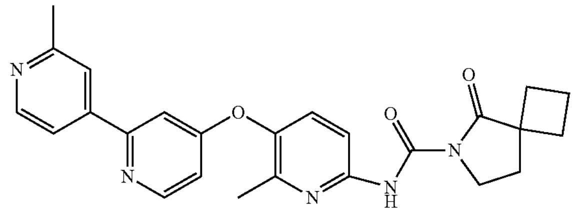 [SMILES: Cc1cc(-c2cc(Oc3ccc(NC(=O)N4CCC5(CCC5)C4=O)nc3C)ccn2)ccn1] |
| 38 | 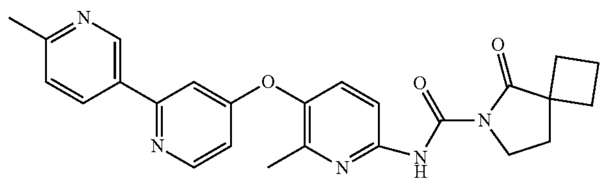 [SMILES: Cc1ccc(-c2cc(Oc3ccc(NC(=O)N4CCC5(CCC5)C4=O)nc3C)ccn2)cn1] |
| 39 | 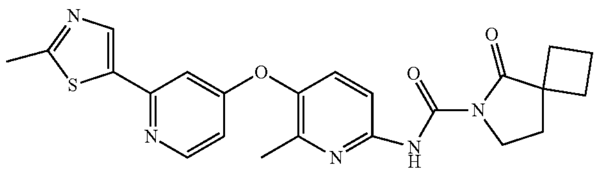 [SMILES: Cc1ncc(-c2cc(Oc3ccc(NC(=O)N4CCC5(CCC5)C4=O)nc3C)ccn2)s1] |
| 40 | 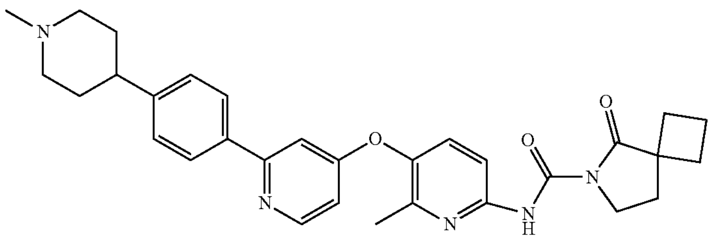 [SMILES: Cc1nc(NC(=O)N2CCC3(CCC3)C2=O)ccc1Oc1ccnc(-c2ccc(C3CCN(C)CC3)cc2)c1] |
| 41 | 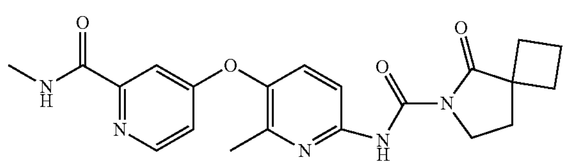 [SMILES: CNC(=O)c1cc(Oc2ccc(NC(=O)N3CCC4(CCC4)C3=O)nc2C)ccn1] |
| 42 | 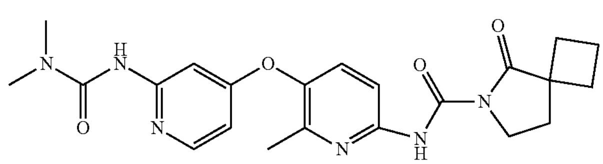 [SMILES: Cc1nc(NC(=O)N2CCC3(CCC3)C2=O)ccc1Oc1ccnc(NC(=O)N(C)C)c1] |
| 43 | 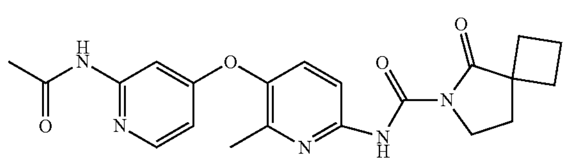 [SMILES: CC(=O)Nc1cc(Oc2ccc(NC(=O)N3CCC4(CCC4)C3=O)nc2C)ccn1] |
| 44 | 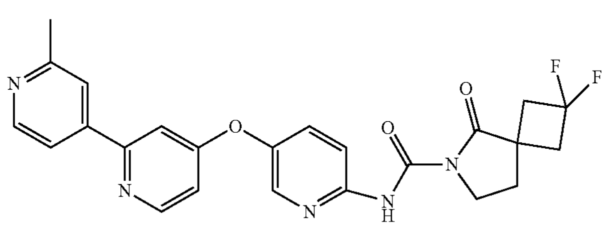 [SMILES: Cc1cc(-c2cc(Oc3ccc(NC(=O)N4CCC5(CC(F)(F)C5)C4=O)nc3)ccn2)ccn1] |

| NO. | Structure |
|---|---|
| 45 | 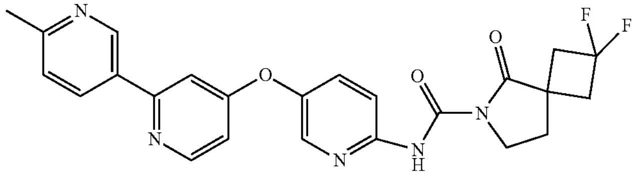 [SMILES: Cc1ccc(-c2cc(Oc3ccc(NC(=O)N4CCC5(CC(F)(F)C5)C4=O)nc3)ccn2)cn1] |
| 46 | 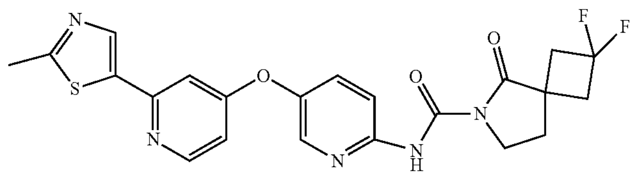 [SMILES: Cc1ncc(-c2cc(Oc3ccc(NC(=O)N4CCC5(CC(F)(F)C5)C4=O)nc3)ccn2)s1] |
| 47 | 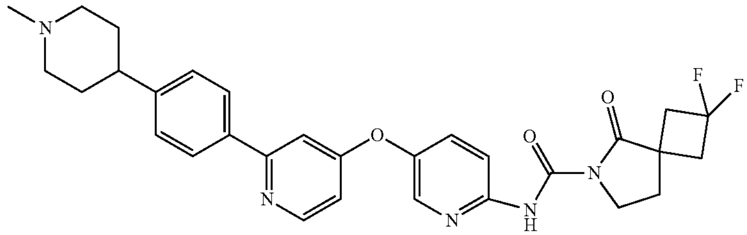 [SMILES: CN1CCC(c2ccc(-c3cc(Oc4ccc(NC(=O)N5CCC6(CC(F)(F)C6)C5=O)nc4)ccn3)cc2)CC1] |
| 48 | 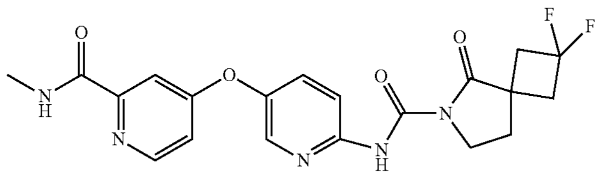 [SMILES: CNC(=O)c1cc(Oc2ccc(NC(=O)N3CCC4(CC(F)(F)C4)C3=O)nc2)ccn1] |
| 49 | 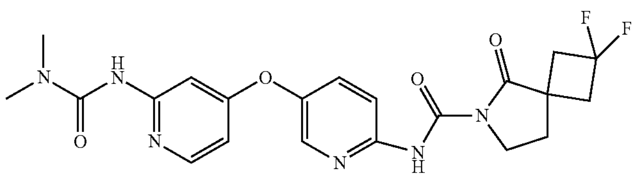 [SMILES: CN(C)C(=O)Nc1cc(Oc2ccc(NC(=O)N3CCC4(CC(F)(F)C4)C3=O)nc2)ccn1] |
| 50 | 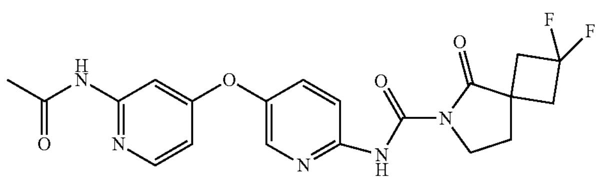 [SMILES: CC(=O)Nc1cc(Oc2ccc(NC(=O)N3CCC4(CC(F)(F)C4)C3=O)nc2)ccn1] |
| 51 | 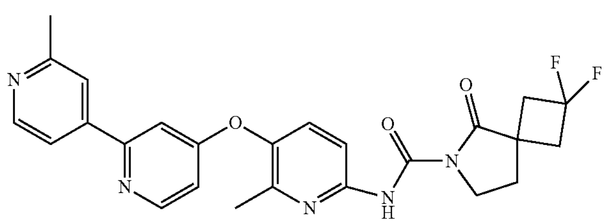 [SMILES: Cc1cc(-c2cc(Oc3ccc(NC(=O)N4CCC5(CC(F)(F)C5)C4=O)nc3C)ccn2)ccn1] |
| 52 | 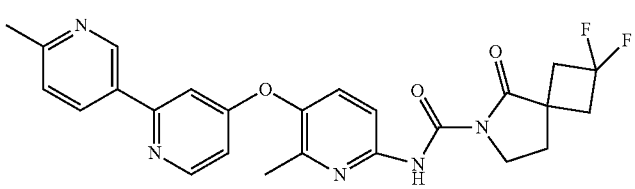 [SMILES: Cc1ccc(-c2cc(Oc3ccc(NC(=O)N4CCC5(CC(F)(F)C5)C4=O)nc3C)ccn2)cn1] |

| NO. | Structure |
|---|---|
| 53 | 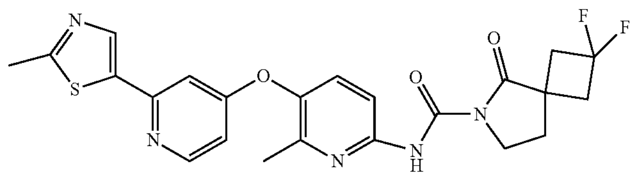 [SMILES: Cc1ncc(-c2cc(Oc3ccc(NC(=O)N4CCC5(CC(F)(F)C5)C4=O)nc3C)ccn2)s1] |
| 54 | 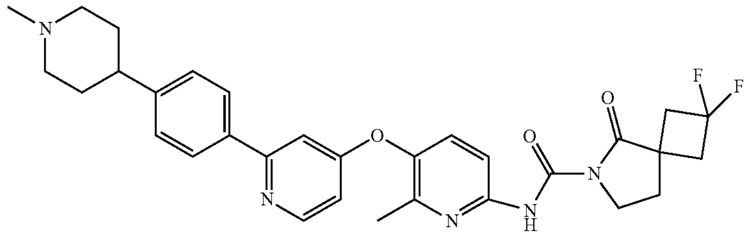 [SMILES: Cc1nc(NC(=O)N2CCC3(CC(F)(F)C3)C2=O)ccc1Oc1ccnc(-c2ccc(C3CCN(C)CC3)cc2)c1] |
| 55 | 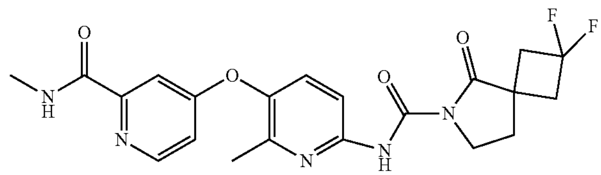 [SMILES: CNC(=O)c1cc(Oc2ccc(NC(=O)N3CCC4(CC(F)(F)C4)C3=O)nc2C)ccn1] |
| 56 | 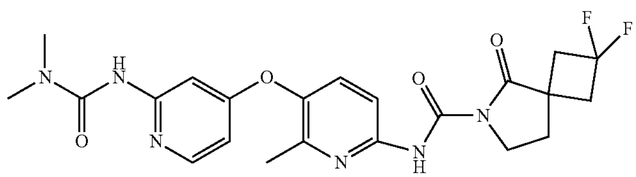 [SMILES: Cc1nc(NC(=O)N2CCC3(CC(F)(F)C3)C2=O)ccc1Oc1ccnc(NC(=O)N(C)C)c1] |
| 57 | 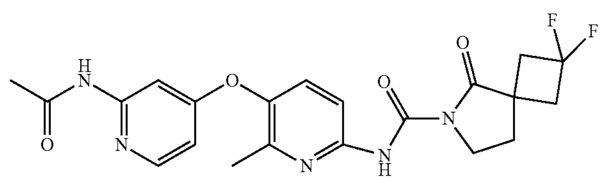 [SMILES: CC(=O)Nc1cc(Oc2ccc(NC(=O)N3CCC4(CC(F)(F)C4)C3=O)nc2C)ccn1] |
| 58 | 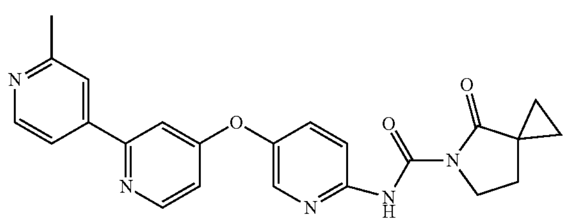 [SMILES: Cc1cc(-c2cc(Oc3ccc(NC(=O)N4CCC5(CC5)C4=O)nc3)ccn2)ccn1] |
| 59 | 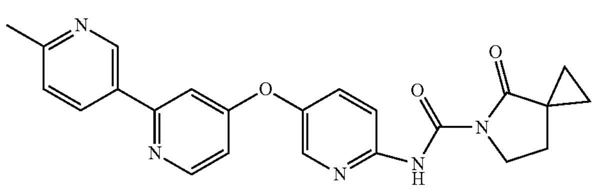 [SMILES: Cc1ccc(-c2cc(Oc3ccc(NC(=O)N4CCC5(CC5)C4=O)nc3)ccn2)cn1] |
| 60 | 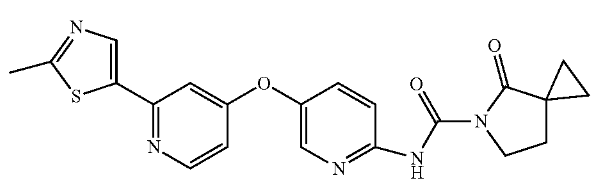 [SMILES: Cc1ncc(-c2cc(Oc3ccc(NC(=O)N4CCC5(CC5)C4=O)nc3)ccn2)s1] |

-continued

| NO. | Structure |
|---|---|
| 61 | 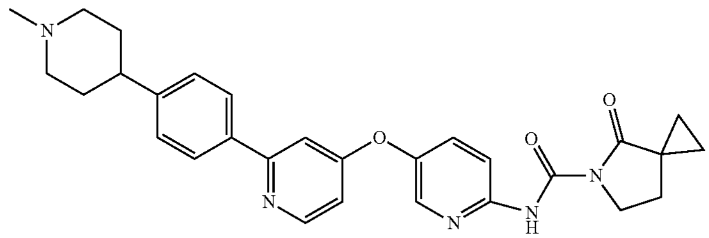 [SMILES: CN1CCC(c2ccc(-c3cc(Oc4ccc(NC(=O)N5CCC6(CC6)C5=O)nc4)ccn3)cc2)CC1] |
| 62 | 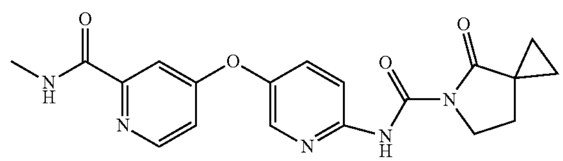 [SMILES: CNC(=O)c1cc(Oc2ccc(NC(=O)N3CCC4(CC4)C3=O)nc2)ccn1] |
| 63 | 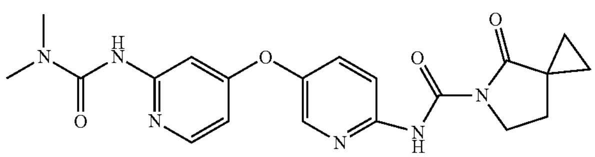 [SMILES: CN(C)C(=O)Nc1cc(Oc2ccc(NC(=O)N3CCC4(CC4)C3=O)nc2)ccn1] |
| 64 | 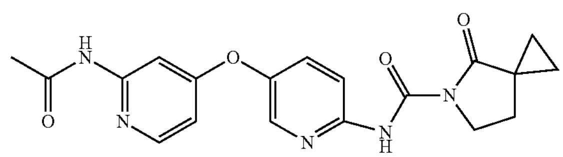 [SMILES: CC(=O)Nc1cc(Oc2ccc(NC(=O)N3CCC4(CC4)C3=O)nc2)ccn1] |
| 65 | 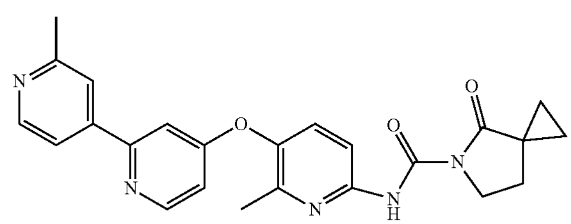 [SMILES: Cc1cc(-c2cc(Oc3ccc(NC(=O)N4CCC5(CC5)C4=O)nc3C)ccn2)ccn1] |
| 66 | 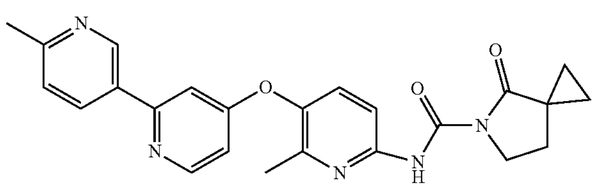 [SMILES: Cc1ccc(-c2cc(Oc3ccc(NC(=O)N4CCC5(CC5)C4=O)nc3C)ccn2)cn1] |
| 67 | 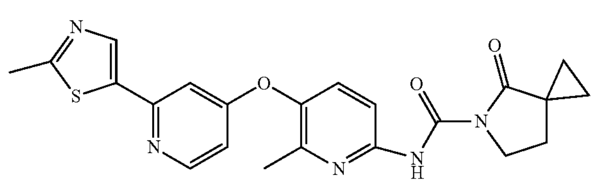 [SMILES: Cc1ncc(-c2cc(Oc3ccc(NC(=O)N4CCC5(CC5)C4=O)nc3C)ccn2)s1] |
| 68 | 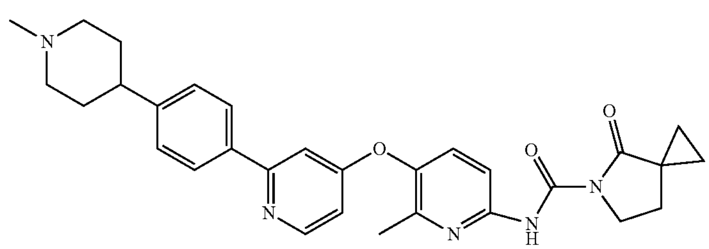 [SMILES: Cc1nc(NC(=O)N2CCC3(CC3)C2=O)ccc1Oc1ccnc(-c2ccc(C3CCN(C)CC3)cc2)c1] |

| NO. | Structure |
|---|---|
| 69 | 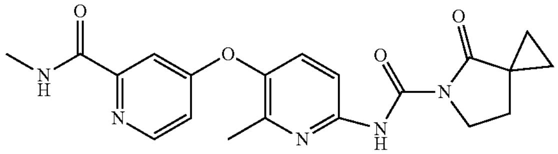 [SMILES: CNC(=O)c1cc(Oc2ccc(NC(=O)N3CCC4(CC4)C3=O)nc2C)ccn1] |
| 70 | 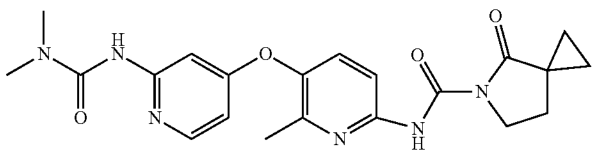 [SMILES: Cc1nc(NC(=O)N2CCC3(CC3)C2=O)ccc1Oc1ccnc(NC(=O)N(C)C)c1] |
| 71 | 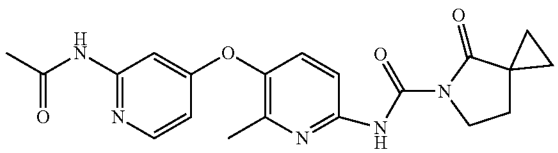 [SMILES: CC(=O)Nc1cc(Oc2ccc(NC(=O)N3CCC4(CC4)C3=O)nc2C)ccn1] |
| 72 | 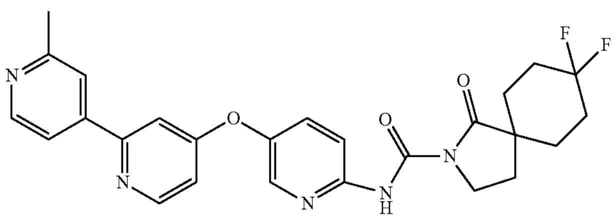 [SMILES: Cc1cc(-c2cc(Oc3ccc(NC(=O)N4CCC5(CCC(F)(F)CC5)C4=O)nc3)ccn2)ccn1] |
| 73 | 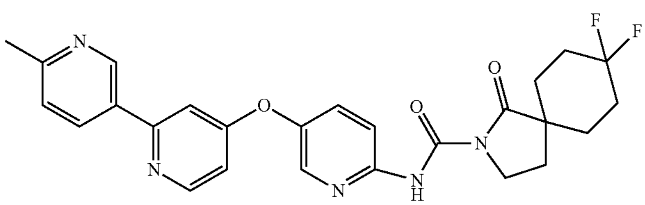 [SMILES: Cc1ccc(-c2cc(Oc3ccc(NC(=O)N4CCC5(CCC(F)(F)CC5)C4=O)nc3)ccn2)cn1] |
| 74 | 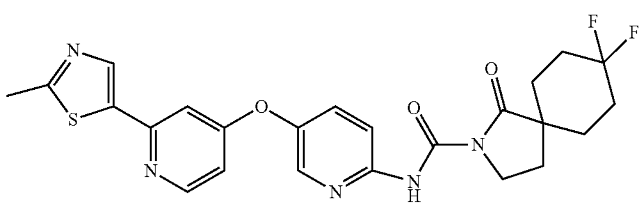 [SMILES: Cc1ncc(-c2cc(Oc3ccc(NC(=O)N4CCC5(CCC(F)(F)CC5)C4=O)nc3)ccn2)s1] |
| 75 | 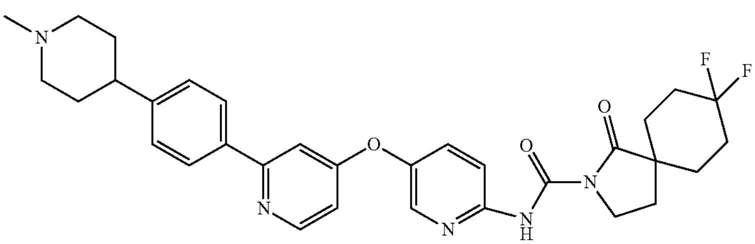 [SMILES: CN1CCC(c2ccc(-c3cc(Oc4ccc(NC(=O)N5CCC6(CCC(F)(F)CC6)C5=O)nc4)ccn3)cc2)CC1] |
| 76 | 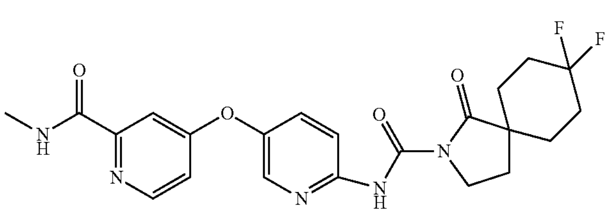 [SMILES: CNC(=O)c1cc(Oc2ccc(NC(=O)N3CCC4(CCC(F)(F)CC4)C3=O)nc2)ccn1] |

| NO. | Structure |
|---|---|
| 77 | 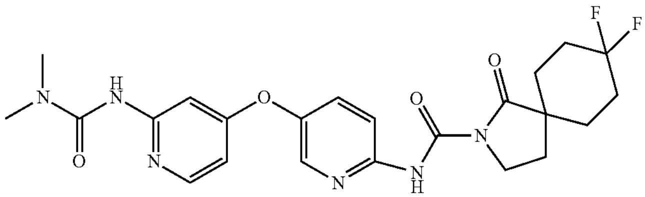 [SMILES: CN(C)C(=O)Nc1cc(Oc2ccc(NC(=O)N3CCC4(CCC(F)(F)CC4)C3=O)nc2)ccn1] |
| 78 | 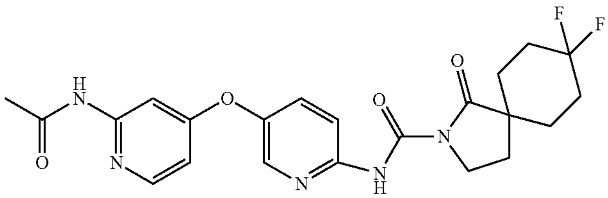 [SMILES: CC(=O)Nc1cc(Oc2ccc(NC(=O)N3CCC4(CCC(F)(F)CC4)C3=O)nc2)ccn1] |
| 79 | 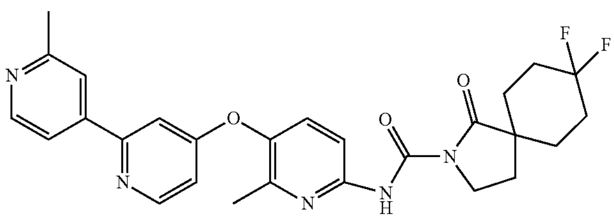 [SMILES: Cc1cc(-c2cc(Oc3ccc(NC(=O)N4CCC5(CCC(F)(F)CC5)C4=O)nc3C)ccn2)ccn1] |
| 80 | 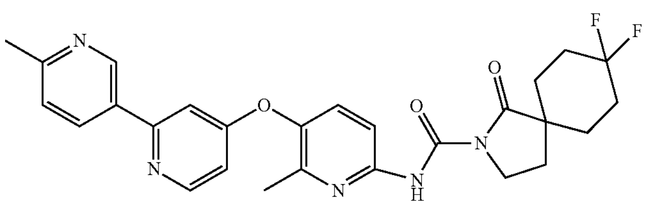 [SMILES: Cc1ccc(-c2cc(Oc3ccc(NC(=O)N4CCC5(CCC(F)(F)CC5)C4=O)nc3C)ccn2)cn1] |
| 81 | 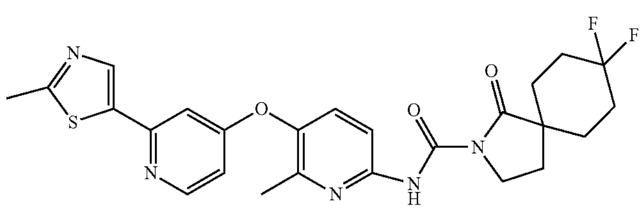 [SMILES: Cc1ncc(-c2cc(Oc3ccc(NC(=O)N4CCC5(CCC(F)(F)CC5)C4=O)nc3C)ccn2)s1] |
| 82 | 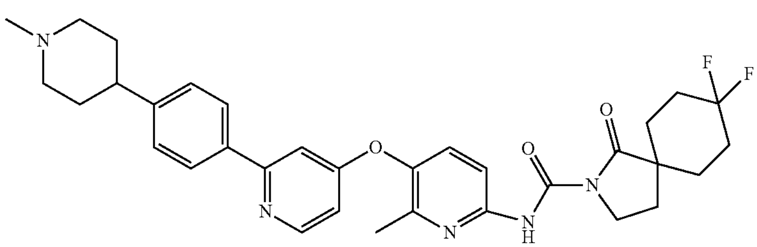 [SMILES: Cc1nc(NC(=O)N2CCC3(CCC(F)(F)CC3)C2=O)ccc1Oc1ccnc(-c2ccc(C3CCN(C)CC3)cc2)c1] |
| 83 | 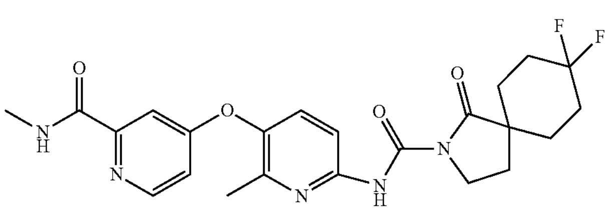 [SMILES: CNC(=O)c1cc(Oc2ccc(NC(=O)N3CCC4(CCC(F)(F)CC4)C3=O)nc2C)ccn1] |

| NO. | Structure |
|---|---|
| 84 | *(structure)* |
| 85 | *(structure)* |
| 86 | *(structure)* |
| 87 | *(structure)* |
| 88 | *(structure)* |
| 89 | *(structure)* |
| 90 | *(structure)* |

9. A pharmaceutical composition comprising the compound of claim 8 or a pharmaceutically acceptable salt, solvate, hydrate, stereoisomer, a mixture of stereoisomers or a racemic mixture of stereoisomers thereof, and a pharmaceutically acceptable carrier.

10. The pharmaceutical composition or pharmaceutical preparation according to claim 9, which further comprises an additional therapeutic agent and/or an immune checkpoint inhibitor, the additional therapeutic agent is selected from chlorambucil, melphalan, cyclophosphamide, ifosfamide, busulfan, carmustine, lomustine, streptozotocin, cisplatin, carboplatin, oxaliplatin, Dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, Topotecan, irinotecan, etoposide, trabectedin, probiotic, doxorubicin, epirubicin, daunorubicin, mitoxantrone, bleomycin, mitomycin C, ixabepilone, tamoxifen, flutamide, gonadorelin analogs, megestrol, prednisone, dexamethasone, methylprednisolone, thalidomide, interferona, alcium Folinate, sirolimus, sirolimus lipid, everolimus, afatinib, alisertib, amuvatinib, apatinib, axitinib, bortezomib, bosutinib, Brivanib, Carbotinib, Cediranib, crenolanib, crizotinib, Dabrafenib, Dacomitinib, danusertib, dasatinib, dovitinib, Erlotinib, foretinib, ganetespib, gefitinib, ibrutinib, icotinib, imatinib, iniparib, lapatinib, lenvatinib, linifanib, linsitinib, masitinib, momelotinib, Motesanib, lenatinib, nilotinib, niraparib, oprozomib, olaparib, pazopanib, pictilisib, ponatinib, quizartinib, Regorafenib, rigosertib, rucaparib, ruxolitinib, saracatinib, saridegib, sorafenib, sunitinib, tilatinib, tivantinib, Tivozanib, tofacitinib, trametinib, vandetanib, Veliparib, Vemurafenib, Vismodegib, Volasertib, Alemtuzumab, Bevacizumab, brentuximab vedotin, Victorin, Catumaxomab, Cetuximab, Denosumab, Getuzumab, ipilimumab, nimotuzumab, ofatumumab, panitumumab, rituximab, Tositumomab, trastuzumab, IDO inhibitor, anti-PD-1 antibody, anti-PD-L1 antibody, LAG3 antibody, TIM-3 antibody and anti-CTLA-4 antibody.

11. A method of treating tumors or cancers that can be treated by inhibiting CSF1R, comprising administering a compound according to claim 8 or a pharmaceutically acceptable salt, solvate, hydrate, stereoisomer, a mixture of stereoisomers or a racemic mixture of stereoisomers thereof to the subject.

12. The method according to claim 11, wherein the tumor or cancer that can be treated by inhibiting CSF1R is selected from skin cancer, bladder cancer, Ovarian cancer, breast cancer; gastric carcinoma, pancreatic cancer; prostatic cancer, colorectal carcinoma, Lung Cancer, bone cancer, brain cancer, Neurocytoma, rectal cancer, colon cancer, familial adenomatous polyposis, hereditary nonpolyposis colorectal cancer, esophageal carcinoma, lip cancer, laryngocar, hypopharyngeal carcinoma, tongue cancer, salivary gland carcinoma, gastric carcinoma, adenocarcinoma, medullary thyroid carcinoma, papillary thyroid cancer, kidney cancer, carcinoma of renal pelvis, Ovarian Carcinoma, cervical carcinoma, carcinoma of the corpus uteri, endometrial carcinoma, choriocarcinoma, prostatic cancer, pancreatic cancer, testicular cancer, Urinary cancer, melanoma, Brain tumors such as glioblastoma and astrocytoma, meningeoma, Neuroblastoma and peripheral neuroectodermal tumor, Hodgkin's lymphoma, Non Hodgkin's lymphoma, Burkitt's lymphoma, acute lymphoid leukemia, Acute lymphoblastic leukemia (ALL), Chronic Lymphocytic Leukemia (CLL), Acute myeloid leukemia (AML), Chronic myelogenous leukemia (CML), Adult T-cell leukemia lymphoma, Diffuse large B cell lymphoma (DLBCL), hepatic cellular cancer, gallbladder cancer, bronchogenic carcinoma, small-cell lung carcinoma, non-small-cell lung cancer, multiple myeloma, Basaloma, Teratoma, retinoblastoma, choroidal melanoma, seminoma, rhabdomyosarcoma, craniopharyngioma, osteosarcoma, chondrosarcoma, myosarcoma, liposarcoma, fibrosarcoma, Ewing's sarcoma, and plasmacytoma.

13. A method for inhibiting CSF1R, which comprises making the compound or a pharmaceutically acceptable salt, solvate, hydrate, stereoisomer, a mixture of stereoisomers or a racemic mixture of stereoisomers thereof of claim 1 exposed to the CSF1R.

14. A method for treating diseases that can be treated by inhibiting CSF1R, which comprises administering a subject in need thereof a compound or a pharmaceutically acceptable salts, solvates, hydrates, stereoisomers, a mixture of stereoisomers or a racemic mixture of stereoisomers thereof of claim 1.

15. The compound of claim 1 or a pharmaceutically acceptable salt, solvate, hydrate, stereoisomer, a mixture of stereoisomers or a racemic mixture of stereoisomers thereof, wherein $Cy^1$ and $Cy^2$ each independently represent a 5-12 membered aryl group or a 5-12 membered heteroaryl group.

16. The compound of claim 1 or a pharmaceutically acceptable salt, solvate, hydrate, stereoisomer, a mixture of stereoisomers or a racemic mixture of stereoisomers thereof, wherein $Cy^1$ and $Cy^2$ each independently represent a 5-6 membered aryl group or a 5-6 membered heteroaryl group.

17. The compound of claim 1 or a pharmaceutically acceptable salt, solvate, hydrate, stereoisomer, a mixture of stereoisomers or a racemic mixture of stereoisomers thereof, wherein $R^a$ and $R^{a'}$ independently represent hydrogen, $C_1$-$C_8$ alkyl or $C_3$-$C_8$ cycloalkyl.

18. The compound of claim 4 or a pharmaceutically acceptable salt, solvate, hydrate, stereoisomer, a mixture of stereoisomers or a racemic mixture of stereoisomers thereof, wherein X is O.

19. The compound of claim 4 or a pharmaceutically acceptable salt, solvate, hydrate, stereoisomer, a mixture of stereoisomers or a racemic mixture of stereoisomers thereof, wherein $R^a$ and $R^{a'}$ are selected from hydrogen, halogen or $C_1$-$C_8$ alkyl.

20. The compound of claim 1 or a pharmaceutically acceptable salt, solvate, hydrate, stereoisomer, a mixture of stereoisomers or a racemic mixture of stereoisomers thereof, wherein $Cy^2$ is selected from pyrazolyl, imidazolyl, oxazolyl, thiazolyl, phenyl and pyridyl, and the $Cy^2$ can be optionally substituted by $C_1$-$C_8$ alkyl, $C_1$-$C_8$ alkoxy, $C_3$-$C_9$ cycloalkane group, $C_3$-$C_9$ heterocyclic group, $C_1$-$C_8$ haloalkyl, halogen, cyano, sulfonic acid, nitro or hydroxy.

* * * * *